United States Patent
Wong et al.

(10) Patent No.: US 7,888,337 B2
(45) Date of Patent: Feb. 15, 2011

(54) SYNTHESIS OF OSELTAMIVIR CONTAINING PHOSPHONATE CONGENERS WITH ANTI-INFLUENZA ACTIVITY

(75) Inventors: Chi-Huey Wong, La Jolla, CA (US); Jim-Min Fang, Taipei (TW); Jiun-Jie Shie, Banciao (TW); Yih-Shyun Edmond Cheng, Taipei (TW); Jia-Tsrong Jan, Taipei (TW)

(73) Assignee: Academia Sinica, Taipei (TW)

( * ) Notice: Subject to any disclaimer, the term of this patent is extended or adjusted under 35 U.S.C. 154(b) by 295 days.

(21) Appl. No.: 12/201,955

(22) Filed: Aug. 29, 2008

(65) Prior Publication Data

US 2010/0113397 A1    May 6, 2010

Related U.S. Application Data

(60) Provisional application No. 60/969,491, filed on Aug. 31, 2007, provisional application No. 61/048,507, filed on Apr. 28, 2008.

(51) Int. Cl.
*A61K 31/66* (2006.01)

(52) U.S. Cl. ........................ 514/114; 514/120

(58) Field of Classification Search .............. 514/114, 514/120
See application file for complete search history.

(56) References Cited

U.S. PATENT DOCUMENTS

| 5,763,483 A | 6/1998 | Bischofberger et al. |
| 2008/0009639 A1 | 1/2008 | Radatus et al. |

FOREIGN PATENT DOCUMENTS

| WO | WO 91/16320 AI | 10/1991 |
| WO | WO 92/06691 AI | 4/1992 |
| WO | WO 96/26933 AI | 9/1996 |

OTHER PUBLICATIONS

U.S. Appl. No. 61/052,435, filed May 12, 2008, Tomas Hudlicky.
Streicher H., et al., Building a successful structural motif into sialylmimetics-cyclohexenephosphonate monoesters as pseudosialosides with promising inhibitory properties. Biooroanic & Medicinal Chemistry. Feb. 15, 2006. 14(4). pp. 1047-1057.
Streicher H., et al., Synthesis of functionalized cyclohexenephosphonates and their inhibitory activity towards bacterial sialidases. Tetrahedron. 2002, 58, pp. 7573-7581.
Clinton S. White, et al., A sialic acid-derived phosphonate analog inhibits different strains of influenza virus neuraminidase with different efficiencies. Journal of Molecular Biology. Feb. 3, 1995. 245(5). pp. 623-634.

*Primary Examiner*—Raymond J Henley, III
(74) *Attorney, Agent, or Firm*—Occhiuti Rohlicek & Tsao LLP

(57) ABSTRACT

Novel phosphonate compounds are described. The compounds have activity as neuraminidase inhibitors against wild-type and H274Y mutant of H1N1 and H5N1 viruses. The present disclosure also provides an enantioselective synthetic route to known neuraminidase inhibitors oseltamivir and the anti-flu drug Tamiflu®, as well as novel phosphonate compounds, via D-xylose. Another efficient and flexible synthesis of Tamiflu and the highly potent neuraminidase inhibitor Tamiphosphor was also achieved in 11 steps and >20% overall yields from the readily available fermentation product (1S-cis)-3-bromo-3,5-cyclohexadiene-1,2-diol. Most of the reaction intermediates were obtained as crystals without tedious purification procedures. The key transformations include an initial regio- and stereoselective bromoamidation of a bromoarene cis-dihydrodiol, as well as the final palladium-catalyzed carbonylation and phosphonylation.

26 Claims, 31 Drawing Sheets

(1), Tamiflu,
ethyl ester and as phosphate salt (3) as ammonium salt (3b), diester of 3

(3c), monoester of 3
as ammonium salt (13b), guanidine analog of 3
as ammonium salt (13c), guanidine analog of 3
as ammonium salt

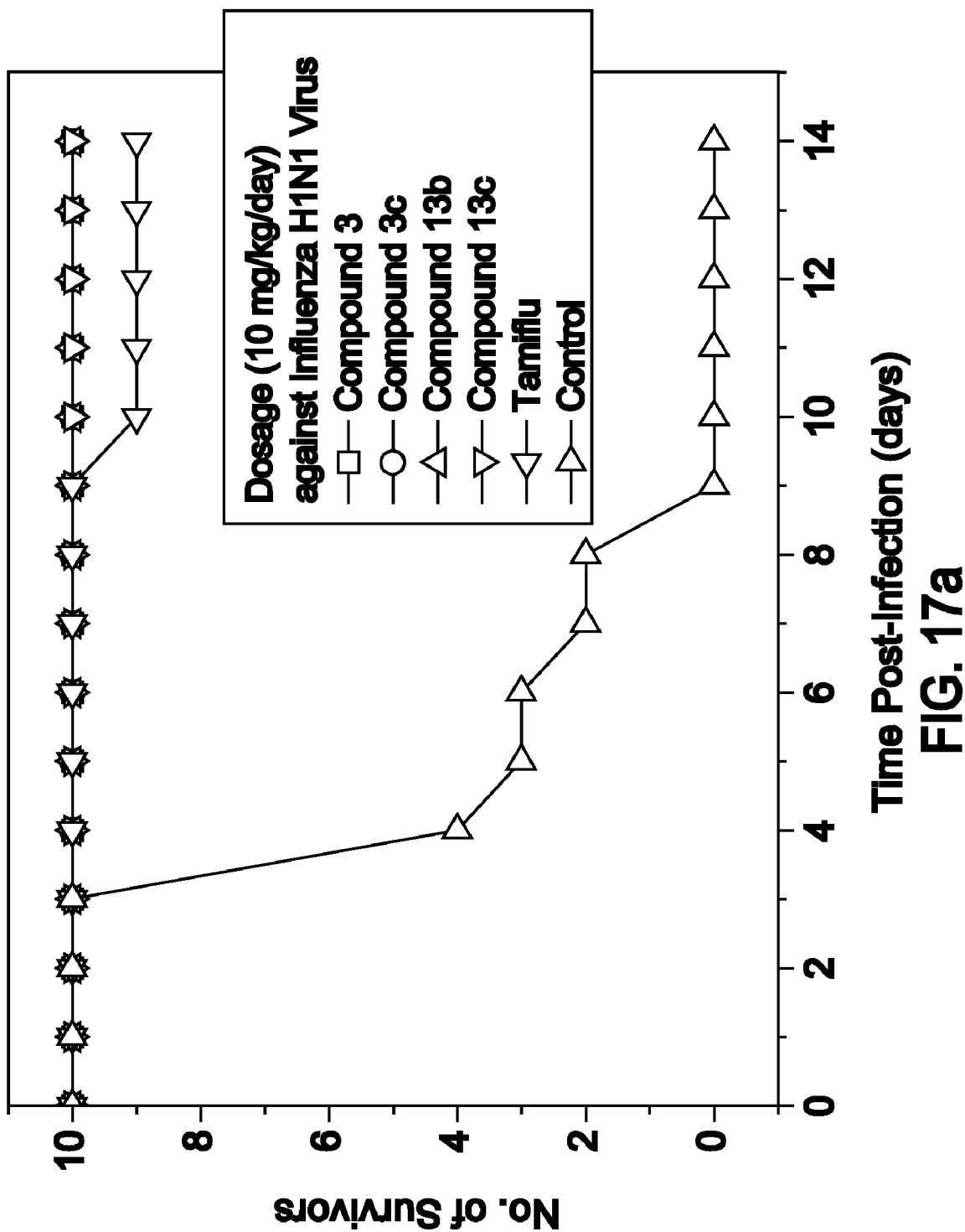

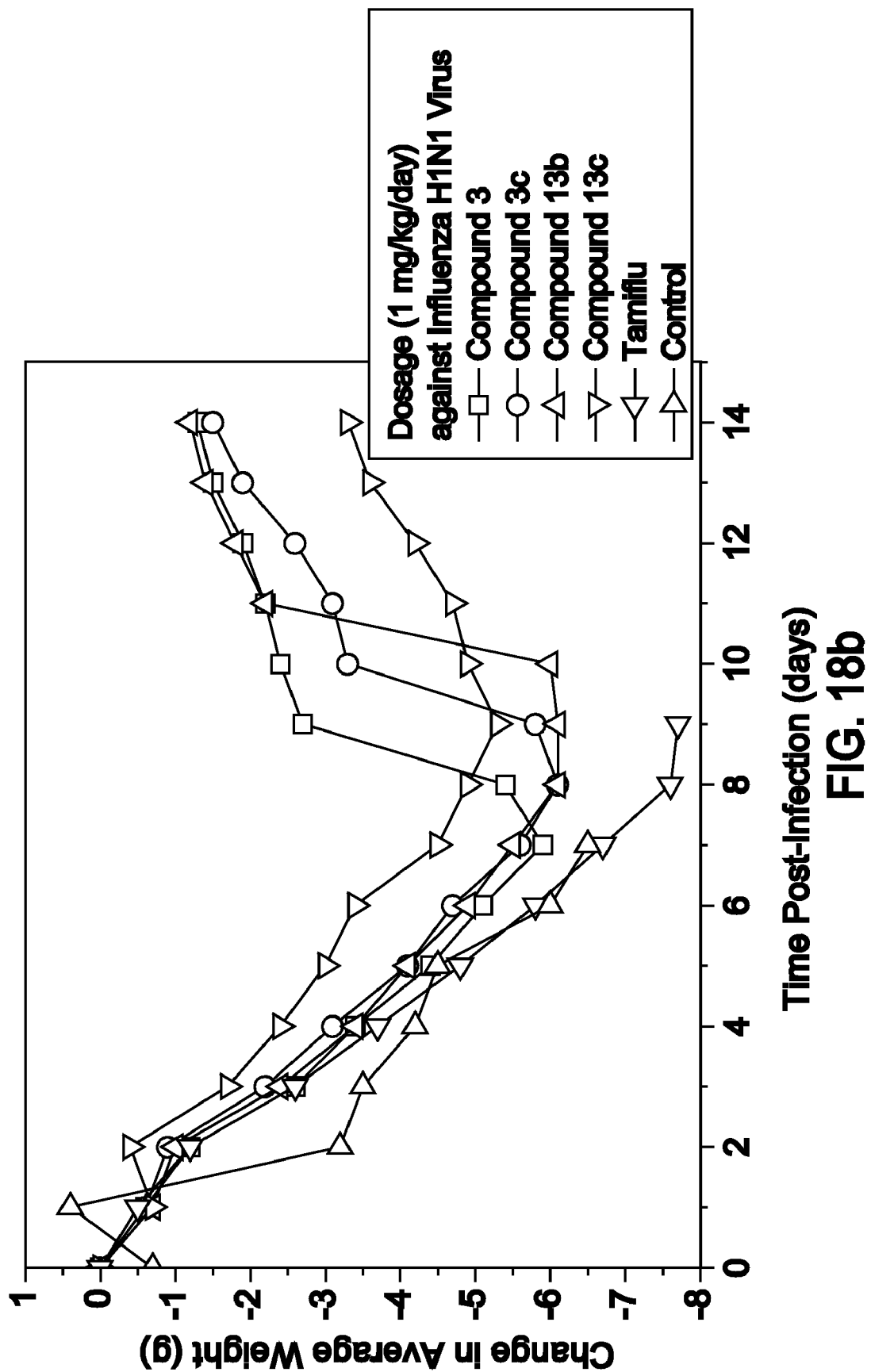

SYNTHESIS OF OSELTAMIVIR CONTAINING PHOSPHONATE CONGENERS WITH ANTI-INFLUENZA ACTIVITY

RELATED APPLICATIONS

This application incorporates by reference and claims the Paris Convention Priority of U.S. Provisional Application Nos. 60/969,491, filed Aug. 31, 2007; and 61/048,507, filed Apr. 28, 2008.

BACKGROUND OF THE INVENTION

1. Field of the Invention

Novel phosphonate compounds are described. The compounds have activity as neuraminidase inhibitors against wild-type and H274Y mutant of H1N1 and H5N1 viruses. The present disclosure also provides two enantioselective synthetic routes to known neuraminidase inhibitors oseltamivir and the anti-flu drug Tamiflu®, as well as novel phosphonate compounds, via D-xylose or bromobenzene.

2. Background

Influenza remains a major health problem for humans and animals. (Kaye and Pringle, *Clin. Infect. Dis.* 2005, 40, 108; and Beigel et al., *N. Engl. J. Med.* 2005, 353, 1374) At present, four drugs are approved for influenza prophylaxis and treatment: amantadine and rimantadine act as the M2 ion channel Mockers, whereas Tamiflu® (the phosphate salt of oseltamivir ethyl ester, Roche Laboratories, Inc.) and Relenza™ (zanamivir, GlaxoWellcome, Inc.) inhibit the activity of neuraminidase (NA). (Moscona, A. N. *Engl. J. Med.* 2005, 353, 1363; Ward et al., *J. Antimicrob. Chemother.* 2005, 55, Suppl. S1, i5; and De Clercq, E. *Nature Rev. Drug Discov.* 2006, 5, 1015.) Recent reports on the drug resistant avian flu infections and the side effects in children receiving Tamiflu® treatments suggest that new chemical identities for neuraminidase inhibitors are needed for the battle against the threat of the pandemic flu. Before a safe and effective vaccine is available to protect the possible pandemic avian flu, neuraminidase inhibitors are one of the few therapeutic approaches available.

The NA inhibitors (NAIs) are designed to have (oxa)cyclohexene scaffolds to mimic the oxonium transition-state in the enzymatic cleavage of sialic acid. (von Itzstein, M. et al. *Nature* 1993, 363, 418; Lew et al., *Curr. Med. Chem.* 2000, 7, 663; and Russell et al., *Nature* 2006, 443, 45). Tamiflu® (i, shown in Scheme 1) is an orally administered anti-influenza drug. (Kim et al., *J. Am. Chem. Soc.* 1997, 119, 681; Rohloff et al., *J. Org. Chem.* 1998, 63, 4545; Karpf and Trussardi, *J. Org. Chem.* 2001, 66, 2044; Harrington et al., *Org. Process Res. Dev.* 2004, 8, 86; Yeung et al., *J. Am. Chem. Soc.* 2006, 128, 6310; Fukuta et al., *J. Am. Chem. Soc.* 2006, 128, 6312; Farina and Brown, *Angew. Chem. Int. Ed.* 2006, 45, 7330; Mita et al., *Org. Lett.* 2007, 9, 259; Yamatsugu et al., *Tetrahedron Lett.* 2007, 48, 1403) On hydrolysis by hepatic esterases, the active carboxylate, oseltamivir (2, also known as GS4071), is exposed to interact with three arginine residues (Arg118, Arg292 and Arg371) in the active site of NA. (von Itzstein, et al., 1993; Lew et al., 2000, and Russell et al., 2006).

The phosphonate group is generally used as a bioisostere of carboxylate in drug design. (White et al., *J. Mol. Biol.* 1995, 245, 623; Streicher et al., *Tetrahedron* 2001, 57, 8851; Streicher, *Bioorg. Med. Chem. Lett.* 2004, 14, 361; Schug and Lindner, W. *Chem. Rev.* 2005, 105, 67; Streicher and Busseb, *Bioorg. Med. Chem.* 2006, 14, 1047). Preliminary molecular docking experiments (FIG. 1) using the known N1 crystal structure (PDB code: 2HU4) (Russell et al., 2006) reveal that the putative phosphonate inhibitor 3a binds strongly with the tri-arginine residues of NA, in addition to other interactions exerted by the $C_3$-pentyloxy, $C_4$-acetamido and $C_5$-amino groups in the binding pocket similar to the NA-oseltamivir complex. In comparison with the carboxylate-guanidinium ion pair, a phosphonate ion exhibits stronger electrostatic interactions with the guanidinium ion. Previously reported methods (including, e.g., Bischofberger et al., U.S. Pat. No. 5,763,483, incorporated herein by reference) for the synthesis of oseltamivir/Tamiflu are not amenable to exchange of the C-1 carboxyl group to a phosphonate group; therefore, a novel approach to the synthesis of both known and novel neuraminidase inhibitors is desirable.

BRIEF SUMMARY OF THE INVENTION

Novel phosphonate compounds are described. The compounds have activity as neuraminidase inhibitors against wild-type and H274Y mutant of H1N1 and H5N1 viruses. The present disclosure also provides an enantioselective synthetic route to known neuraminidase inhibitors oseltamivir and the anti-flu drug Tamiflu®, as well as novel phosphonate compounds, via D-xylose. Another efficient and flexible synthesis of Tamiflu and the highly potent neuraminidase inhibitor Tamiphosphor was also achieved in 11 steps and >20% overall yields from the readily available fermentation product (1S-cis)-3-bromo-3,5-cyclohexadiene-1,2-diol. Most of the reaction intermediates were obtained as crystals without tedious purification procedures. The key transformations include an initial regio- and stereoselective bromoamidation of a bromoarene cis-dihydrodiol, as well as the final palladium-catalyzed carbonylation and phosphonylation.

According to a feature of the present disclosure, a composition is disclosed comprising a therapeutically effective amount of formula I (I)

and a pharmaceutical carrier, where A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, and calcium cation, zinc cation; and where $R_1$ is $NH_2$, $NH_3^+H_2PO_4^-$, or $NH(C=NH)NH_2$.

According to a feature of the present disclosure, a composition is disclosed comprising a therapeutically effective amount of at least one of:

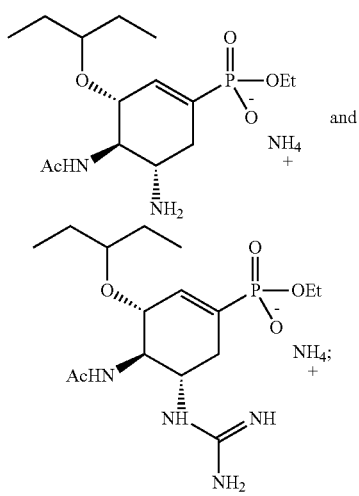

and a pharmaceutical carrier.

According to a feature of the present disclosure, a method is disclosed comprising making a composition of formula I according to least one of the schemes of FIGS. 3-5:

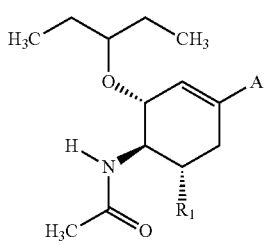
(I)

wherein A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, and calcium cation, zinc cation; and where $R_1$ is $NH_2$, $NH_3{}^+H_2PO_4{}^-$, or $NH(C{=}NH)NH_2$. Products by this process are similarly contemplated.

According to a feature of the present disclosure, a method is disclosed comprising providing a therapeutically effective amount of a composition having Formula I:

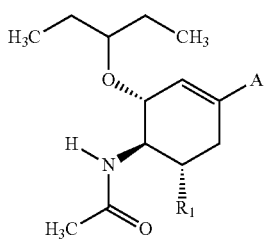
(I)

where the composition is designed to be administered to an organism to inhibit the activity of neuraminidase, where A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3{}^+H_2PO_4{}^-$, or $NH(C{=}NH)NH_2$.

According to a feature of the present disclosure, a method is disclosed comprising providing a composition having therapeutically effective amount of at least one of:

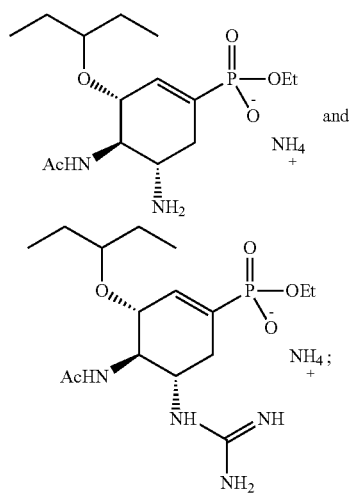

wherein the composition is designed to be administered to an organism to inhibit the activity of neuraminidase.

In one implementation, the invention provides a compound of formula (I):

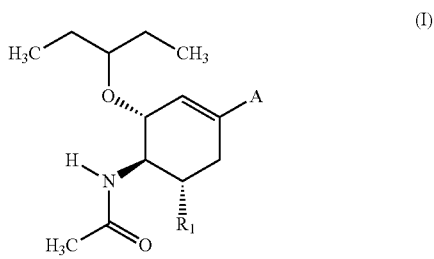
(I)

wherein A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanolammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3{}^+H_2PO_4{}^+$, or $NH(C{=}NH)NH_2$.

In a specific aspect, the compound is:

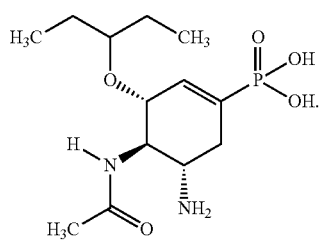
(3a)

In another specific aspect, the compound is:

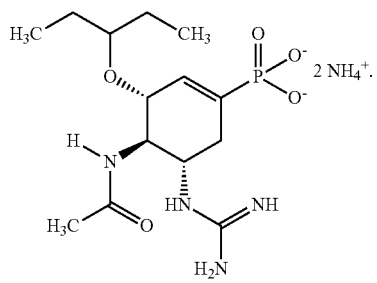
(13b)

In a further specific aspect, the compound is:

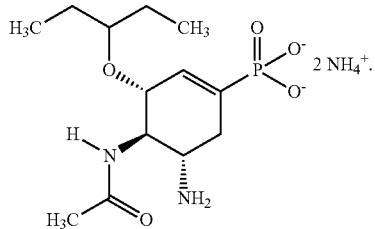
(3)

In another specific aspect, the compound is:

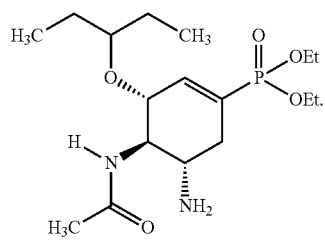
(3b)

In another specific aspect, the compound is:

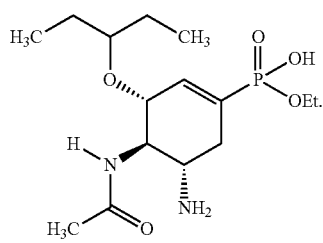

Another implementation of the present disclosure provides a compound of the formula:

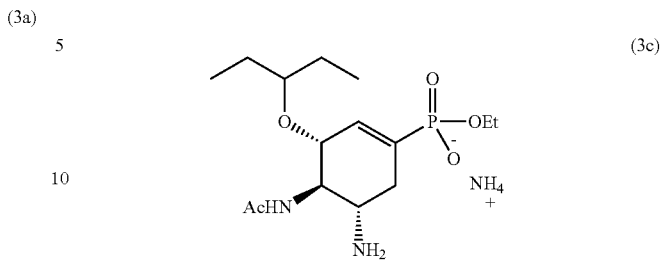
(3c)

Another of the present disclosure provides a compound of the formula:

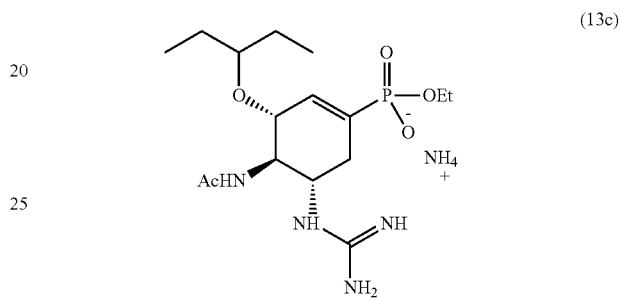
(13c)

In one implementation, the invention provides a composition comprising a compound of any one of compounds (I), wherein A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanolammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3+H2PO_4^-$, or $NH(C=NH)NH_2$; 3, 3a, 3b, 13a, and 13 b, and a pharmaceutically acceptable carrier.

In another implementation, the invention provides a process for preparing a compound of the formula (I):

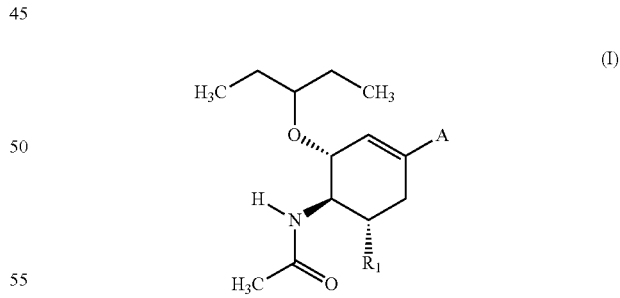
(I)

wherein A is $CO_2R$, or PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3+H2PO_4-$, or $NH(C=NH)NH_2$; the process comprising:

(a) utilizing D-xylose as a chiral precursor to prepare an intermediate compound (7):

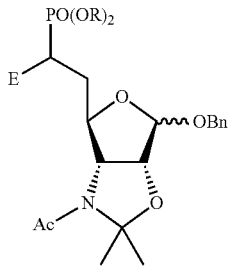

(7)

wherein E is $CO_2R$ or PO(OR)(OR') where R and R' are independently selected from C1-C6 alkyl and aryl;

(b) treating intermediate compound (7) to perform an intramolecular Horner-Wadsworth-Emmons reaction to form intermediate compound (8):

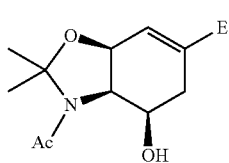

(8)

wherein E is $CO_2R$ or PO(OR)(OR') where R and R' are independently selected from C1-C6 alkyl and aryl;

(c) treating intermediate (8) with diphenylphosphoryl azide to substitute the hydroxy group with an azido group with inversion of configuration to form intermediate (9):

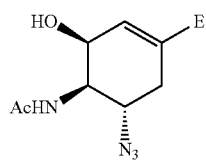

(9)

wherein E is $CO_2R$ or PO(OR)(OR') where R and R' are independently selected from C1-C6 alkyl and aryl;

(d) treating intermediate compound (9) with $Tf_2O$, a base and a crown ether to invert the hydroxy group to form intermediate compound (10):

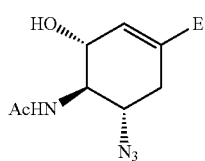

(10)

wherein E is $CO_2R$ or PO(OR)(OR') where R and R' are independently selected from C1-C6 alkyl and aryl; and (e) treating intermediate (10) to form a compound of formula (I).

Another implementation of the invention provides a method of inhibiting the activity of a neuraminidase comprising contacting said neuraminidase with of any one of compounds (I), wherein A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanolammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3+H2PO_4-$, or $NH(C=NH)NH_2$; 3, 3a, 3b, 13a, and 13 b.

In one aspect, the neuraminidase is an influenza neuraminidase in vivo. In another aspect, the neuraminidase is an influenza neuraminidase in vitro.

In another implementation, the invention provides a method for the treatment of influenza in a patient in need thereof, the method comprising administering to said patient a composition comprising a therapeutically effective amount of any one of compounds (I); wherein A is PO(OR)(OR'), where R and R' are independently selected from H, C1-C6 alkyl, aryl and X, where X is a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, and calcium cation, zinc cation; and $R_1$ is $NH_2$, $NH_3+H2PO_4-$, or $NH(C=NH)NH_2$; 3, 3a, 3b, 13a, and 13b. In one aspect, the composition further comprises a pharmaceutically-acceptable carrier.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which.

DETAILED DESCRIPTION

In the following detailed description of implementations of the present disclosure, reference is made to the accompanying drawings in which like references indicate similar elements, and in which is shown by way of illustration specific implementations in which the present disclosure may be practiced. These implementations are described in sufficient detail to enable those skilled in the art to practice the present disclosure, and it is to be understood that other implementations may be utilized and that logical, mechanical, electrical, functional, compositional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

This application incorporates by reference Appendix A of the present disclosure.

The present disclosure provides a novel synthetic route to the known neuraminidase inhibitors oseltamivir and the anti-flu drug Tamiflu®, as well as novel phosphonate congers. D-xylose was utilized as a chiral precursor for the synthesis of known and novel active neuraminidase inhibitors. Novel phosphonate congers exhibit better anti-flu activities than Tamiflu® by inhibiting the neuraminidases of the wild-type and H274Y mutant of H1N1 and H5N1 viruses.

The current industrial synthesis of Tamiflu relies on the naturally occurring shikimic acid as a starting material. However, the availability of shikimic acid with consistent purity may cause a problem. This synthesis also has a drawback in manipulation of the explosive azide reagent and intermediates. Several new synthetic methods of Tamiflu embarked on the shikimic acid-independent approaches. To establish the core structure of cyclohexenecarboxylates in Tamiflu, various types of Diels-Alder reactions have been applied. For example, the Diels-Alder reaction between furan and acrylate has been preformed, followed by enzymatic resolution, to obtain the chiral intermediate for the Tamiflu synthesis. Similarly, the Diels-Alder reaction of 1-trimethylsilyloxy-1,3-butadiene with fumaryl chloride is utilized to construct the core structure; however, separation of the racemic mixture of a key intermediate by chiral HPLC is required in this synthetic sequence. Alternatively, the catalytic enantioselective Diels-Alder reactions afford the required chiral cyclohexenecarboxylates for Tamiflu synthesis.

Figure 3:
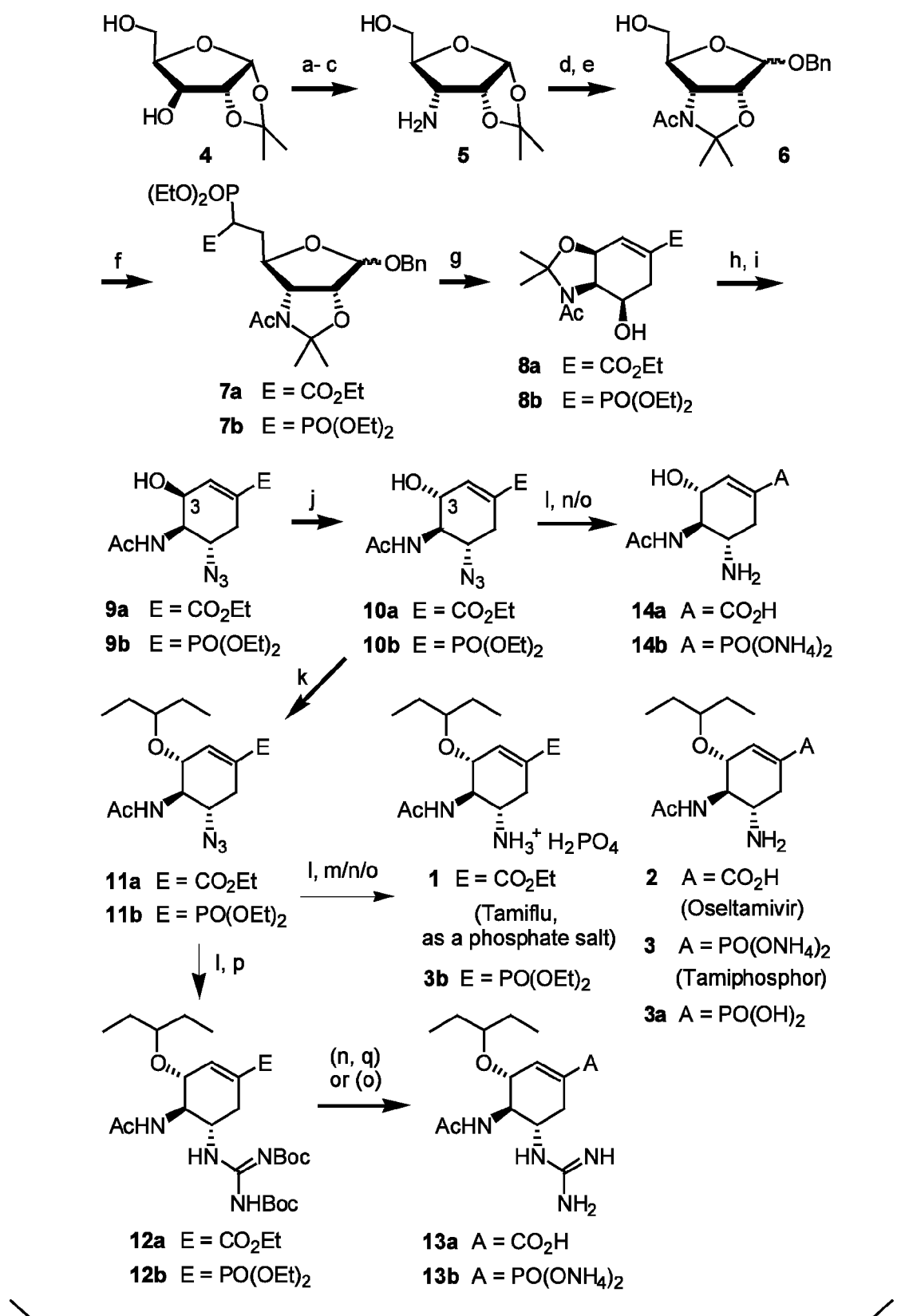
FIG. 3 shows a novel route to the synthesis of Tamiflu® 1, oseltamivir 2, the guanidine analog 13a, and the phosphonate congeners 3, 3b and 13b.

In one implementation, the invention provides a novel synthetic method to enantioselective synthesis of Tamiflu, oseltamivir, various phosphonate congers and the guanidine analogs with reasonably high yields (5.2-13.5%). The synthetic route is shown in FIG. 3 (Scheme 1). An intramolecular Horner-Wadsworth-Emmons reaction was carried out to furnish the cyclohexene carboxylate 8a and phosphonate 8b. On treatment with diphenylphosphoryl azide according to Mitsunobu's method, the hydroxyl group in 8a/8b was successfully substituted by an azido group with inversed configuration. In one aspect, the hazardous reagent of sodium azide was avoided in this procedure. In a preferred aspect, the synthetic scheme allows late functionalization, which makes it attractive from a medicinal chemistry point of view.

The novel synthetic scheme is shown in FIG. 3. Reagents and steps described in FIG. 3, are as follows: (a) $Me_3CCOCl$, pyridine, 0° C., 8 h; 89%. (b) PDC, $Ac_2O$, reflux, 1.5 h; $HONH_2$—HCl, pyridine, 60° C., 24 h; 82%. (c) $LiAlH_4$, THF, 0° C., then reflux 1.5 h; 88%. (d) $Ac_2O$, pyridine, 25° C., 3 h; HCl/1,4-dioxane (4 M), BnOH, toluene, 0-25° C., 24 h; 85%. (e) 2,2'-dimethoxypropane, toluene, cat. p-TsOH, 80° C., 4 h; 90%. ($Tf_2O$, pyridine, $CH_2Cl_2$, −15° C., 2 h; $EtO_2CCH_2PO(OEt)_2$ or $H_2C[PO(OEt)_2]_2$, NaH, cat. 15-crown-5, DMF, 25° C., 24 h; 80% for 7a and 73% for 7b. (g) H2, Pd/C, EtOH, 25° C., 24 h; NaH, THF, 25° C., 1 h, 83% for 8a; or NaOEt, EtOH, 25° C., 5 h, 80% for 8b. (h) $(PhO)_2PON_3$, (i-Pr)N=C=N(i-Pr), $PPh_3$, THF, 25° C., 48 h. (i) HCl, EtOH, reflux, 1 h; 83% for 9a and 74% for 9b. (j) $Tf_2O$, pyridine, $CH_2Cl_2$, −15 to −10° C., 2 h; $KNO_2$, 18-crown-6, DMF, 40° C., 24 h; 70% for 10a and 71% for 10b. (k) $Cl_3CC(=NH)OCHEt_2$, $CF_3SO_3H$, $CH_2Cl_2$, 25° C., 24 h; 78% for 11a and 82% for 11b. (l) $H_2$, Lindlar catalyst, EtOH, 25° C., 16 h; 85% for 3b. (m) $H_3PO_4$, EtOH, 40° C., 1 h; 91% for 1. (n) KOH, $THF/H_2O$, 0-25° C., 1 h; 88% for 2 and 81% for 14a. (o) TMSBr, $CHCl_3$, 25° C., 24 h; aqueous $NH_4HCO_3$, lyophilization; 85% for 3 (as the ammonium salt), 72% for 13b and 75% for 14b. (p) N,N'-bis(tert-butoxycarbonyl)thiourea, $HgCl_2$, $Et_3N$, DMF, 0-25° C., 10-16 h; 78% for 12a and 58% for 12b. (q) TFA, $CH_2Cl_2$, 0° C., 1 h; 88% for 13a. Reagents, reaction conditions and yields for each step are described in greater detail in the experimental section below.

In another approach, a meso-aziridine derivative of 1,4-cyclohexadiene is prepared and subject to catalytic asymmetric ring-opening reaction with trimethylsilyl azide, serving as the platform methodology for the synthesis of Tamiflu. Ru-Al$_2$O$_3$ catalyzed hydrogenation of substituted isophthalic diester to provide the cyclohexane core structure with all the substituents and diester on cis-disposition. The meso-diester was then enzymatically hydrolyzed to an optically active mono-acid, which serves as the key intermediate for the synthesis of Tamiflu. The synthesis of Tamiflu was demonstrated by starting with amination of a chiral cationic iron complex of cyclohexadienecarboxylate, which is obtained by HPLC separation of the diastereomers derived with (1R,2S)-2-phenylcyclohexanol. Finally, a palladium-catalyzed asymmetric allylic amination of 5-oxa-bicyclo[3.2.1]hexen-4-one was demonstrated as a key step in the synthesis of Tamiflu.

The inventors discovered that the synthesis of Tamiflu and Tamiphosphor using D-xylose as an inexpensive starting material. The cyclohexene core of the target compounds is constructed by an intramolecular Horner-Wadsworth-Emmons reaction. Though this flexible synthetic method provides both Tamiflu and Tamiphosphor in reasonable overall yields (5-13%), the lengthy pathway (18-19 reaction steps) is not ideal for the large-scale synthesis. A more concise and practical synthetic route to Tamiflu and Tamiphosphor was delineated as shown in FIG. 4.

In this procedure, the starting material of enantiopure bromoarene cis-1,2-dihydrodiol (17) is commercially available, and easily produced by microbial oxidation of bromobenzene on large scales. Due to their unique combinations of functionality, the haloarene cis-dihydrodiols have been successfully applied to the synthesis of various natural products and the related molecules. In addition, the bromine atom can be transformed into various functional groups, including carboxylate and phosphonate, at a late stage of the synthetic pathway. Thus, this synthetic scheme is versatile in using the common intermediates, e.g., 26 and 29, as the pivotal points to Tamiflu, Tamiphosphor and other derivatives. Such late functionalization is particularly appealing from a medicinal chemistry point of view.

Figure 4:
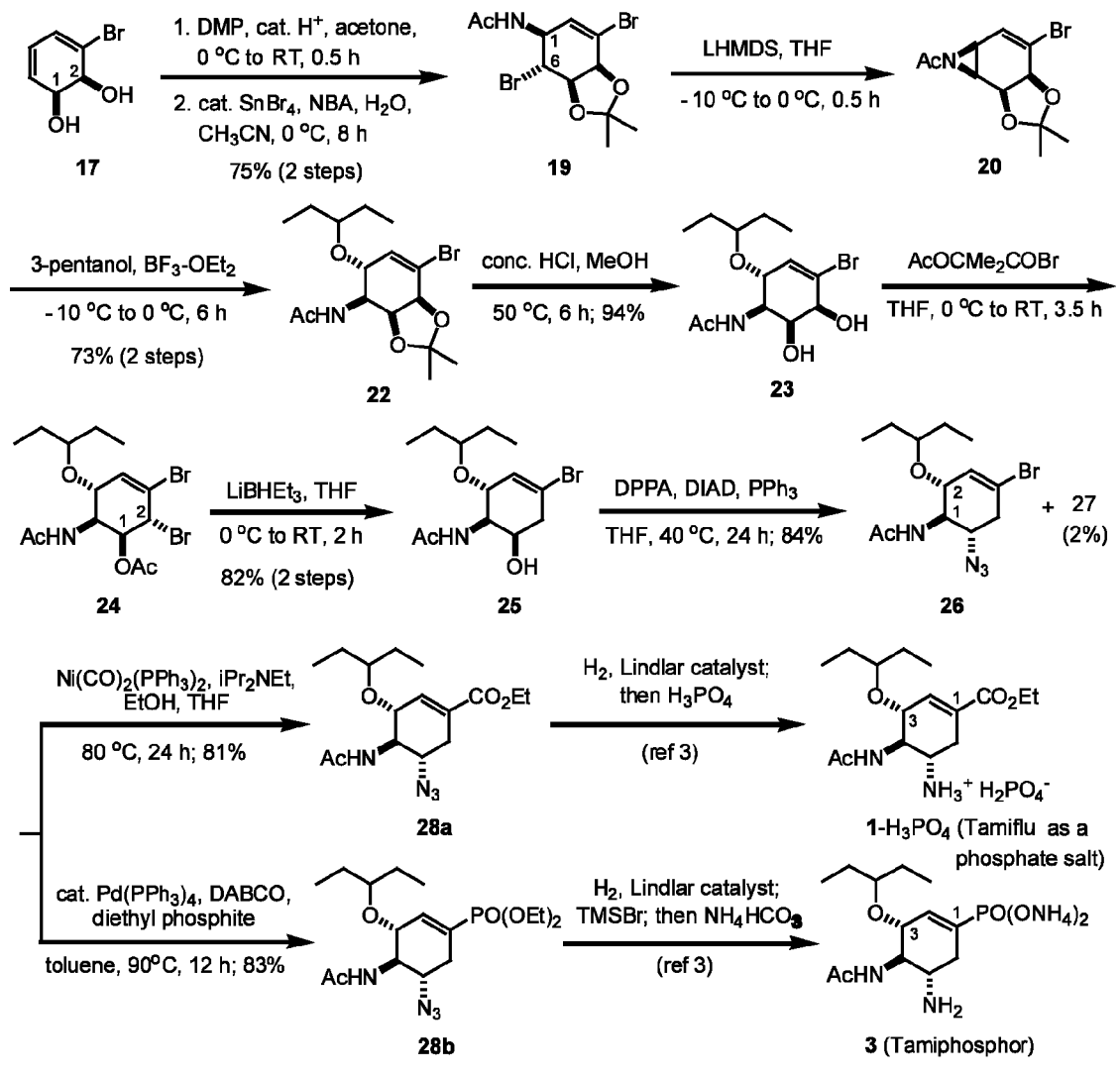
FIG. 4 shows a novel route to the synthesis of Tamiflu® 1 and the phosphonate congener Tamiphosphor 3.

Based on this synthetic plan, the acetonide of (1S,2S)-cis-diol 17 was subject to a SnBr$_4$-catalyzed bromoacetamidation reaction with N-bromoacetamide (NBA) in CH$_3$CN at 0° C., giving bromoamide 19 in the regio- and stereoselective manner as shown in FIG. 4. The structure of 19 was confirmed by an X-ray diffraction analysis (see Examples 31 et seq.). This reaction likely proceeded by formation of a bromonium ion on the less hindered face, followed by a selective back-side attack of acetamide at the allylic C-5 position. In the presence of LHMDS (1.1 equiv), bromoamide 19 was converted to aziridine 20, which underwent a BF$_3$-mediated ring-opening reaction with 3-pentanol to give compound 22 in 73% yield. After deprotection, the cis-diol 23 was treated with α-acetoxyisobutyryl bromide to afford the corresponding trans-2-bromocyclohexyl acetate 24. By analogy to the precedented examples, this reaction might involve an intermediate formation of acetoxonium ion, and a backside attack of bromide ion at the allylic C2 position. The reaction of 24 with 3 equiv of LiBHEt$_3$ (Super-Hydride®) afforded a clean product 25 in 82% yield (from 23) by simultaneous reduction of the acetyl group and the bromine atom at the C1 and C2 positions. On treatment with diphenylphosphoryl azide (DPPA) according to Mitsunobu's method, the hydroxyl group in 25 was successfully substituted by an azido group with the inversed configuration, giving 26 in 84% yield. A small amount (2%) of diene 27 was also found as the side product generated by elimination of a water molecule. The pivotal compound 26 was subject to organometallic coupling reactions to incorporate the desired carboxyl and phosphonyl groups. Thus, the reaction of 26 with Ni(CO)$_2$(PPh$_3$)$_2$ in the presence of EtOH gave the ethyl ester 28a in 81% yield. On the other hand, phosphonylation of 26 with diethyl phosphite was achieved by the catalysis of Pd(PPh$_3$)$_4$ to afford the phosphonate 28b in 83% yield. After reduction of the azido group in 28a and 28b to amine, Tamiflu and Tamiphosphor were synthesized according to our previously reported procedures.

Figure 5:
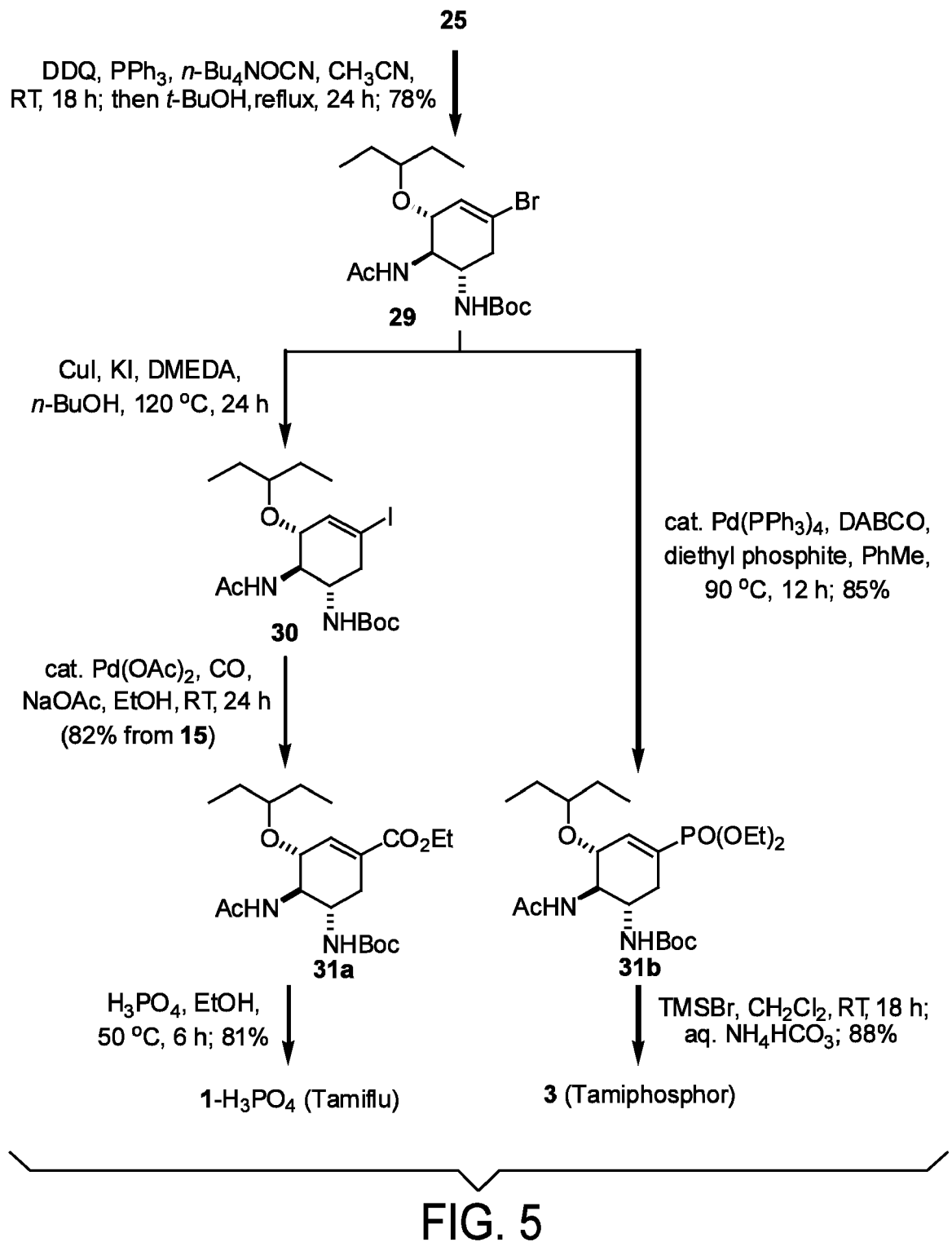
FIG. 5 shows a novel route to the synthesis of Tamiflu® 1 and the phosphonate congener Tamiphosphor 3.

The above-mentioned synthetic method was further improved by an azide-free process. We found that tetrabutylammonium cyanate was a good source of the amine functionality as shown in FIG. 5. Alcohol 25 reacted with Bu$_4$NOCN/PPh$_3$/DDQ to give an isocyanate intermediate, which was subsequently treated with t-BuOH to give carbamate 29 in 78% yield, as shown if FIG. 5. A Pd-catalyzed coupling reaction with diethyl phosphite was carried out, forming phosphonate 31b, and Tamiphosphor was synthesized by a concurrent removal of the Boc and ethyl groups with TMSBr in mild conditions. To avoid using a stoichiometric amount of toxic Ni(CO)$_2$(PPh$_3$)$_2$, the Pd-catalyzed carbonylation of 29 was attempted without success. Alternatively, bromide 29 was converted to the more reactive iodide analog 30, and the Pd-catalyzed carbonylation was realized in a high yield, giving the carboxylate 31a. Finally, 31a was treated with H$_3$PO$_4$ to give Tamiflu, via cleavage of the Boc group and formation of the phosphate salt in one-pot operation.

In conclusion, Tamiflu and Tamiphosphor are synthesized in 21-26% overall yields via an 11-step reaction sequence using the readily available material of bromoarene cis-diol 19, which can be supplied from the microbial oxidation of bromobenzene. All reactions are handled without using potentially hazardous intermediates or toxic reagents. Because most of the reactions occur in a regio- and stereoselective fashion to give crystalline products, the isolation procedure is relatively simple and cost effective. Though only gram-scale synthesis is demonstrated in this study, the large-scale synthesis of Tamiflu and Tamiphosphor is promising for the development of anti-flu drugs.

Figure 7:
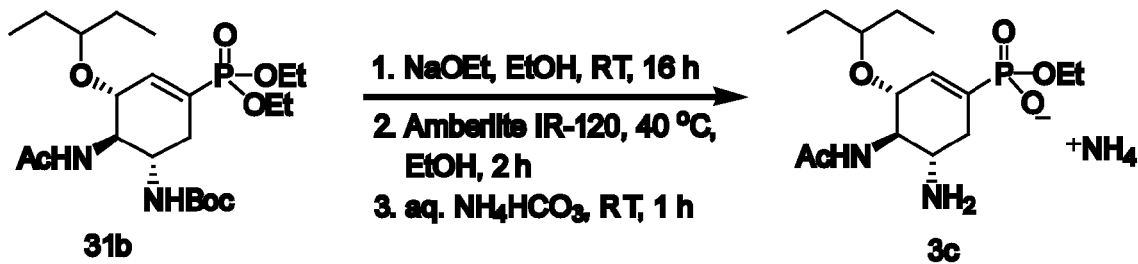
FIG. 7 shows a novel route to the synthesis of phosphonate congener 3c.
Figure 8:
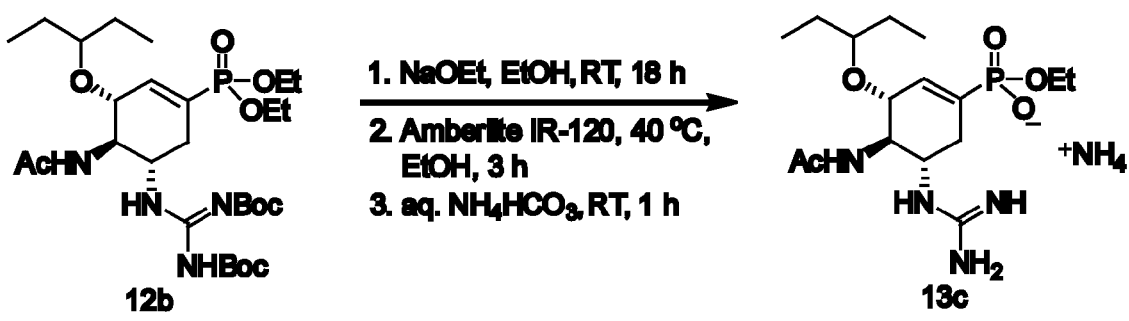
FIG. 8 shows a novel route to the synthesis of phosphonate congener 13c.
Figure 9A:
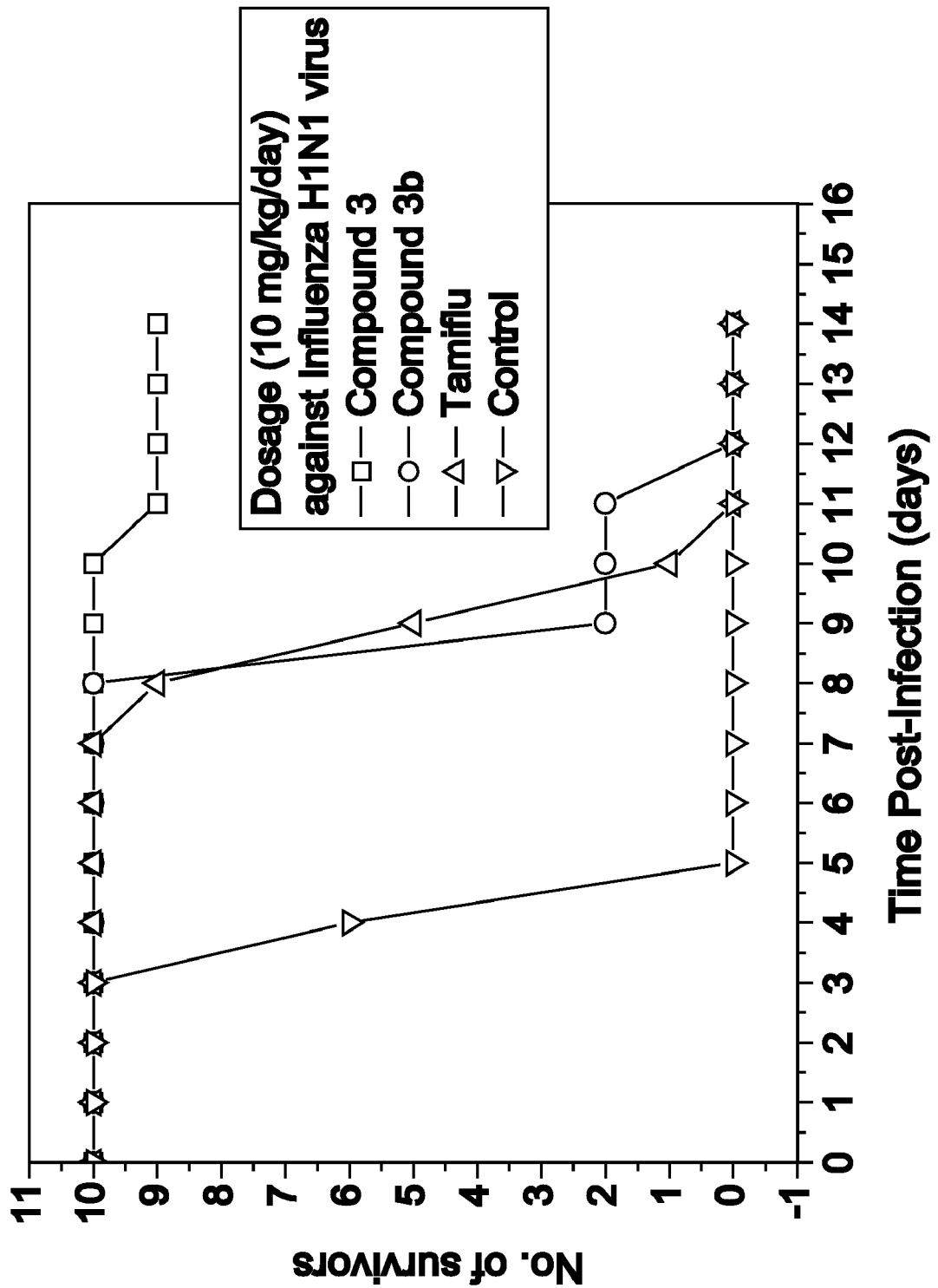
FIG. 9 shows survival rate (panel a) and change of average body weight (panel b) of mice inoculated with 10 $MLD_{50}$ of A/WSN/33 (H1N1) influenza virus and treated at a drug dosage of 10 mg/kg/day.
Figure 9B:
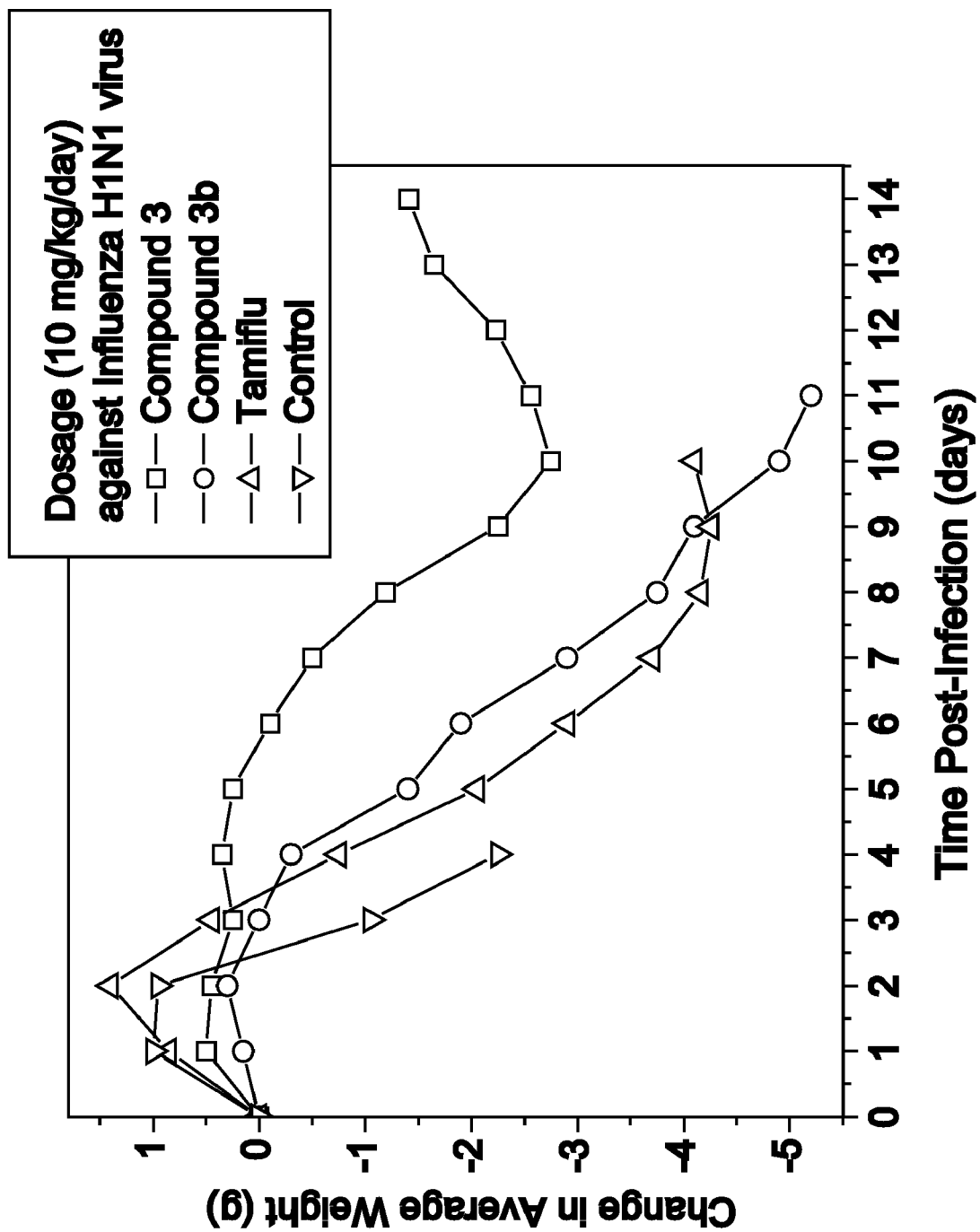
Figure 10A:
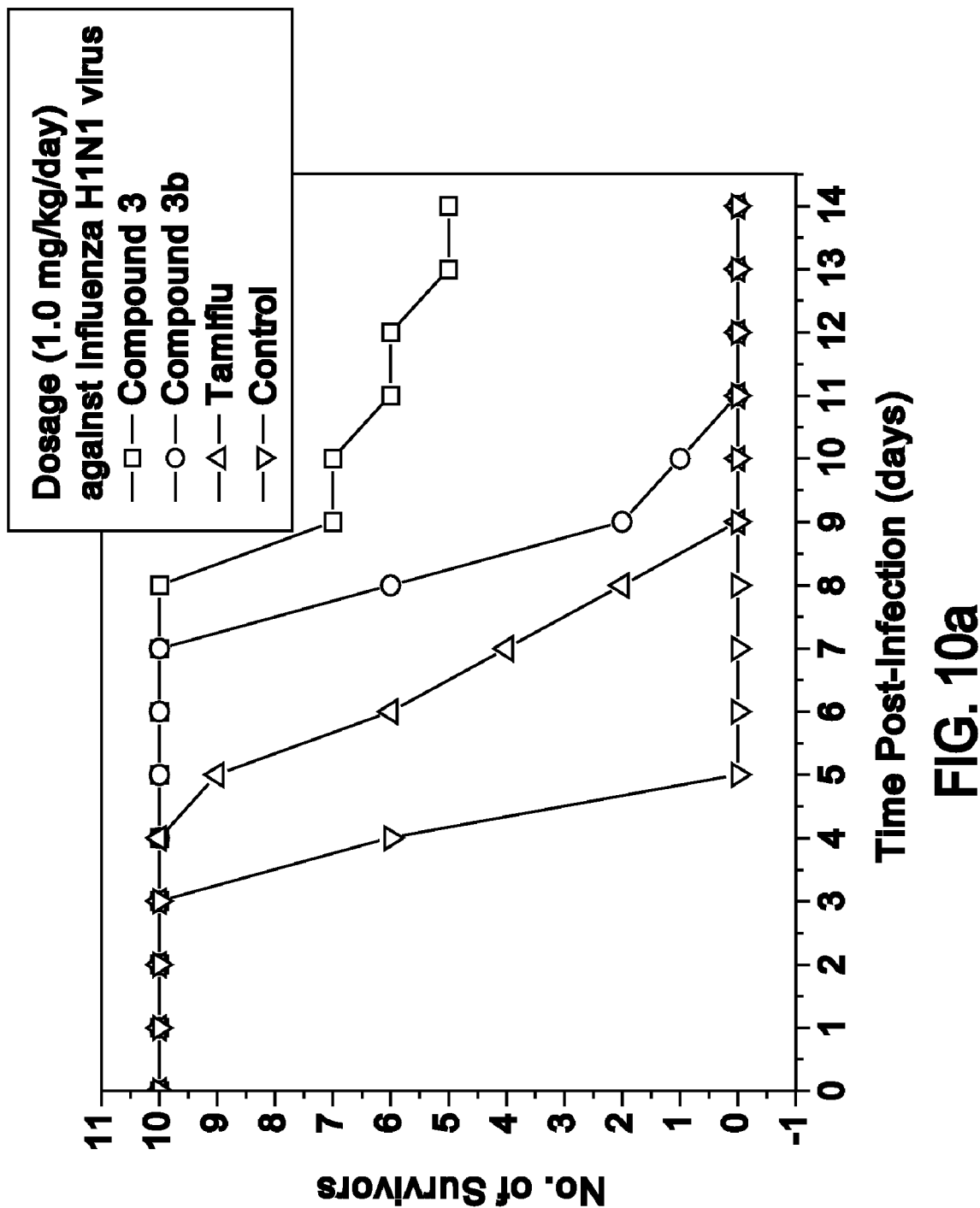
FIG. 10 shows survival rate (panel a) and change of average body weight (panel b) of mice inoculated with 10 $MLD_{50}$ of A/WSN/33 (H1N1) influenza virus and treated at a drug dosage of 1 mg/kg/day.
Figure 10B:
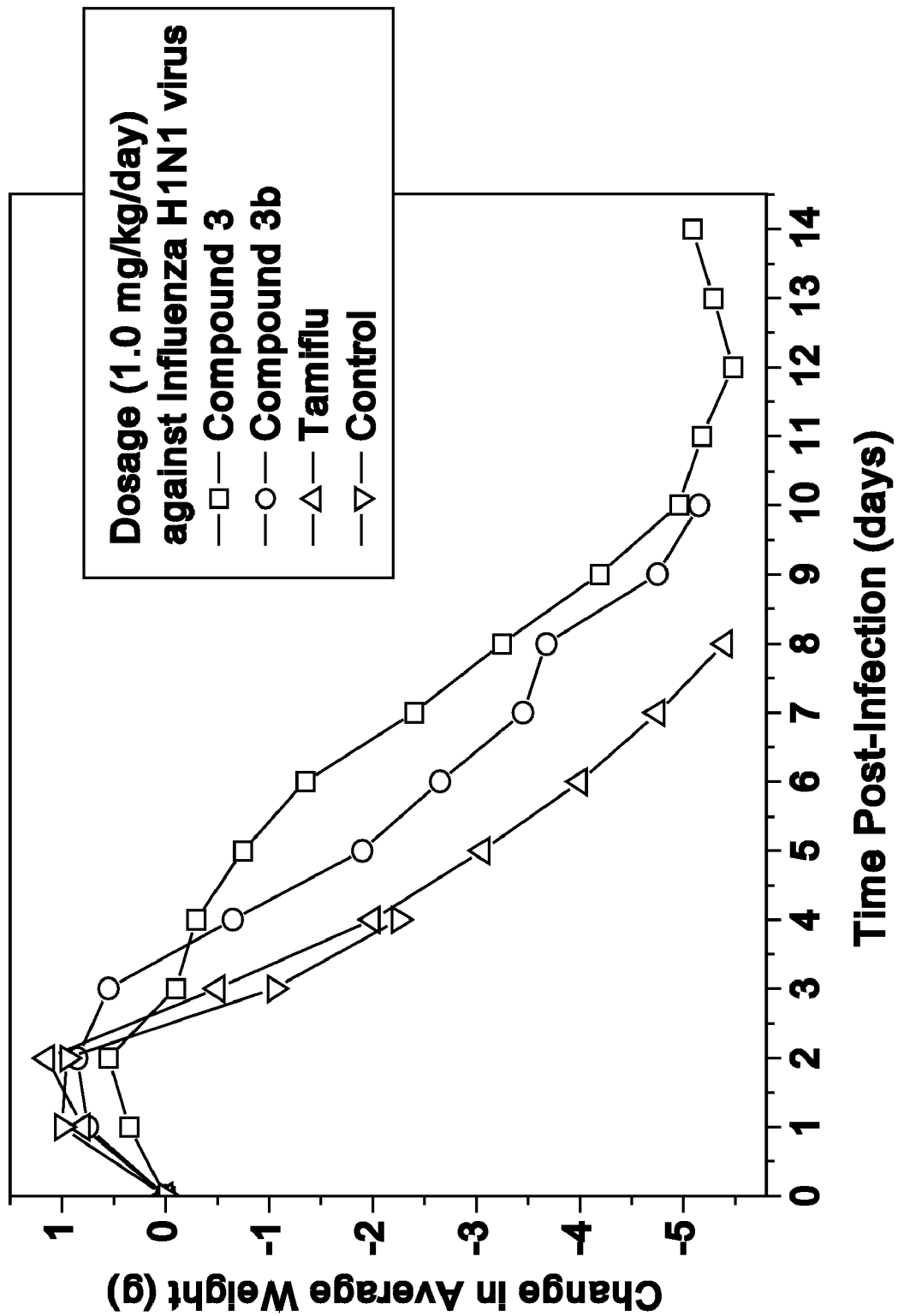
Figure 11A:
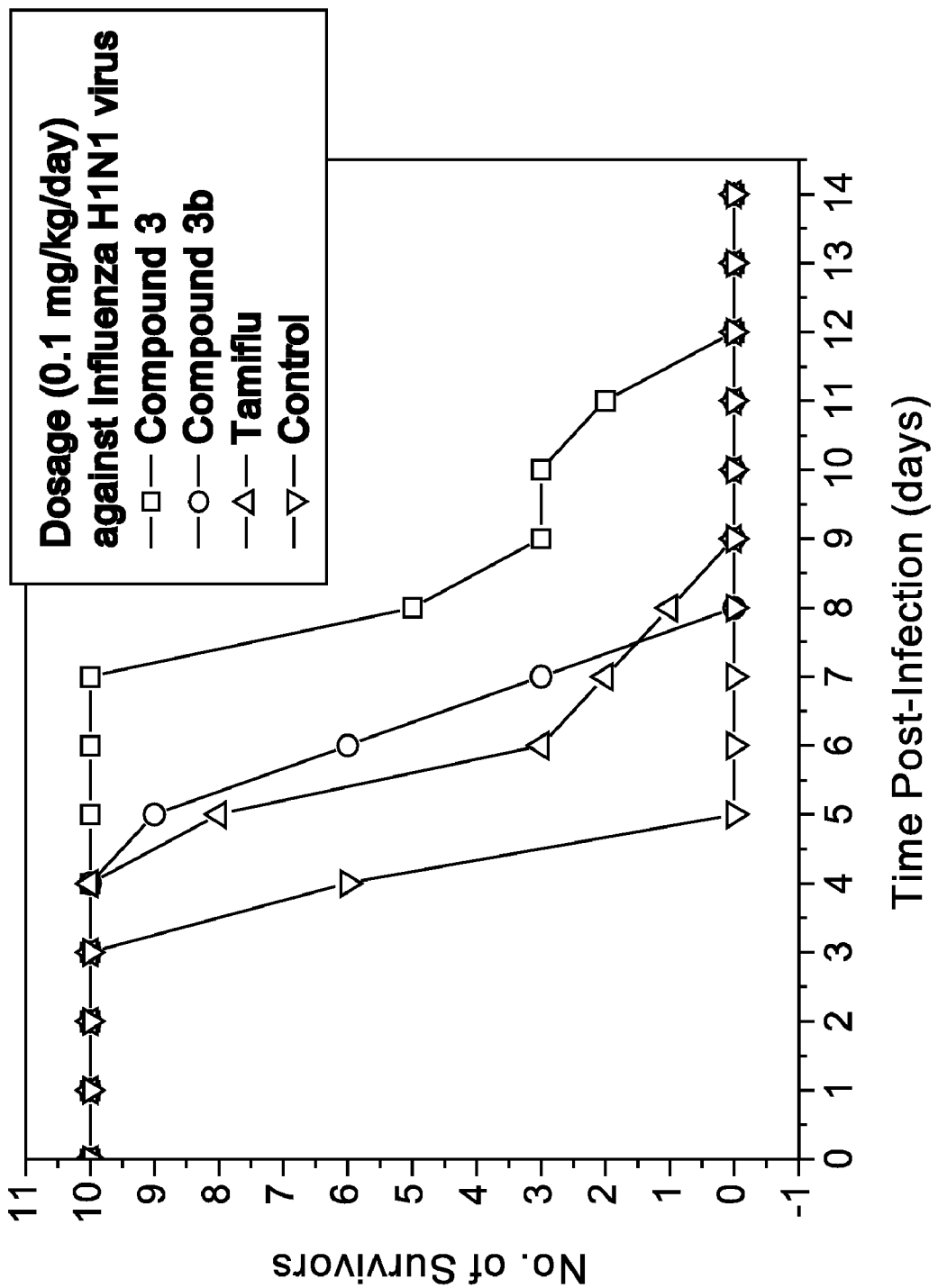
FIG. 11 shows survival rate (panel a) and change of average body weight (panel b) of mice inoculated with 10 $MLD_{50}$ of A/WSN/33 (H1N1) influenza virus and treated at a drug dosage of 0.1 mg/kg/day.
Figure 11B:
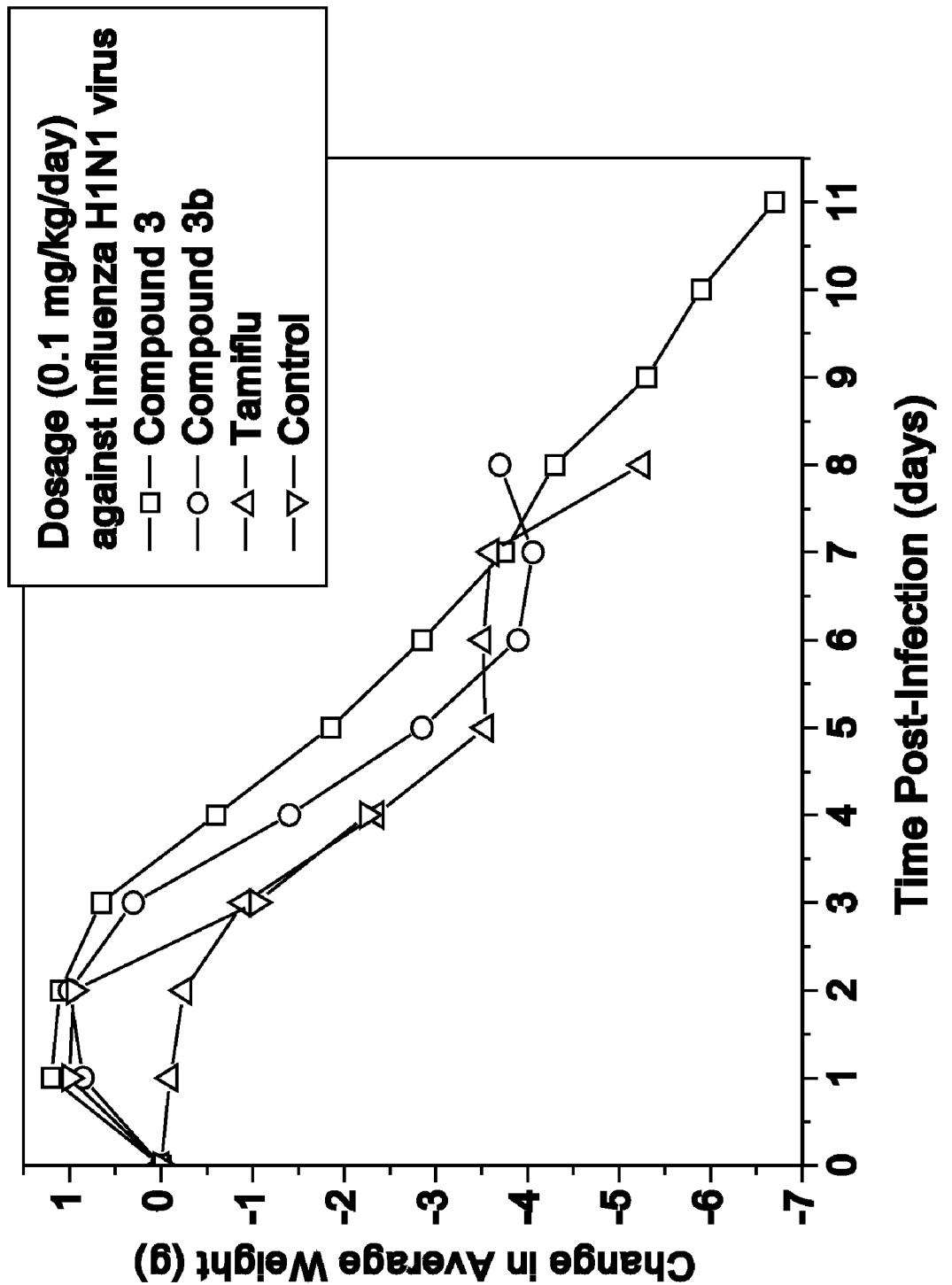
Figure 12A:
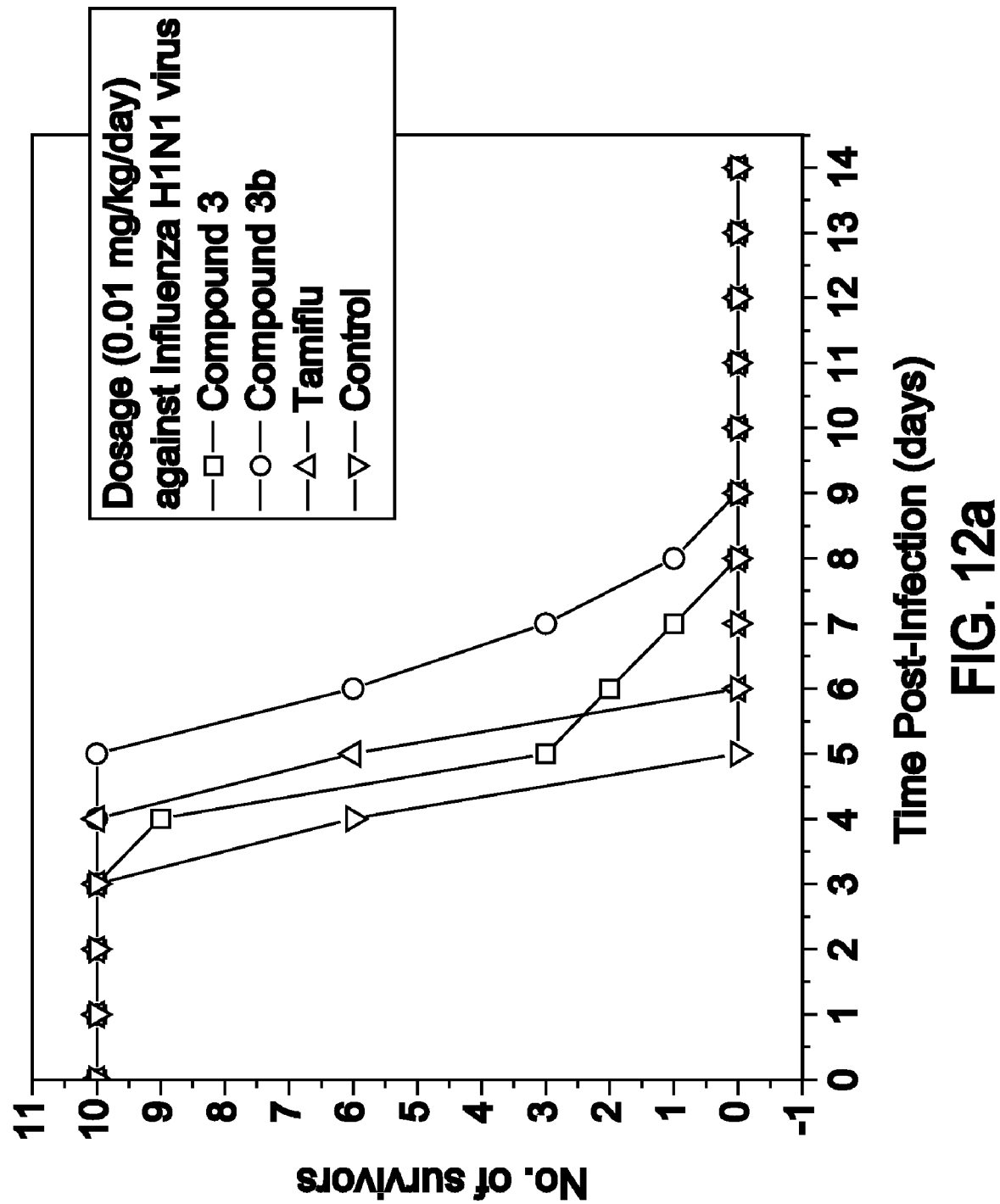
FIG. 12 shows survival rate (panel a) and change of average body weight (panel b) of mice inoculated with 10 $MLD_{50}$ of A/WSN/33 (H1N1) influenza virus and treated at a drug dosage of 0.01 mg/kg/day.
Figure 12B:
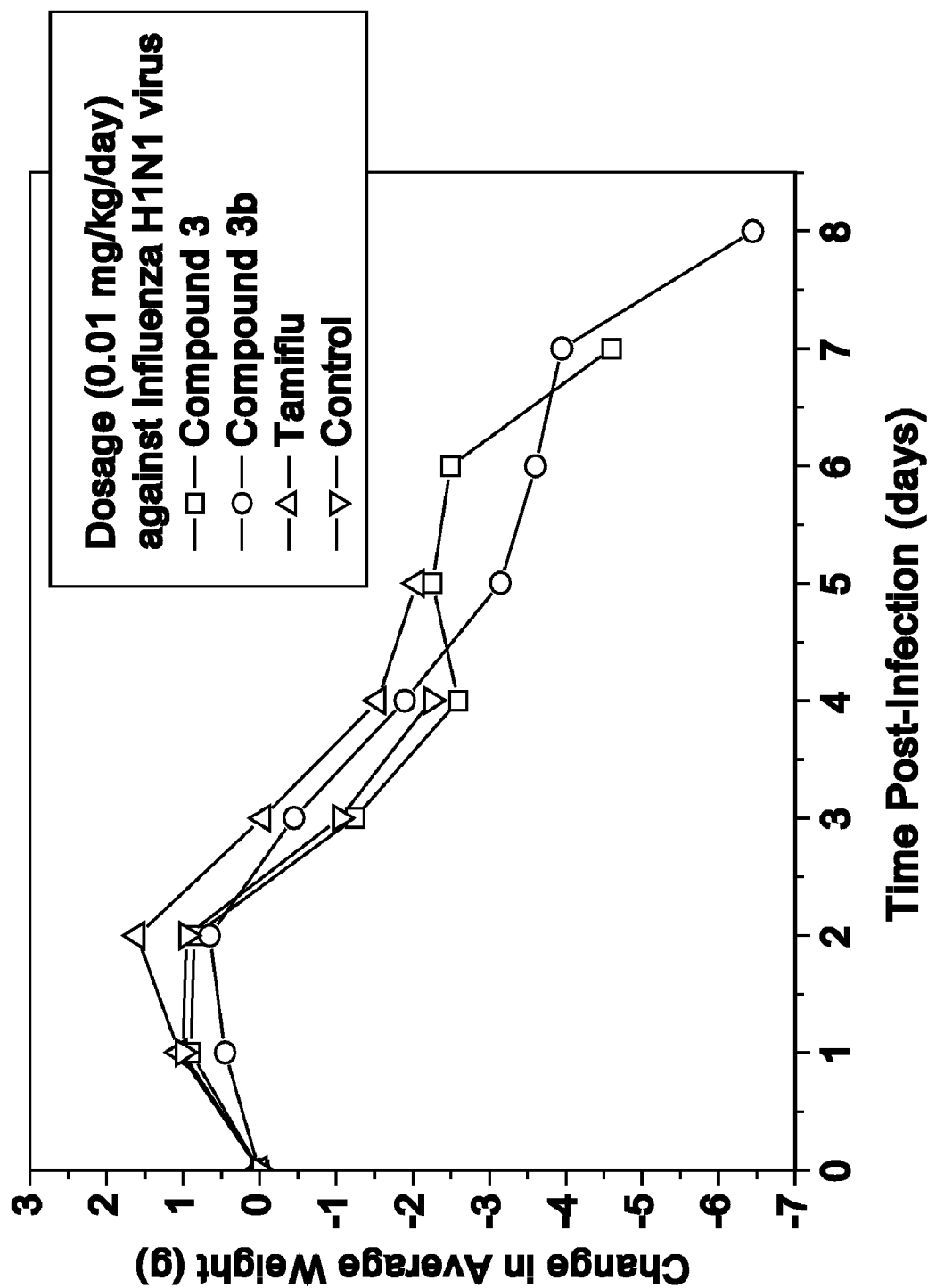
Figure 13A:
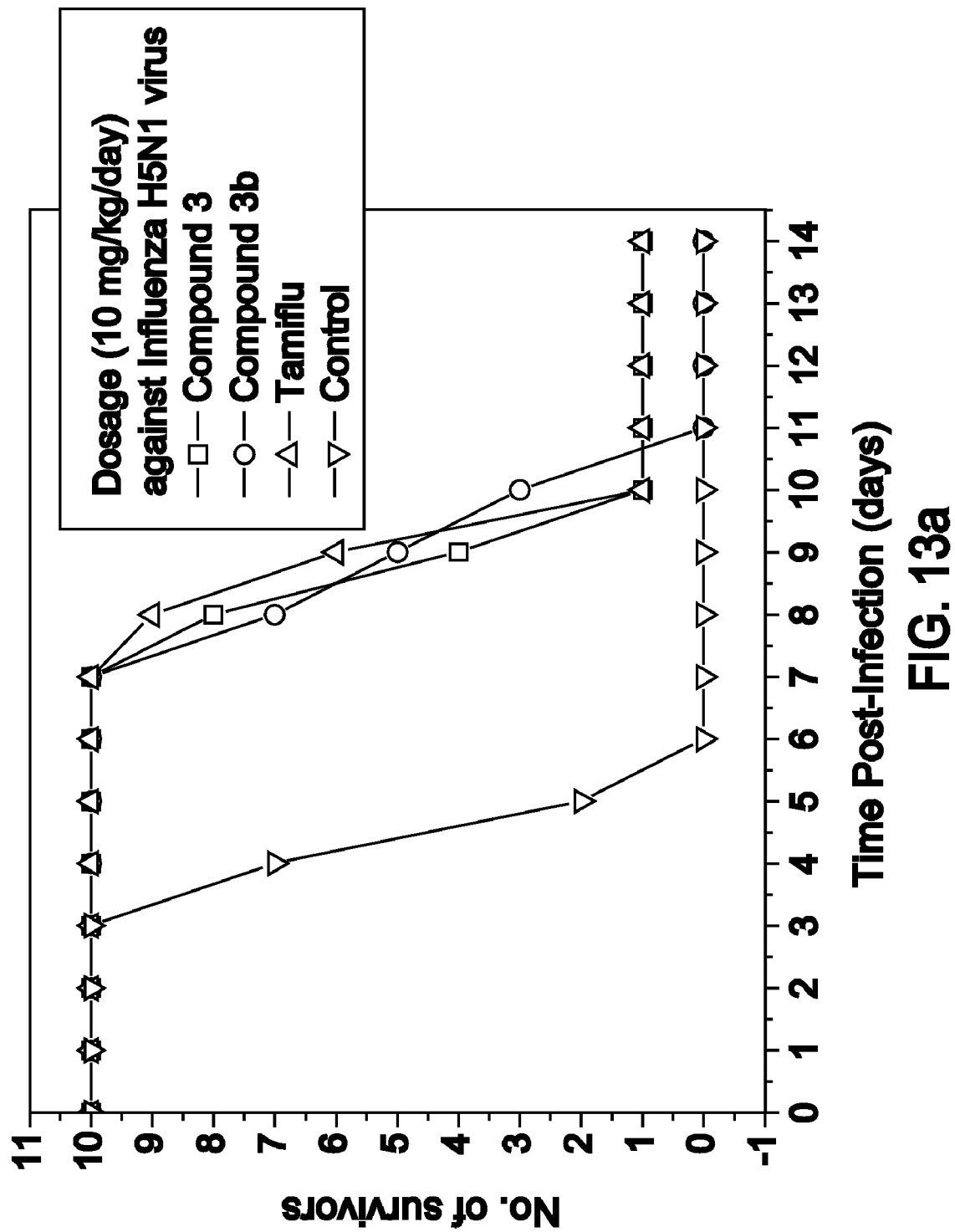
FIG. 13 shows survival rate (panel a) and change of average body weight (panel b) of mice inoculated with 10 $MLD_{50}$ of NIBRG-14 (H5N1) influenza virus and treated at a drug dosage of 10 mg/kg/day.
Figure 13B:
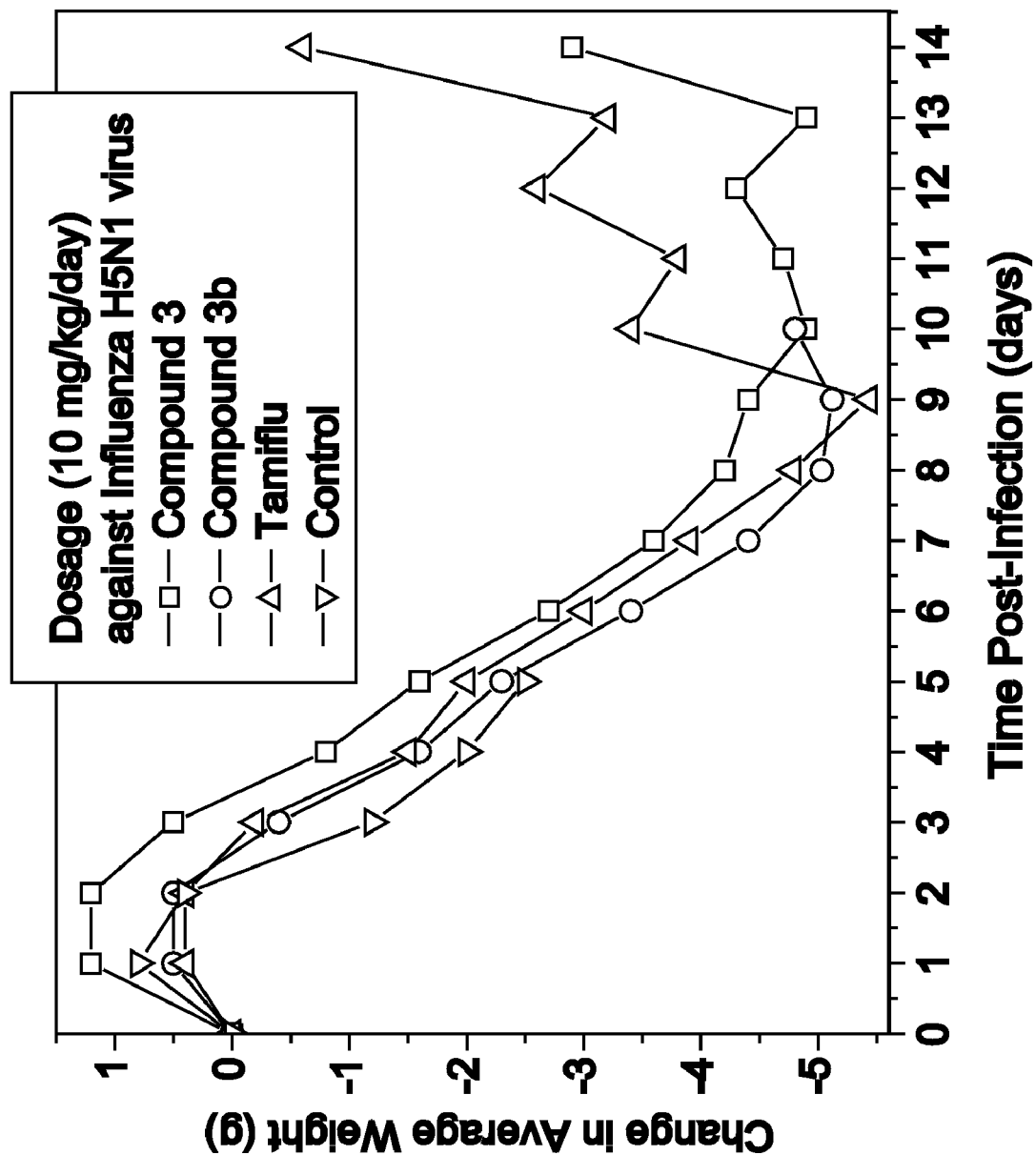
Figure 14A:
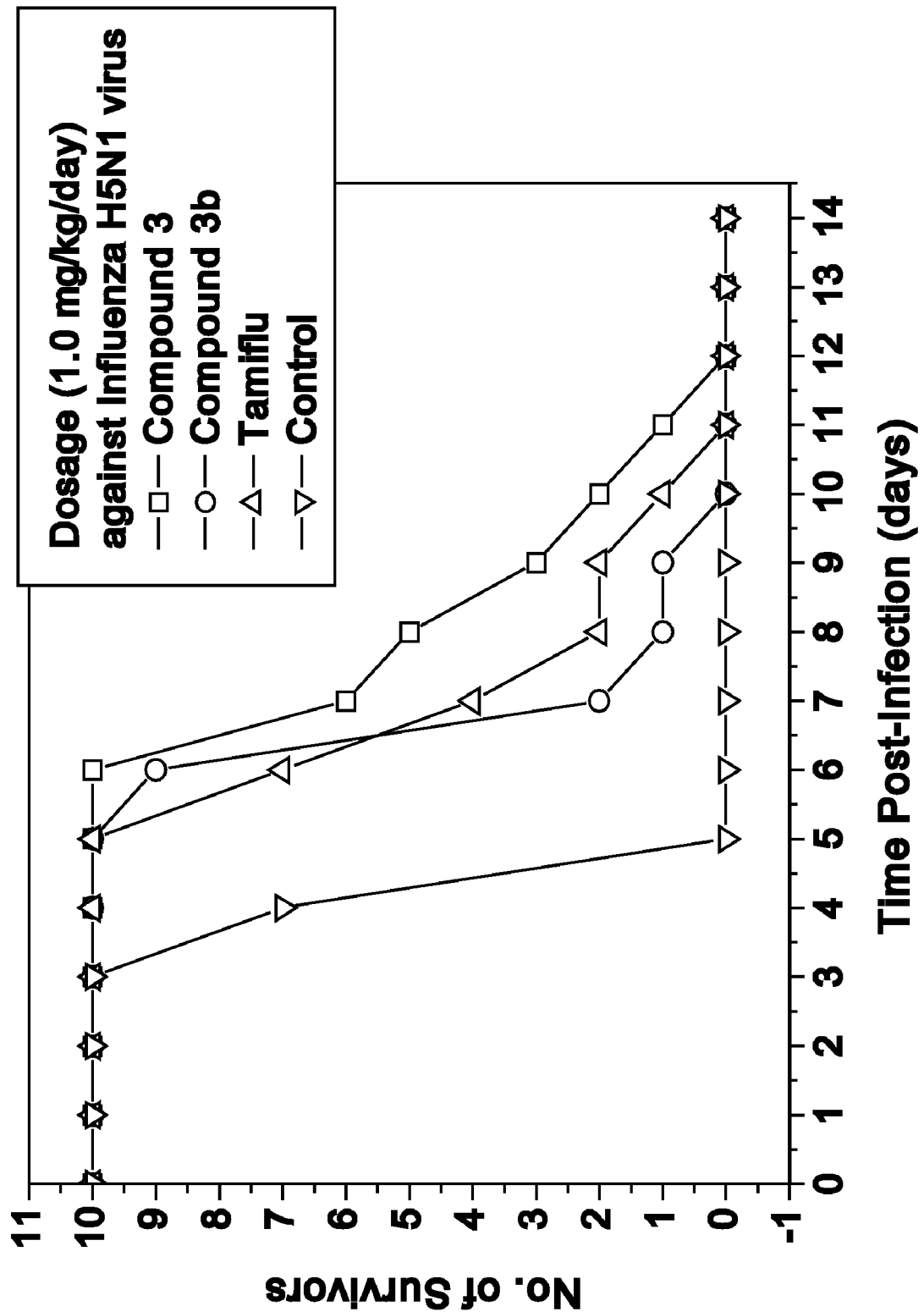
FIG. 14 shows survival rate (panel a) and change of average body weight (panel b) of mice inoculated with 10 $MLD_{50}$ of NIBRG-14 (H5N1) influenza virus and treated at a drug dosage of 1 mg/kg/day.
Figure 14B:
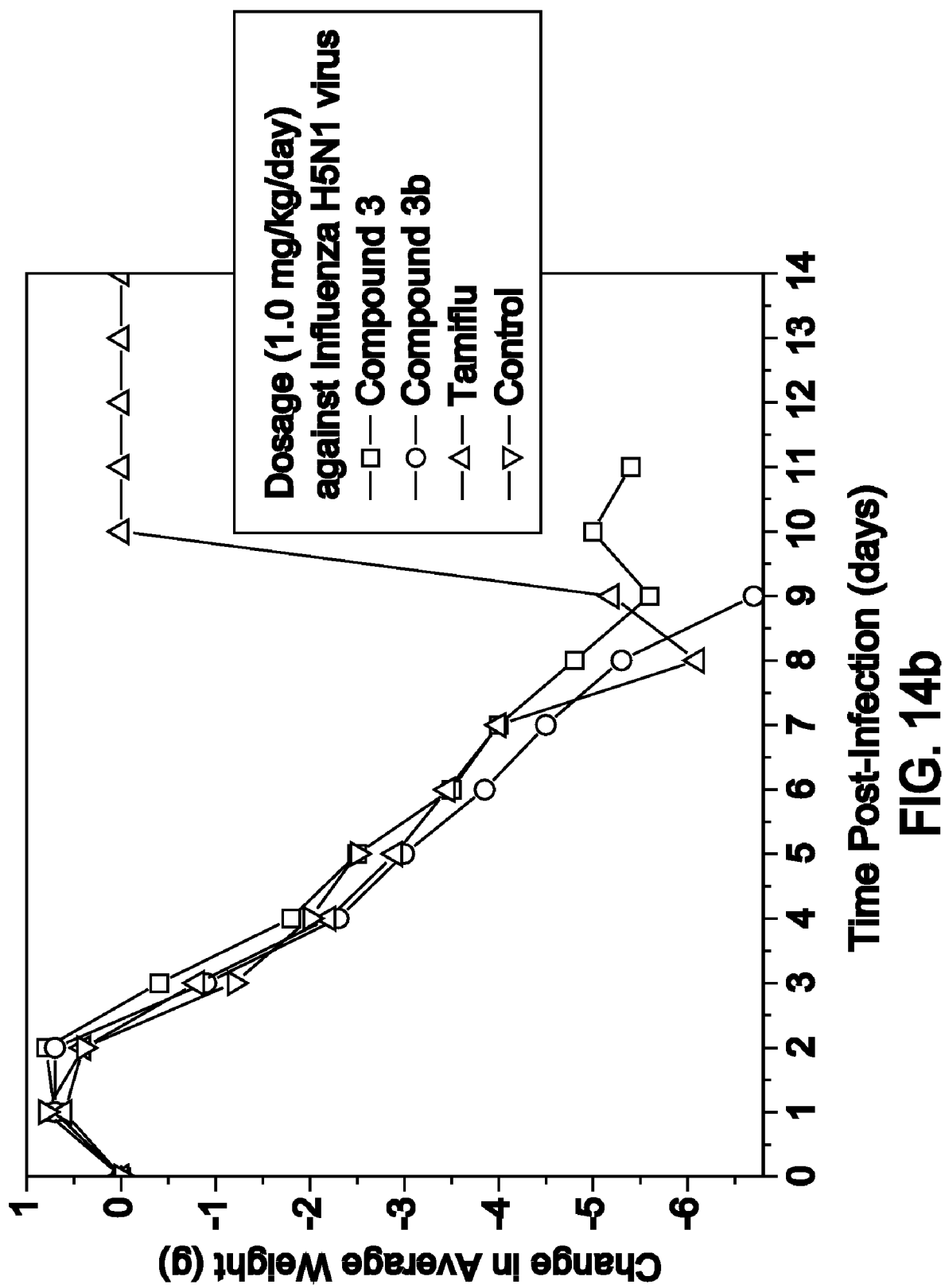
Figure 15A:
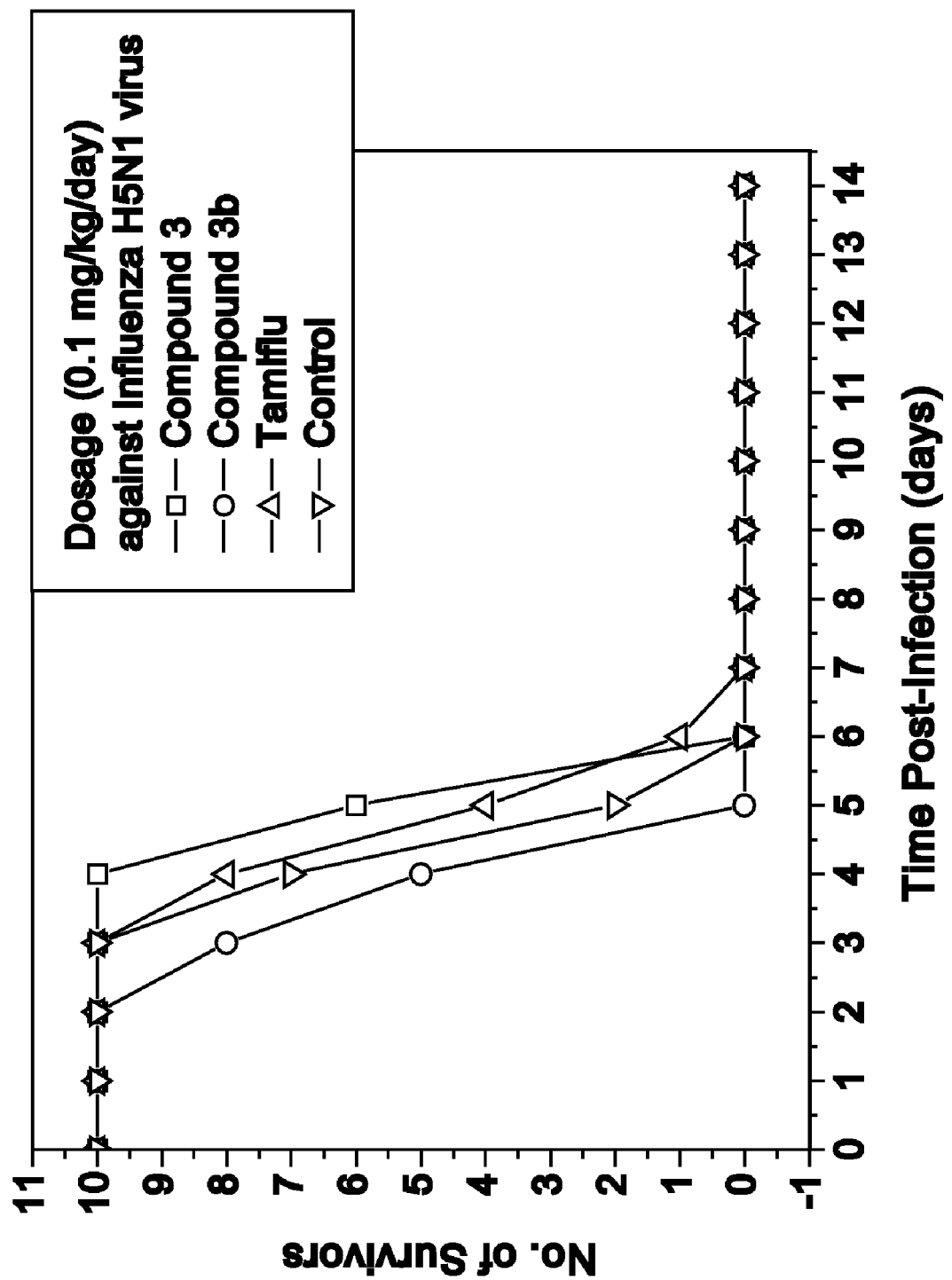
FIG. 15 shows survival rate (panel a) and change of average body weight (panel b) of mice inoculated with 10 $MLD_{50}$ of NIBRG-14 (H5N1) influenza virus and treated at a drug dosage of 0.1 mg/kg/day.
Figure 15B:
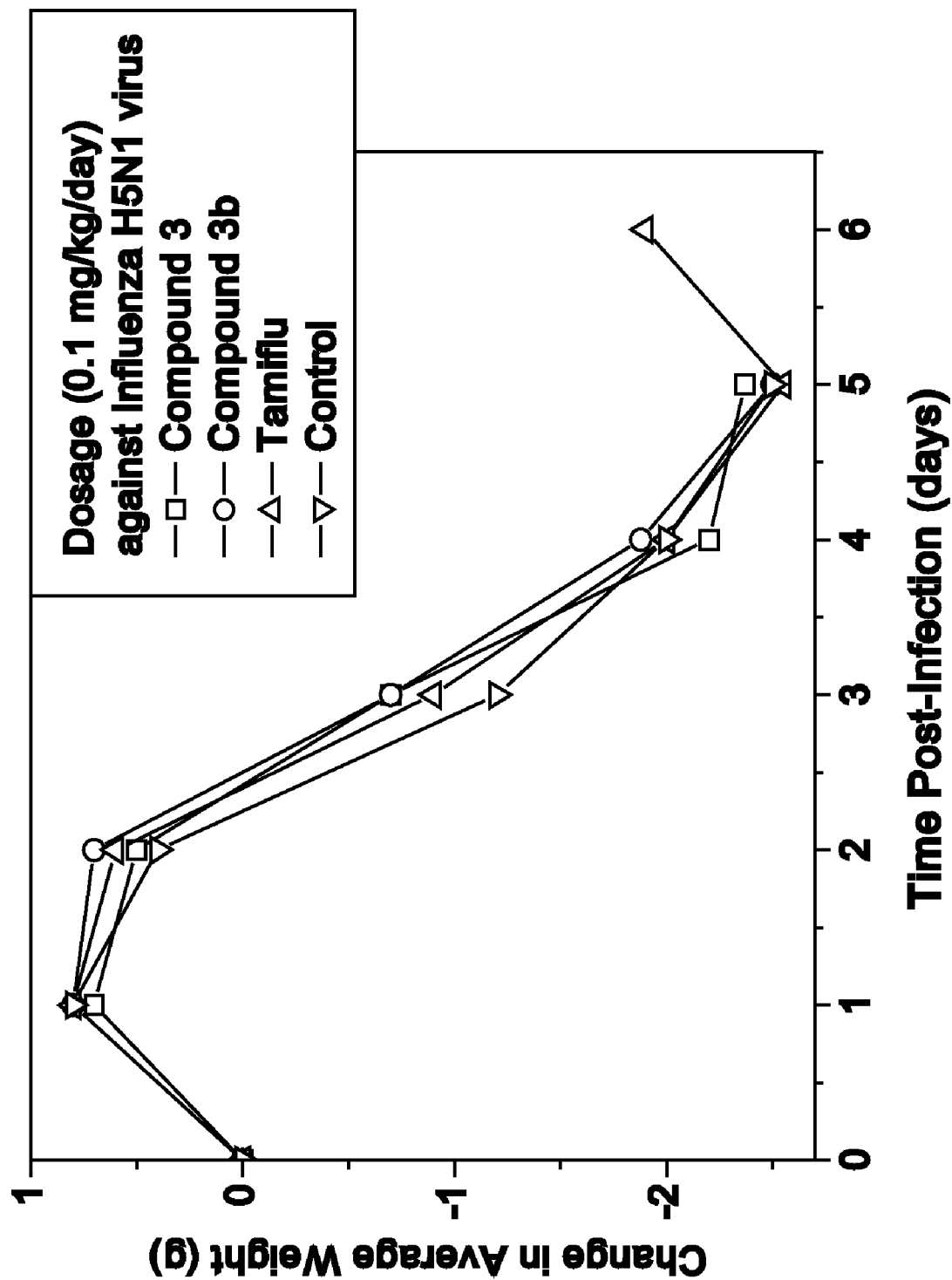
Figure 16A:
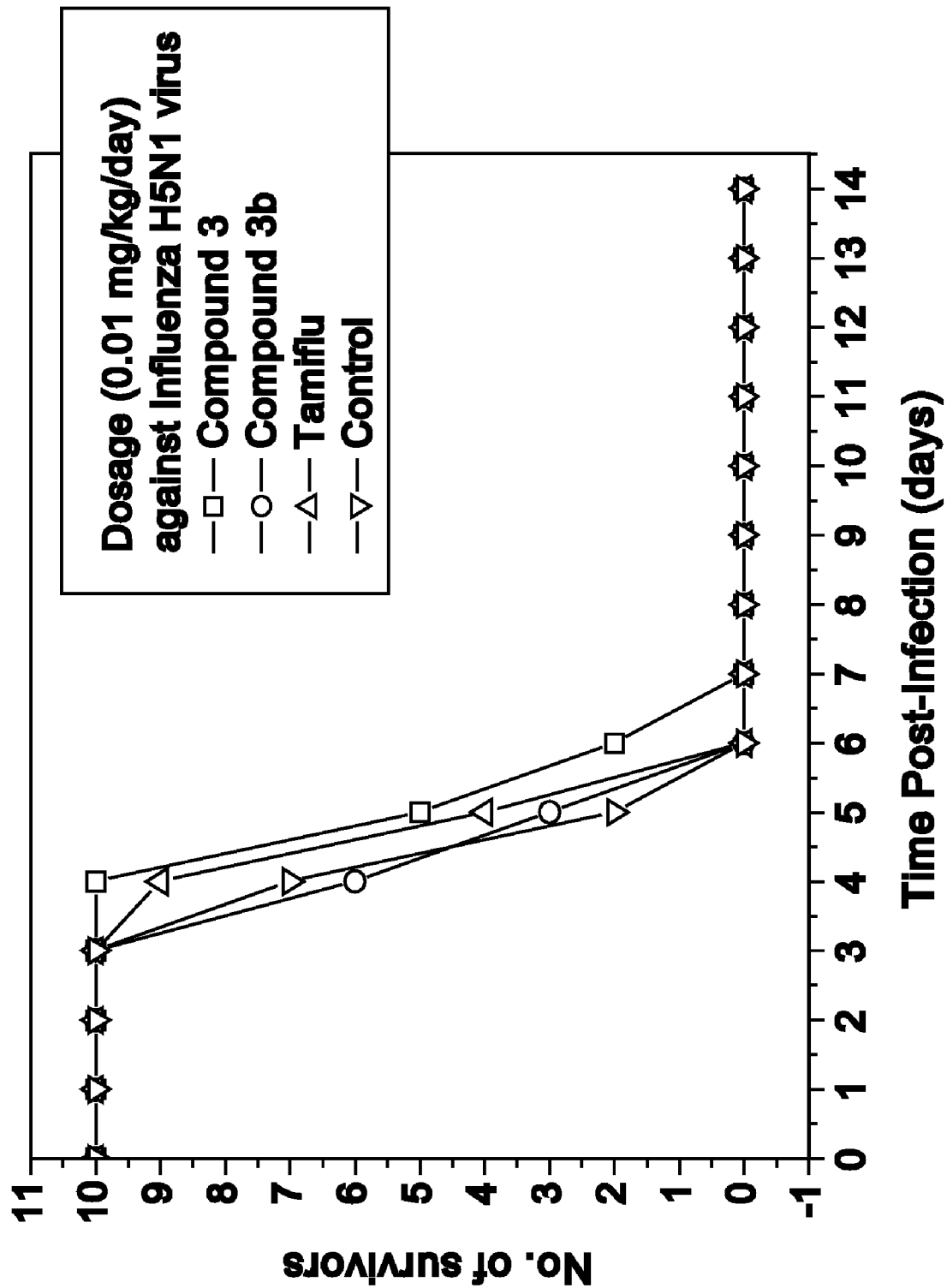
FIG. 16 shows survival rate (panel a) and change of average body weight (panel b) of mice inoculated with 10 $MLD_{50}$ of NIBRG-14 (H5N1) influenza virus and treated at a drug dosage of 0.01 mg/kg/day.
Figure 16B:
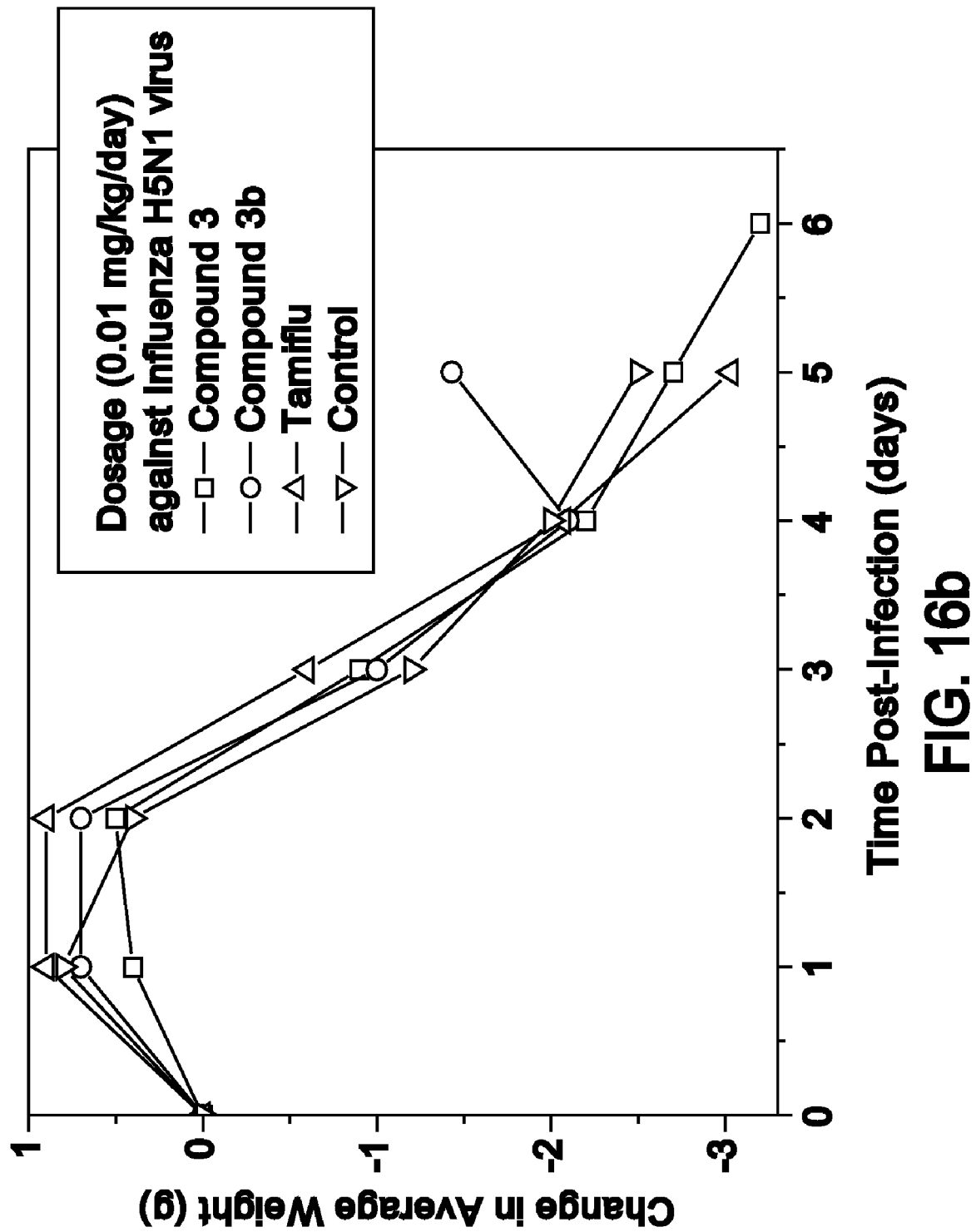
Figure 17B:
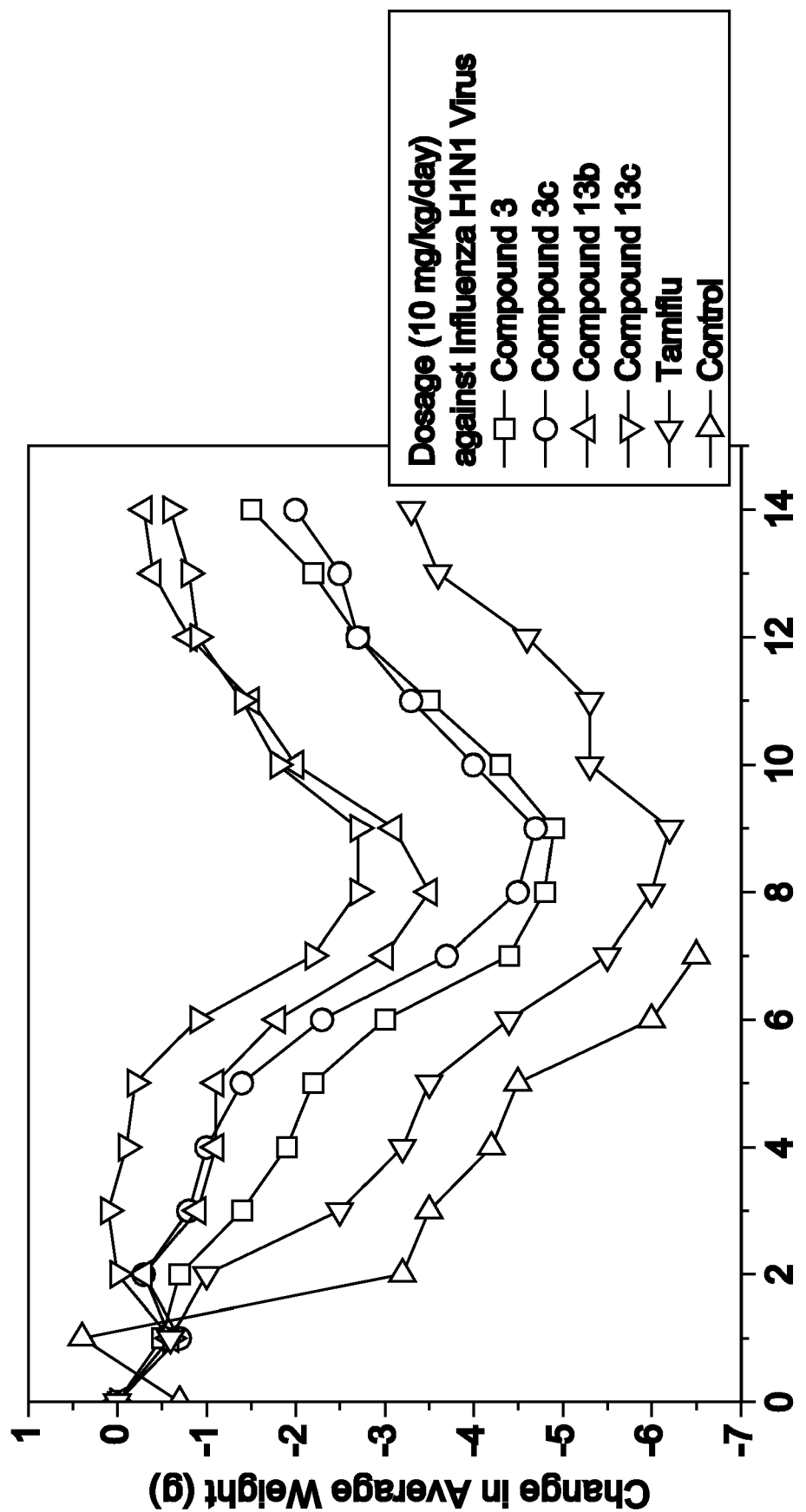
FIG. 17 shows survival rate (panel a) and change of average body weight (panel b) of mice inoculated with 10 $MLD_{50}$ of A/WSN/33 (H1N1) influenza virus and treated at a drug dosage of 10 mg/kg/day.
Figure 18A:
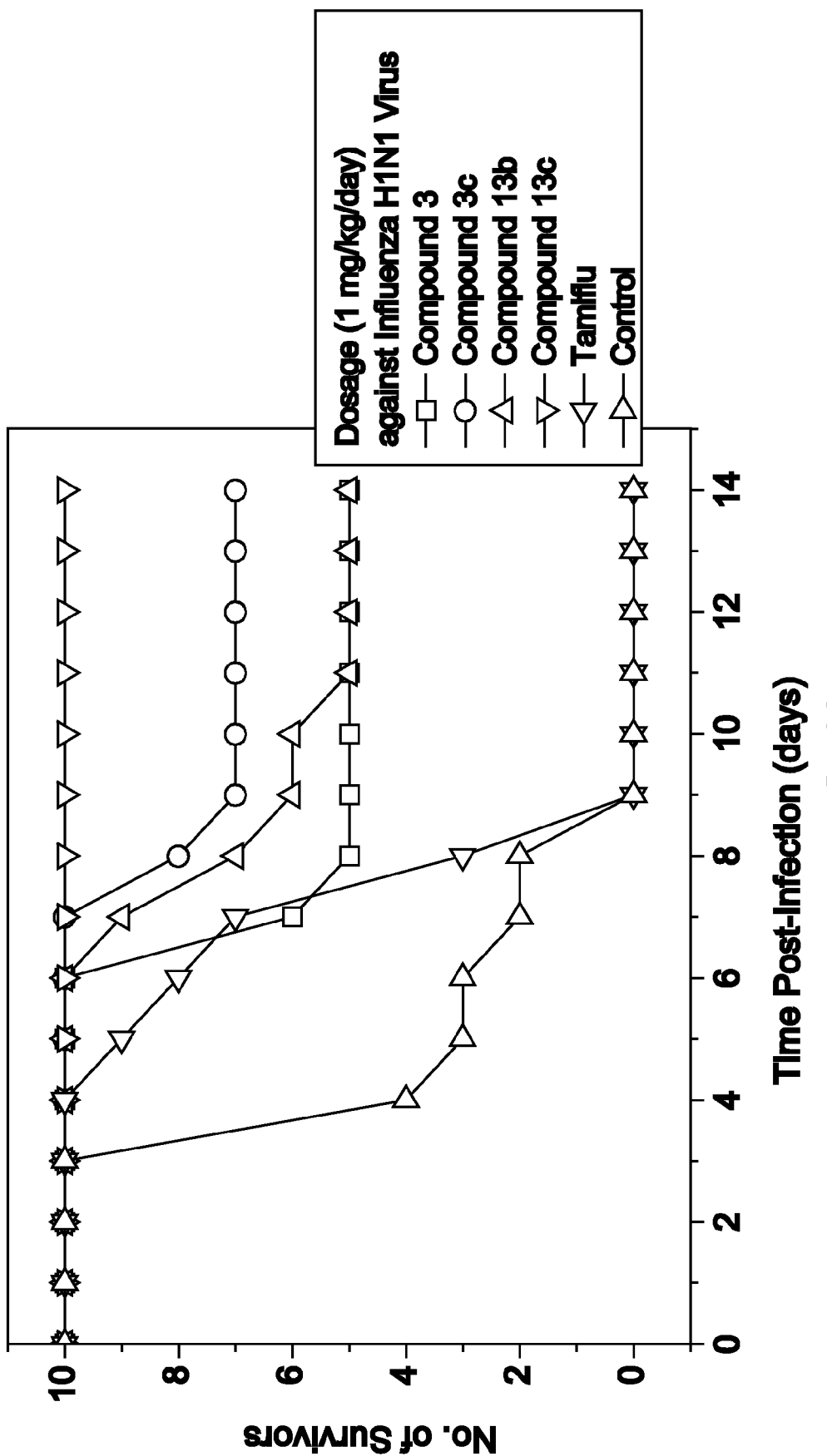
FIG. 18 shows survival rate (panel a) and change of average body weight (panel b) of mice inoculated with 10 $MLD_{50}$ of A/WSN/33 (H1N1) influenza virus and treated at a drug dosage of 1 mg/kg/day.
Figure 19A:
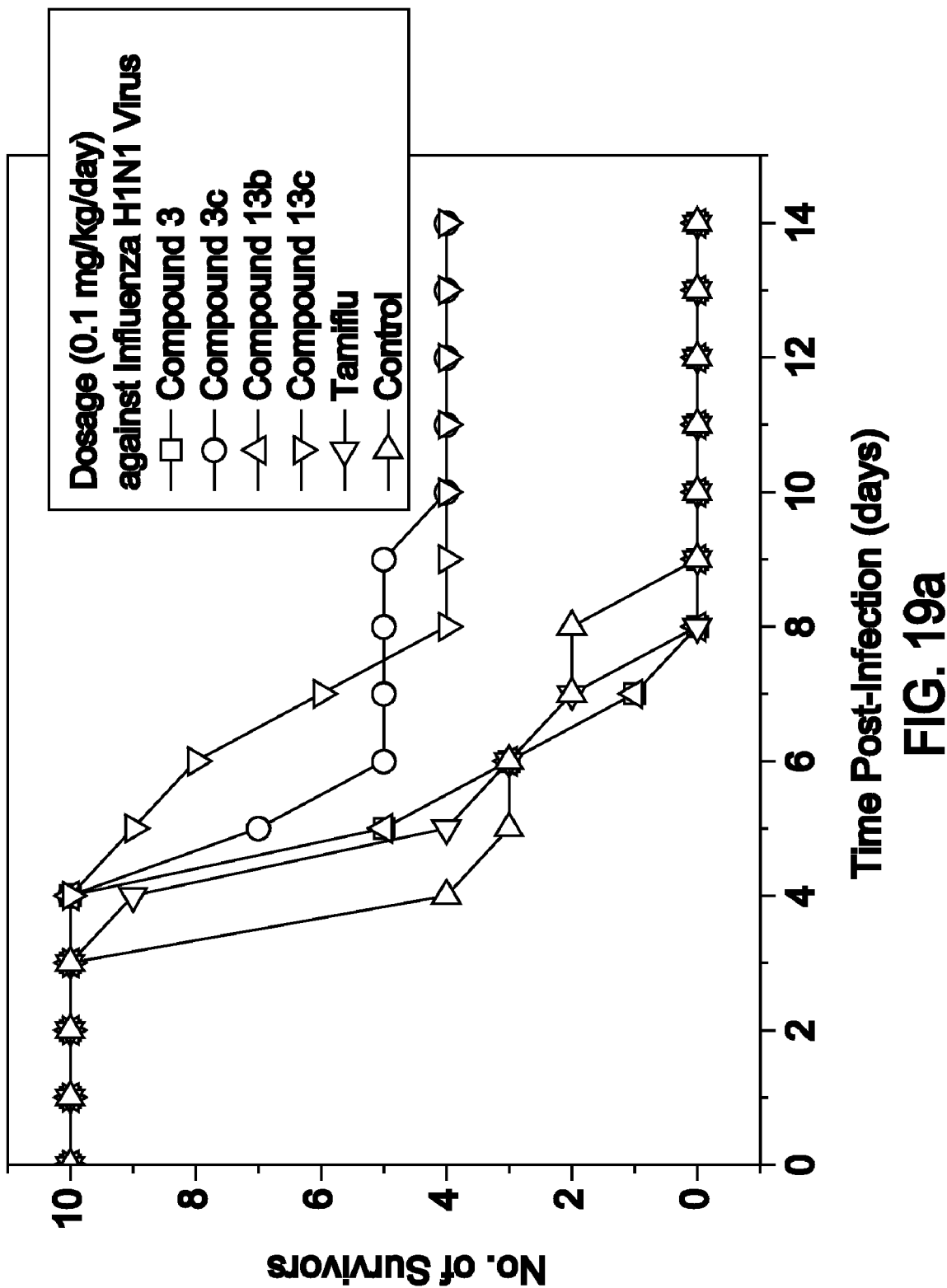
FIG. 19 shows survival rate (panel a) and change of average body weight (panel b) of mice inoculated with 10 $MLD_{50}$ of A/WSN/33 (H1N1) influenza virus and treated at a drug dosage of 0.1 mg/kg/day.
Figure 19B:
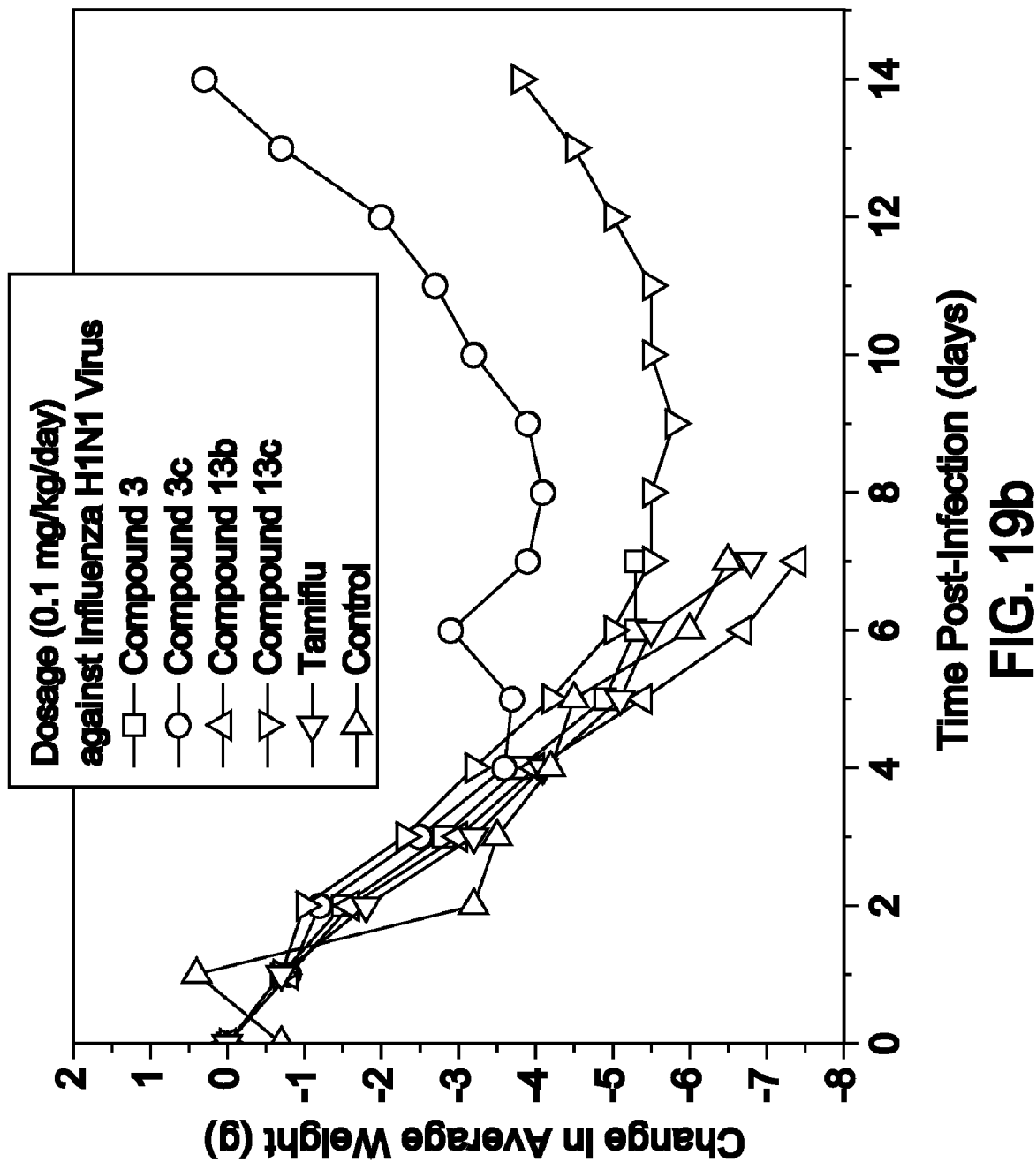
Figure 20A:
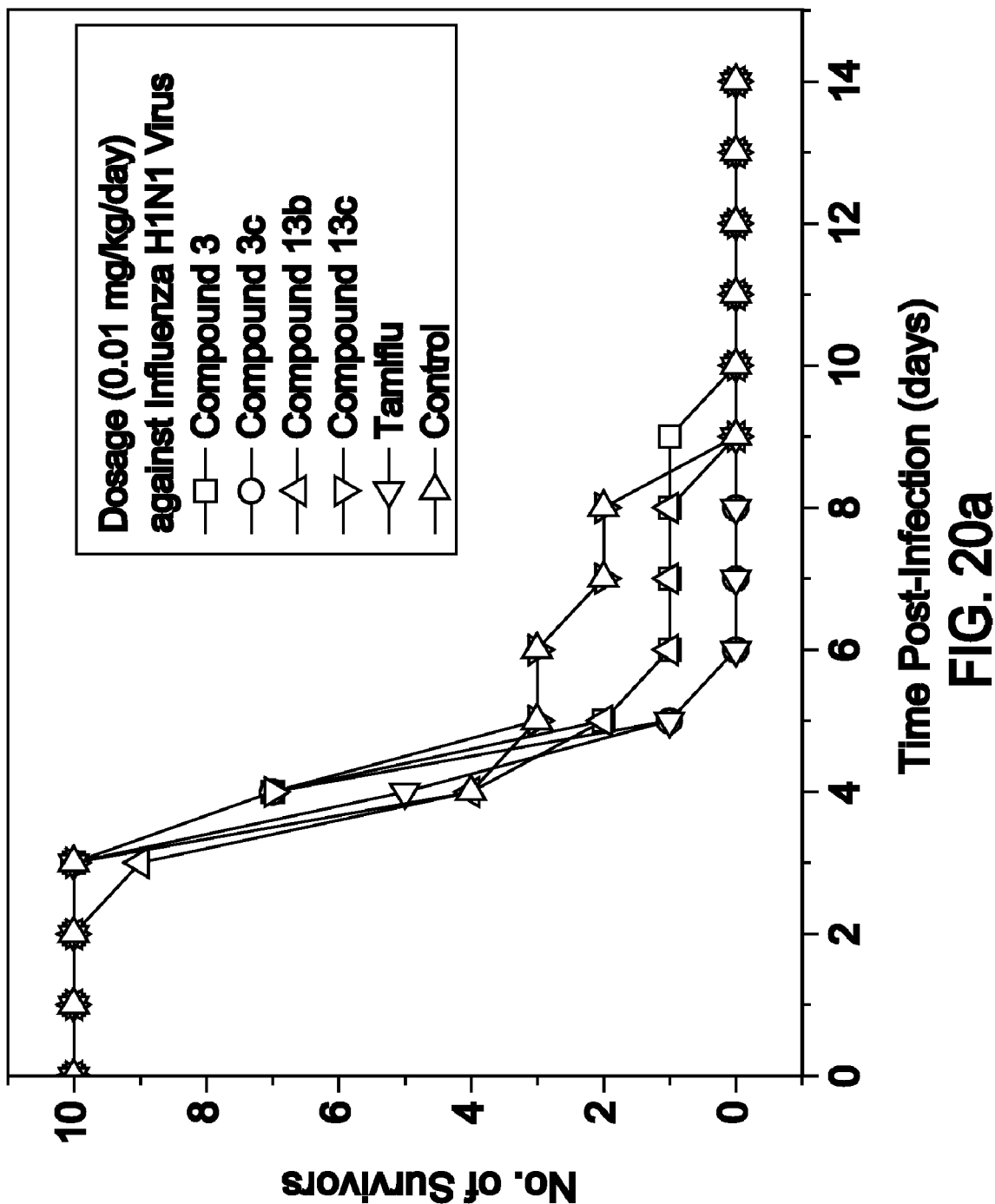
FIG. 20 shows survival rate (panel a) and change of average body weight (panel b) of mice inoculated with 10 $MLD_{50}$ of A/WSN/33 (H1N1) influenza virus and treated at a drug dosage of 0.01 mg/kg/day.
Figure 20B:
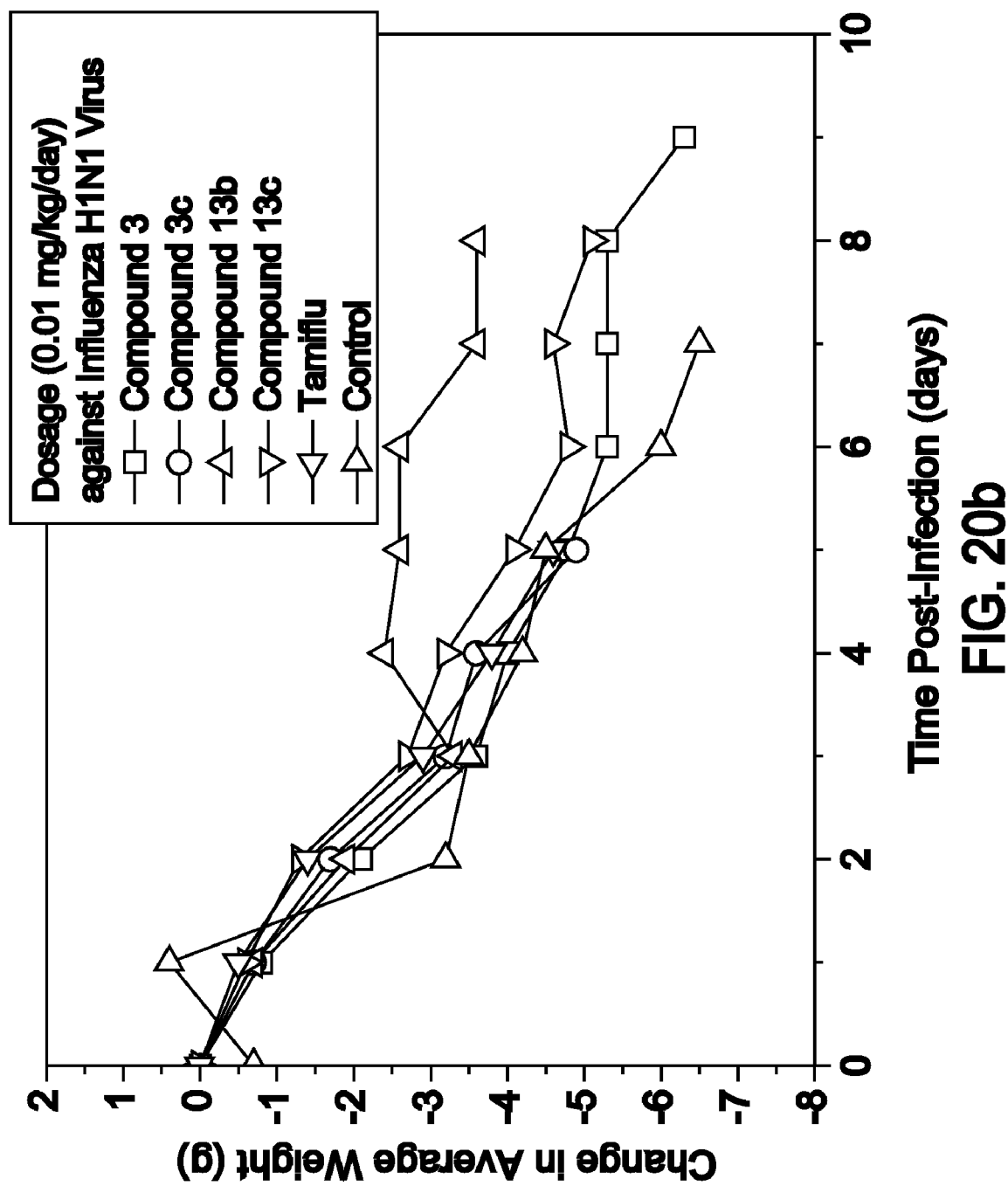

It is known in the art to obtain phosphonate monoesters by utilizing basic hydrolysis of the phosphonate diester. Phosphonate monoesters are thus contemplated in one aspect of the invention. Synthesis of the monoesters are shown in FIG. 7 for compound 3c and FIG. 8 for compound 13c. Each of these are easily synthesized from other synthesis processes disclosed herein from the starting compounds 31b or 12b to synthesize compounds 3c and 13c respectively.

The compositions of this invention optionally comprise salts of the compounds herein, especially pharmaceutically acceptable non-toxic salts containing, for example, Na$^+$, Li$^+$, K$^+$, Ca$^{++}$ and Mg$^{++}$. Such salts may include those derived by combination of appropriate cations such as alkali and alkaline earth metal ions or ammonium and quaternary amino ions with an acid anion moiety.

Metal salts may be prepared by reacting the metal hydroxide with a compound of this invention. Examples of metal salts which are prepared in this way are salts containing Na$^+$, Li$^+$, K$^+$.

In addition, salts may be formed from acid addition of certain organic and inorganic acids, e.g., HCl, HBr, H$_2$SO$_4$, or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates. Another aspect of the invention relates to methods of inhibiting the activity of neuraminidase comprising the step of treating a sample suspected of containing neuraminidase with a compound of the invention.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986), which is expressly incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about pH 3 to about pH 11, but is ordinarily about pH 7 to pH 10.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and. intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route. Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient. Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

In one implementation, active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with antivirals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Another implementation of the invention includes in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabeled (e.g. $^{14}C$ or $^3H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Prodrugs of the novel phosphonate congeners are contemplated. Both the polar phosphonate and guanidinium groups may be optionally further functionalized by techniques known in the art to enhance pharmacokinetic and/or pharmacodynamic properties. For example, formulation and use of prodrugs, e.g. acyloxymethyl- and aryl phosphonate esters, may be utilized to enhance oral bioavailability (Krise and Stella, *Adv. Drug Deliv. Rev.* 1996, 19, 287).

In one aspect of the invention, samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above. If desired, the activity of neuraminidase after application of the composition can be observed by any method including direct and indirect methods of detecting neuraminidase activity. Quantitative, qualitative, and semi-quantitative methods of determining neuraminidase activity are all contemplated. Typically one of the screening methods described above are applied, however, any other method such as observation of the physiological properties of a living organism are also applicable.

Organisms that contain neuraminidase include bacteria (*Vibrio cholerae, Clostridium perfringens, Streptococcus pneumoniae,* and *Arthrobacter sialophilus*) and viruses (especially orthomyxoviruses or paramyxoviruses such as influenza virus A (e.g. H1N1, H5N1), and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24. The compounds of this invention are useful in the prophylaxis of influenza infections or treatment of existing influenza infections in animals such as ducks and other birds, rodents, swine, or in humans.

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro $K_i$ (inhibitory constants) of less then about $5 \times 10^{-6}$ M, typically less than about $1 \times 10^{-7}$ M and preferably less than about $5 \times 10^{-8}$ M are preferred for in vivo use.

Useful in vitro screens have been described in detail and will not be elaborated here. (Itzstein, M. von et al.; "Nature", 363(6428):418-423 (1993); Potier, M.; et al.; "Analyt. Biochem.", 94:287-296 (1979); Chong, A. K. J.; et al.; "Biochem. Biophys. Acta", 1077:65-71 (1991); and Colman, P. M.; et al.; International Publication No. WO 92/06691 (Int. App. No. PCT/AU90/00501, publication date Apr. 30, 1992).

In vivo screens have also been described in detail, see for example, Itzstein, et al., 1993 in particular page 421, column 2, first full paragraph, to page 423, column 2, first partial paragraph, and Colman, p. 36. NAIs of the present disclosure were tested for inhibitory activity against various influenza virus neuraminidases. Table 1 shows inhibitory activities against wild-type and mutant influenza virus neuraminidases.

TABLE 1

| | Neuraminidase inhibition, IC$_{50}$ (nM) | | | |
|---|---|---|---|---|
| Cmpd. | Wt (WSN)[a] | Mut (WSN)[b] | Wt (Hanoi)[c] | Mut (Hanoi)[d] |
| 2 | 5.90 (±0.62) | 295 (±31) | 62.9 (±5.7) | 971 (±54) |
| 3[e] | 0.30 (±0.05) | 526 (±44) | 13.3 (±1.0) | 1210 (±490) |
| 13a | 4.10 (±0.51) | 252 (±31) | 160 (±32) | 1150 (±380) |
| 13b[e] | 0.12 (±0.02) | 7.39 (±0.67) | 1.82 (±0.11) | 19.5 (±1.4) |

TABLE 1-continued

| | Neuraminidase inhibition, IC$_{50}$ (nM) | | | |
|---|---|---|---|---|
| Cmpd. | Wt (WSN)[a] | Mut (WSN)[b] | Wt (Hanoi)[c] | Mut (Hanoi)[d] |
| 14a | 36700 | ND[f] | ND[f] | ND[f] |
| 14b[e] | 3200 | ND[f] | ND[f] | ND[f] |

[a]Neuraminidase(NA) from influenza virus A/WSN/1933 (H1N1).
[b]NA (H274Y) from influenza virus A/WSN/1933 (H1N1).
[c]NA from influenza virus A/Hanoi/30408/2005 (H5N1).
[d]NA (H274Y) from influenza virus A/Hanoi/30408/2005 (H5N1).
[e]As the ammonium salt depicted in FIG. 3.
[f]Not determined.

The greater potencies of the phosphonate congeners, 3 (Tamiphosphor) versus oseltamivir 2 and guanidine 13b versus 13a, were observed in the wild-type neuraminidases of H1N1 and H5N1 influenza viruses (Table 1). Both compounds 3 and 2 are significantly less potent toward the NAI resistant mutants of H274Y[7] than the wild-type enzymes. Nevertheless, the phosphonate compound 13b is an effective inhibitor that inhibits both mutant enzymes at low nM concentrations. Compounds 14a and 14b, which lack the pentyloxy group at the C-3 hydroxyl position in comparison with 2 and 3, showed inferior NAI activity. Table 2 shows neuraminidase inhibition, anti-influenza, and cytotoxicity activities of oseltamivir 2, phosphonate congener 3 and the related analogs.

TABLE 2

| Cmpd | $K_i$ (nM)[a] | EC$_{50}$ (nM)[b] | CC$_{50}$ (µM)[c] | S.I.[d] |
|---|---|---|---|---|
| 2 | 2.90 (±0.30) | 31.3 (±3..5) | >100 | >3200 |
| 3[e] | 0.15 (±0.02) | 4.67 (±0.68) | 74 (±5.7) | 15800 |
| 13a | 2.02 (±0.25) | 5.60 (±1.2) | >100 | >17800 |
| 13b[e] | 0.06 (±0.01) | 0.09 (±0.02) | ~5 | ~56000 |

[a]Neuraminidase inhibition against influenza virus A/WSN/1933 (H1N1). $K_i$ values were determined by using Cheng-Prusoff equation.
[b]Concentrations of NA inhibitors for 50% protection of the CPE effects due to flu (A/WSN/1933) infection.
[c]The highest concentration used is 100 µM in the assay of cytotoxicity on MDCK cells.
[d]Selectivity index, the ratio of CC$_{50}$ to EC$_{50}$.
[e]As the ammonium salt depicted in FIG. 3.

In one implementation of the present disclosure, phosphonate 3 is a potent NA inhibitor and anti-flu agent against influenza H1N1 virus with $K_i$ and EC$_{50}$ values of 0.15 and 4.67 nM (Table 2). In comparison, phosphonate 3 is more active than oseltamivir by 19 - and 7- folds, respectively, an the NA inhibition and anti-flu assays. The phosphate 3 was further evaluated at multiple concertrations to determine the growth inhibition on the host MDCK cells. The deduced CC$_{50}$ value of phosphonate 3 74 µM. the phosphoate 3, showing a high selectivity index of greater than 15800, is thus a potent antiviral agent against H1N1 virus with no toxicity to the host MDCK cells. By replacing the amino group in 3 with a guanidino group, the phosphonate 13b exihibits an enhanced NA inhibition ($K_i$=0.06 nM) and anti-flu activity (EC$_{50}$=0.09 nM). By analogy to the previous reports, the guanidinium group may exert strong eletrostatic interactions with the residues of Glu119, Asp151 and Glu227.

In one aspect, phoshonate congeners described in this study are significantly more potent than the carboxylate congeners against the wild-type neuraminidases of H1N1 and H5N1. In addition, compound 13b is an effective inhibitor at 19 nM for the H274Y mutant of a H5N1 neuraminidase.

In another implementation of the present disclosure, compounds of the present disclosure are used to treat influenza infection in vivo. NAIs of the present disclosure were tested in mice in vivo. Mice were treated with drug at dosages indicated by oral gavage twice daily for 5 days. Four hours after the first dose of drug, mice were inoculated intranasally with 10 $MLD_{50}$ in 25μL of infectious influenza virus [A/WSN/33 (H1N1) or NIBRG-14 (H5N1)]. Mice were observed daily for 14 days for survival and body weight. Table 3 shows effects of treatment with compounds 3 and 3b, and Tamiflu on A/WSN/33 (H1N1) influenza virus infections in mice.

TABLE 3

| Compound | Dosage (mg/kg/day)[a] | % Survivors[b] | Mean day to death[c] |
|---|---|---|---|
| Control |  | 0 (0)[b] | 4.6 |
| 1 (Tamiflu) | 10 | 0 (100)[b] | 9.8 |
|  | 1 | 0 (40)[b] | 7.1 |
|  | 0.1 | 0 (20)[b] | 6.4 |
|  | 0.01 | 0 (0)[b] | 5.6 |
| 3 | 10 | 90 (100)[b] | 11 |
|  | 1 | 50 (100)[b] | 9.8 |
|  | 0.1 | 0 (100)[b] | 9.3 |
|  | 0.01 | 0 (10)[b] | 4.7 |
| 3b | 10 | 0 (100)[b] | 9.6 |
|  | 1 | 0 (100)[b] | 8.9 |
|  | 0.1 | 0 (60)[b] | 7.8 |
|  | 0.01 | 0 (30)[b] | 7.0 |

[a]Compounds were administered orally twice daily for 5 days beginning 4 h prior to infection with the indicated influenza virus.
[b]Number of survivors/Total number treated. The first number represents the % survival at day 14, and the number in parentheses represents the % survival at day 7.
[c]Mean day to death of mice dying prior to day 14.

Effects of treatment on survival with compounds 3 and 3b, and Tamiflu on NIBRG-14 (H5N1) influenza A virus infections in mice are shown in Table 4.

TABLE 4

| Compound | Dosage (mg/kg/day)[a] | % Survivors[b] | Mean day to death[c] |
|---|---|---|---|
| Control |  | 0 (0)[b] | 3.9 |
| 1 (Tamiflu) | 10 | 10 (100)[b] | 9.4 |
|  | 1 | 0 (40)[b] | 7.6 |
|  | 0.1 | 0 (0)[b] | 5.3 |
|  | 0.01 | 0 (0)[b] | 5.3 |
| 3 | 10 | 10 (100)[b] | 9.1 |
|  | 1 | 0 (60)[b] | 8.7 |
|  | 0.1 | 0 (0)[b] | 5.6 |
|  | 0.01 | 0 (0)[b] | 5.7 |
| 3b | 10 | 0 (100)[b] | 9.5 |
|  | 1 | 0 (20)[b] | 7.3 |
|  | 0.1 | 0 (0)[b] | 5.3 |
|  | 0.01 | 0 (0)[b] | 4.9 |

[a]Compounds were administered orally twice daily for 5 days beginning 4 h prior to infection with the indicated influenza virus.
[b]Number of survivors/Total number treated. The first number represents the % survival at day 14, and the number in parentheses represents the % survival at day 7.
[c]Mean day to death of mice dying prior to day 14.

Figure 1A:
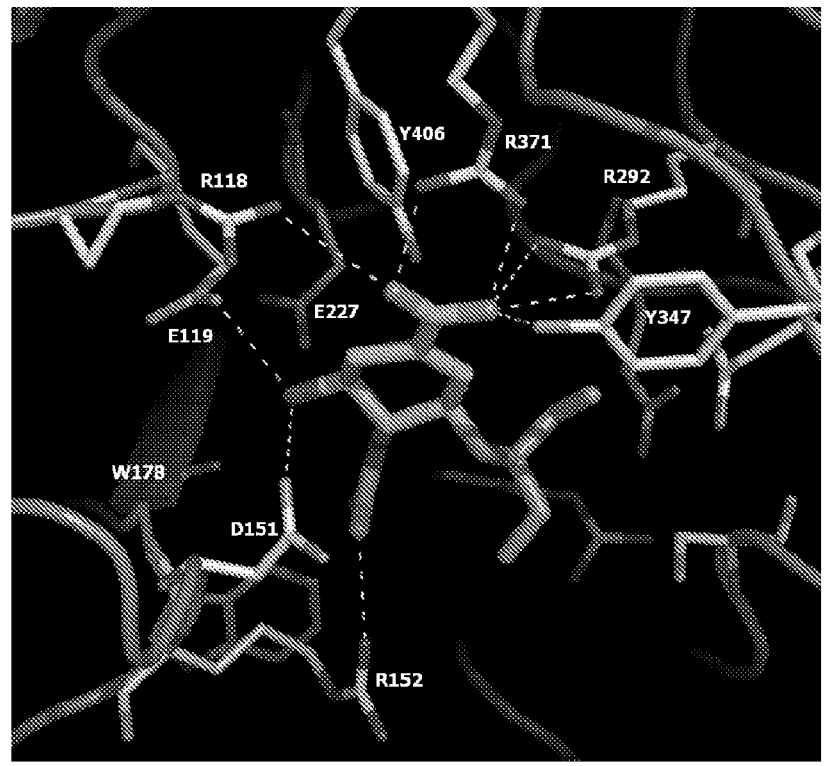
FIG. 1 shows molecular models of oseltamivir 2 (A) and the phosphonate compound 3a (B) in the active site of influenza virus neuraminidase (N1 subtype)

Molecular modeling of compound 3 in complex with NA was constructed through docking the compound 3 to the crystallographic structure of influenza virus neuraminidase (N1 subtype, PDB code: 2HU4). The 3-D structure of compound 3 was built by modifying the 3-D structure of oseltamivir 2 (also from 2HU4) with SYBYL 7.3. In one aspect of the invention, molecular modeling of the neuraminidase-phosphonate complex indicates a pertinent binding mode of the phosphonate with three arginine residues in the active site. Preliminary molecular docking experiments (FIG. 1) using the known N1 crystal structure (PDB code: 2HU4) reveal that the putative phosphonate inhibitor 3a indeed binds strongly with the tri-arginine residues of NA, in addition to other interactions exerted by the $C_3$-pentyloxy, $C_4$-acetamido and $C_5$-amino groups in the binding pocket similar to the NA-oseltamivir complex. FIG. 1 shows molecular models of oseltamivir 2 (A) and the phosphonate compound 3a (B) in the active site of influenza virus neuraminidase (N1 subtype). The complex of the phosphonate compound 3a has more extensive hydrogen bonding interactions (8 pairs ligand-NA H-bonds) with key residues in the NA active site than the oseltamivir-NA complex (6 pairs ligand-NA H-bonds).

Figure 6:
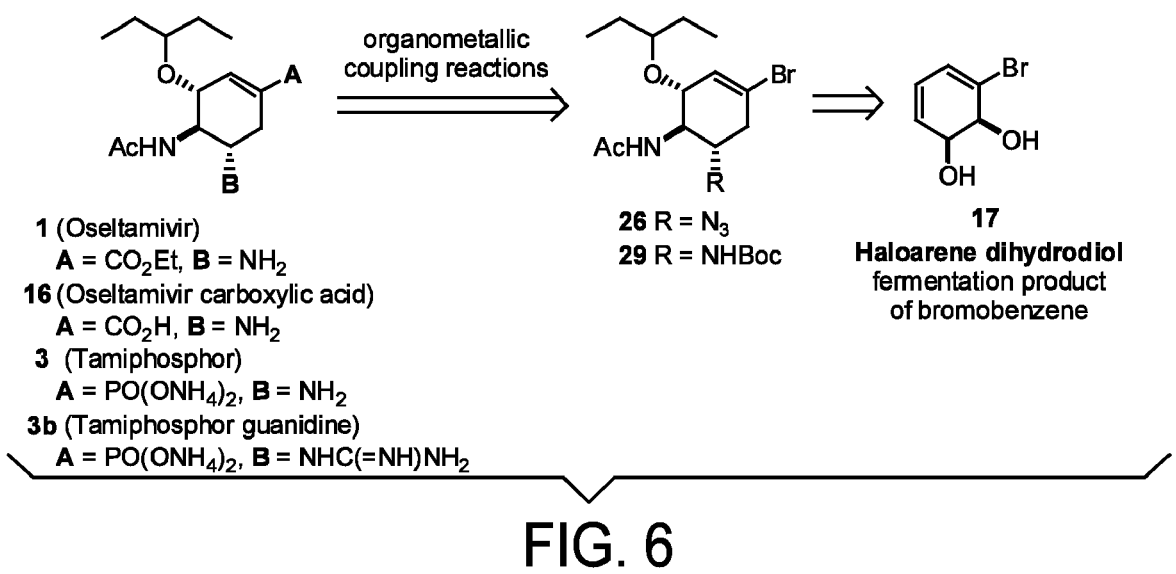
FIG. 6 shows a novel route to the synthesis of Tamiflu® 1 and the phosphonate congener Tamiphosphor 3, and 13b.

Also disclosed herein are novel and improved methods for the synthesis of Tamiflu® and the highly potent neuraminidase inhibitor Tamiphosphor. As previously disclosed herein, Tamiflu® (oseltamivir phosphate, 15.$H_3PO_4$), a popular drug for influenza treatment, is an orally administered prodrug, which is readily hydrolyzed by hepatic esterases to give the corresponding carboxylic acid (16, FIG. 6) as the active inhibitor of neuraminidase on influenza virus. Because the side effects of Tamiflu causing teenage patients to suffer from mental disorders, and the emergence of drug-resistant strains of avian flu, the development of new chemical entities against influenza viruses is urgently needed for our battle against the threat of pandemic flu. The synthesis summarized below is presented fully in FIG. 4:

Tamiphosphor (3) is a promising drug for fighting against both bird flu and human influenza. By replacing the carboxyl group in oseltamivir with a phosphonate group, Tamiphosphor interacts strongly with the tri-arginine residues of neuraminidase, and is more potent against the wild-type neuraminidases of H1N1 and H5N1 viruses. In addition, the guanidine analog 3b is an effective inhibitor ($K_i$=19 nM) of the H274Y mutant of a H5N1 neuraminidase. Furthermore, a preliminary study indicates that Tamiphosphor is also orally bioavailable in protecting mice against lethal challenge with influenza viruses. By comparison of the survival rate and mean survival time of mice (data not shown), Tamiphosphor is more effective than Tamiflu against H1N1 human influenza virus and at least equally effective against recombinant H5N1 (NIBRG14) virus.

The monoester derivatives of compounds 3 and 13 have also been demonstrated to be particularly effective in addressing influenza. As illustrated in Table 5, a mouse study showed that monoester compounds 3c and 13c were effective in treating mice having influenza. Table 4 shows the effects of intranasal treatment with Tamiflu (i), Tamiphosphor (3), Tamiphosphor monoester (3c), Tamiphosphor guanidine (13b) and Tamiphosphor guanidine monoester (13c) on influenza A [A/WSN/33 (H1N1)] virus infections in mice. The monoesters 3c and 13c are shown to be particularly effective, with improved survival rates and efficacy at lower concentrations.

TABLE 5

| Compound | Dosage (mg/kg/day)[a] | % Survivors[b] | Mean day to death[c] |
|---|---|---|---|
| Control (water) | ~ | 0 (20)[b] | 5.4 |
| 1 (Tamiflu) | 10 | 90 (100)[b] | 10 |
|  | 1 | 0 (80)[b] | 8.7 |
|  | 0.1 | 0 (20)[b] | 5.8 |
|  | 0.01 | 0 (0)[b] | 4.6 |
| 3 (Tamiphosphor) | 10 | 100 (100)[b] | ~ |
|  | 1 | 50 (100)[b] | 8.2 |
|  | 0.1 | 0 (10)[b] | 5.9 |
|  | 0.01 | 0 (10)[b] | 5.3 |
| 3c (Tamiphosphor monoester) | 10 | 100 (100)[b] | ~ |
|  | 1 | 70 (100)[b] | 9.3 |
|  | 0.1 | 40 (50)[b] | 6.2 |
|  | 0.01 | 0 (0)[b] | 4.8 |
| 13b (Tamiphosphor guanidine) | 10 | 100 (100)[b] | ~ |
|  | 1 | 50 (90)[b] | 9.8 |
|  | 0.1 | 0 (10)[b] | 5.9 |
|  | 0.01 | 0 (10)[b] | 4.8 |
| 13c (Tamiphosphor guanidine monoester) | 10 | 100 (100)[b] | ~ |
|  | 1 | 100 (100)[b] | ~ |
|  | 0.1 | 40 (60)[b] | 6.8 |
|  | 0.01 | 0 (20)[b] | 5.7 |

[a]Compounds were administered orally twice daily for 5 days beginning 4 h prior to infection with the indicated influenza virus.
[b]Number of survivors/Total number treated (10 mice). The first number represents the % survival at day 14, and the number in parentheses represents the % survival at day 7.
[c]Mean day to death of mice dying prior to day 14

FIGS. 17-20 illustrate graphically the efficacy of the monoester compounds 3c and 13c in comparison to compounds 3 and 13b. The compounds showed improved survival rates and improved weight retention. The trends are observed over a range of concentrations from 10 mg/kg/day to 0.1 mg/kg/day. At lower concentrations (FIG. 20), the monoesters are equally ineffective as compounds 3 and 13b, and closely mimic the control results, suggesting that at such low concentrations the beneficial effects of the phosphonate congeners is probably lost.

EXAMPLES

All reagents were commercially available and used without further purification unless indicated otherwise. All solvents were anhydrous grade unless indicated otherwise. Diisopropyl azidocarboxylate (DIAD) was purified by distillation on $Na_2SO_4$ under reduced pressure. All non-aqueous reactions were carried out in oven-dried glassware under a slight positive pressure of argon unless otherwise noted. Reactions were magnetically stirred and monitored by thin-layer chromatography on silica gel. Flash chromatography was performed on silica gel of 60-200 μm particle size. Yields are reported for spectroscopically pure compounds. Melting points were recorded on an Electrothermal MEL-TEMP® 1101D melting point apparatus and are not corrected. NMR spectra were recorded on Bruker AVANCE 600 and 400 spectrometers. Chemical shifts are given in δ values relative to tetramethylsilane (TMS); coupling constants J are given in Hz. Internal standards were $CDCl_3$ ($\delta_H$=7.24) or $D_2O$ ($\delta_H$=4.79) for $^1$H-NMR spectra, $CDCl_3$ ($\delta_H$=77.0) for $^{13}$C-NMR spectra, and $H_3PO_4$ in $D_2O$ ($\delta_P$=0.00) for $^{31}$P-NMR spectra. The splitting patterns are reported as s (singlet), d (doublet), t (triplet), q (quartet), m (multiplet), br (broad) and dd (double of doublets). IR spectra were recorded on a Thermo Nicolet 380 FT-IR spectrometer. Optical rotations were recorded on a Perkin-Elmer Model 341 polarimeter, the units for [α] and c are deg cm3 g$^{-1}$ dm$^{-1}$ and gcm$^{-3}$, respectively. High resolution ESI mass spectra were recorded on a Bruker Daltonics spectrometer.

Synthetic procedures and product characterization.

Example 1

1,2-O-Isopropylidene-3-amino-3-deoxy-α-D-ribofuranoside (5). (Nair, and Emanuel, J. Am. Chem. Soc. 1977, 99, 1571-1576)

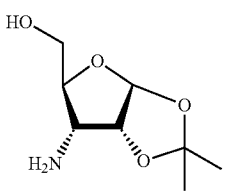

According to the reported procedures, (Suhara et al., J. Org. Chem. 2001, 66, 8760-8771) a suspension of D-xylose (50 g), anhydrous $CuSO_4$ (70 g) and conc. $H_2SO_4$ (5 mL) in acetone (1 L) was stirred at room temperature for 24 h, followed by partial hydrolysis in aqueous HCl solution (110 mL, 0.1 M) at 40° C. for 2 h, to give 1,2-O-isopropylidene-α-D-xylofuranose (4, 61 g) as colorless syrup. Compound 4 (10 g, 52.6 mmol) was treated with pivaloyl chloride (6.6 g, 54.8 mmol) in pyridine (50 mL) at 0° C. for 8 h to give 1,2-O-isopropylidene-5-O-pivaloyl-α-D-xylofuranoside (13 g, 85% yield from D-xylose) as colorless oil. Pyridinium dichromate (PDC, 8.92 g, 23.7 mmol) and $Ac_2O$ (12.2 mL, 130 mmol) were added to the pivaloyl ester (10.8 g, 39.4 mmol) in $CH_2Cl_2$ (160 mL). The mixture was heated under reflux for 1.5 h, and then concentrated under reduced pressure. The residue was dissolved in EtOAc (30 mL), and filtered through a silica gel pad by elution with EtOAc. The filtrate was concentrated and coevaporated with toluene (2×) to remove $Ac_2O$. The crude ketone product (10.2 g) was stirred with hydroxylamine hydrochloride (18.15 g, 260 mmol) in anhydrous pyridine (75 mL) at 60° C. for 24 h. The mixture was concentrated under reduced pressure, and the residue was dissolved in EtOAc. The organic layer was washed with water, and the aqueous layer was extracted with EtOAc (3×). The combined organic layers were dried over $MgSO_4$, filtered, and concentrated. The residual oil was purified by flash column chromatography on silica gel (EtOAc/hexane, 1:3) to afford the corresponding oxime (9.27 g, 82% yield for two steps) as a mixture of syn/anti isomers (70:30). Colorless oil; TLC (EtOAc/hexane, 1:4) $R_f$=0.4; $[\alpha]_D^{20}$=+162.5 (c=1, $CHCl_3$); IR (neat) 3501, 2988, 1769, 1292 cm$^{-1}$; $^1$H NMR (600 MHz, $CDCl_3$) (syn/anti isomers=7:3) δ 8.05 (0.3H, br s), 7.97 (0.7 H, br s), 5.98 (0.7 H, d, J=4.3 Hz), 5.96 (0.3 H, d, J=4.3 Hz), 5.27-5.25 (1 H, m), 4.99 (1 H, dd, J=4.2, 1.3 Hz), 4.97-4.96 (0.3 H, m), 4.55 (0.7H, dd, J=11.1, 2.6 Hz), 4.33 (0.3 H, dd, J=11.1, 2.6 Hz), 4.23-4.20 (1 H, m), 1.47 (3 H, s), 1.42 (3 H, s), 1.16 (9 H, s); $^{13}$C NMR (150 MHz, $CDCl_3$) δ 178.1/1770.9, 158.4/157.3, 114.2/113.7, 105.0/104.8, 780.4/73.5, 75.8/750.6, 38.7/38.6, 27.7, 27.4, 27.3, 27.2, 27.19, 27.15; HRMS calc'd for $C_{13}H_{22}NO_6$ (M$^+$+H): 288.1444, found: m/z 288.1452.

The oxime (2.88 g, 10 mmol) was stirred in cold (0° C.) THF (60 mL), and LiAlH$_4$ (1.0 M solution in THF, 25 mL, 25 mmol) was added. The mixture was refluxed for 3 h, stirred at room temperature for 12 h, and then quenched with EtOAc. The mixture was filtered through Celite. The filtrate was concentrated, and the residual oil was purified by flash column chromatography on silica gel (MeOH/CH$_2$Cl$_2$, 1:9) to afford amine 5 (1.67 g, 88%) as a yellow syrup. TLC (MeOH/ CH$_2$Cl$_2$, 1:9) R$_f$=0.1; [α]$_D^{20}$=+54.6 (c=1, CHCl$_3$) [lit.$_{S1}$ [α]$_D^{25}$=+41 (c=1.15, CH$_3$OH)]; IR (neat) 3359, 2911, 1756, 1298 cm$^{-1}$; $^1$H NMR (600 MHz, CDCl$_3$) δ 5.77 (1 H, d, J=3.7 Hz), 4.45 (1 H, dd, J=4.2, 2.1 Hz), 3.87 (1 H, dd, J=11.8, 3.7 Hz), 3.77-3.70 (2 H, m), 3.17 (1 H, dd, J=9.5, 4.6 Hz), 1.52 (3 H, s), 1.35 (3 H, s); $^{13}$C NMR (150 MHz, CDCl$_3$) δ 112.1, 104.3, 80.7, 80.6, 61.5, 55.2, 26.6, 26.4; HRMS calcd for $C_8H_{16}NO_4$ (M$_+$+H): 190.1079, found: m/z 190.1080.

Example 2

O-Benzyl-2,3-O,N-isopropylidene-3-acetamido-3-deoxy-α-D-ribofuranoside (6)

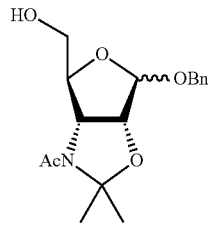

Amine 5 (1.67 g, 8.8 mmol) was stirred with Ac$_2$O (5 mL) in pyridine (10 mL) at room temperature for 3 h. The reaction was quenched by addition of MeOH (5 mL). The mixture was concentrated and coevaporated with toluene (3×) to remove Ac$_2$O and pyridine. The residual solid sample was recrystallized from EtOAc to give an acetylation product (2.35 g). A cold solution (0° C.) of the acetylation product and benzyl alcohol (5.84 g, 54 mmol) in toluene (16 mL) was treated with a solution of HCl (4.0 M) in 1,4-dioxane (7.5 mL, 30 mmol), and stirred for 24 h at room temperature. The reaction mixture was poured into Et$_2$O (100 mL), and neutralized with saturated NaHCO$_3$ solution (80 mL) at 0° C. The organic layer was separated, and washed with water (3×) and brine. The combined aqueous washings were extracted with Et$_2$O (6×). The organic extracts were combined, dried over MgSO$_4$, filtered, and concentrated under reduced pressure. The residual oil was purified by flash column chromatography on silica gel (MeOH/CH$_2$Cl$_2$, 1:19) to afford 2.10 g (85% yield for two steps) of the diol product O-benzyl-3-acetamido-3-deoxy-α-D-ribofuranoside as a mixture of anomers (α/β=7: 3) as shown by the $^1$H NMR analysis. An analytical sample of α-anomer was obtained by re-chromatography on silica gel (MeOH/CH$_2$Cl$_2$, 1:99), R$_f$=0.2. Colorless solid, mp 95-97° C.; [α]$_D^{20}$=-72.8 (c=0.5, CHCl$_3$); IR (neat) 3487, 2955, 1712, 1265 cm$^{-1}$; $^1$H NMR (600 MHz, CDCl$_3$) δ 7.35-7.27 (5 H, m), 6.38 (1 H, d, J=8.0 Hz), 4.74 (1 H, d, J=11.9 Hz), 4.52 (1 H, d, J=11.9 Hz), 4.24 (1 H, dd, J=7.9, 3.1 Hz), 3.99 (1 H, d, J=12.4 Hz), 3.92 (1 H, s), 3.74-3.71 (2 H, m), 3.41 (1 H, br s), 3.00 (1 H, br s), 2.01 (3 H, s); $_{13}$C NMR (150 MHz, CDCl$_3$) δ 170.1, 136.9, 128.5 (3×), 128.0 (2×), 98.9, 69.8, 69.1, 68.4, 63.6, 46.3, 23.4; HRMS calcd for $C_{14}H_{20}NO_5$ (M$_+$+H): 282.1341, found: m/z 282.1343.

A solution of the diol (2.10 g, 7.5 mmol as a mixture of α/β anomers), 2,2-dimethoxypropane (10 mL) and p-toluenesulfonic acid monohydrate (~0.2 g) in toluene (20 mL) was stirred at 80° C. for 4 h. The mixture was concentrated under reduced pressure, and the residue was recrystallized from Et$_2$O to give alcohol 6 (2.17 g, 90%) as a mixture of anomers (α/β=7:3) as shown by the $^1$H NMR analysis. An analytical sample of α-anomer was obtained by re-chromatography on silica gel (EtOAc/hexane, 1:9). Colorless crystal, mp 82-85° C.; TLC (EtOAc/hexane, 1:1) R$_f$=0.35; [α]$_D^{20}$=-125.6 (c=1, CHCl$_3$); IR (neat) 3501, 2988, 1732, 1288 cm$^{-1}$; $^1$H NMR (600 MHz, CDCl$_3$, as two rotamers (1:1)) δ 7.36-7.27 (5 H, m), 5.20 (0.5 H, s), 5.15 (0.5 H, s), 4.74 (0.5H, d, J=11.6 Hz), 4.68 (0.5 H, d, J=11.6 Hz), 4.64 (0.5 H, d, J=5.9 Hz), 4.61 (0.5 H, dd, J=5.9, 2.5 Hz), 4.59-4.57 (1.5 H, m), 4.45 (0.5 H, d, J=11.6 Hz), 4.34-4.33 (0.5 H, m), 4.22 (0.5 H, dd, J=8.1, 4.0 Hz), 4.02 (0.5 H, d, J=9.1 Hz), 3.81-3.74 (1 H, m), 3.69-3.66 (1 H, m), 2.72 (0.5 H, dd, J=9.1, 2.6 Hz), 2.14 (1.5H, s), 2.06 (1.5 H, m), 1.67 (1.5 H, s), 1.63 (1.5 H, s), 1.53 (1.5 H, s), 1.52 (1.5 H, s); $^{13}$C NMR (150 MHz, CDCl$_3$) δ 167.6/167.3, 136.5/136.1, 128.7/128.6 (2×), 128.4/128.29, 128.27/128.1 (2×), 106.2/105.0, 98.2/95.7, 89.2/89.1, 84.2/82.4, 70.4/69.4, 65.1/61.7, 64.4, 28.2/26.3, 26.0/24.4, 24.2/21.9; HRMS calcd for $C_{17}H_{23}NNaO_5$(M$^+$+Na): 344.1474, found: m/z 344.1477.

Example 3

Ethyl (O-benzyl-2,3-O,N-isopylidene-3-acetamido-3,5,6-trideoxy-6-diethoxyphosphoryl-D-riboheptofuranoside)uronate (7a)

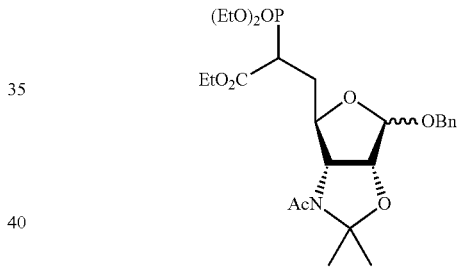

A solution of alcohol 6 (2.17 g, 6.76 mmol) and pyridine (1.2 mL, 14.73 mmol) in CH$_2$Cl$_2$ (20 mL) was stirred at -15° C., while trifluoromethanesulfonic anhydride (Tf$_2$O, 1.49 mL, 8.86 mmol) was added dropwise over a period of 30 min. The mixture was stirred for another 2 h at -15° C., quenched with MeOH (1 mL), and washed successively with ice water and cold aqueous KH$_2$PO$_4$ solution (1 M). The aqueous layer was extracted with EtOAc (3×). The combined organic phase was dried over MgSO$_4$, filtered, concentrated, and coevaporated with toluene to remove pyridine. The crude triflate product (3.06 g) was used in the next step without further purification.

NaH (0.41 g, 10.2 mmol; 60% dispersion in oil) was washed with anhydrous hexane (3×) under an atmosphere of nitrogen, added DMF (30 mL), and stirred at 0° C. in an ice bath. A solution of triethyl phosphonoacetate (1.95 g, 10.9 mmol) in DMF (10 mL) was added dropwise over a period of 30 min. The ice bath was removed, and the mixture was stirred for 2 h to give a clear yellow solution. The above-prepared triflate (3.06 g, ~6.76 mmol) in DMF (10 mL) was then added, followed by 2 drops of 15-crown-5. The resulting solution was stirred at room temperature for 24 h, cooled to 0° C., and quenched with aqueous KH$_2$PO$_4$ (1M solution). The mixture was extracted with CH$_2$Cl$_2$ (5×). The combined organic layers were washed with water, dried over MgSO$_4$, filtered, and concentrated under reduced pressure. The residual brown oil was purified by flash column chromatography on silica gel (EtOAc/hexane gradients, 1:4 to 1:1) to afford product 7a (2.85 g, 80% yield from 6) as a mixture of α/β anomers.

An analytical sample of α-anomer was prepared by re-chromatography on silica gel (EtOAc/hexane, 1:4). TLC (MeOH/CH$_2$Cl$_2$, 1:19) R$_f$=0.2; $^1$H NMR (600 MHz, CDCl$_3$, as rotamers of diastereomers) δ 7.33-7.26 (5 H, m), 5.15 (1 H, s), 4.74 (1 H, d, J=11.9 Hz), 4.68 (1 H, d, J=5.8 Hz), 4.46 (1 H, d, J=11.9 Hz), 4.29-4.19 (4 H, m), 4.12-4.05 (3 H, m), 4.00 (1 H, d, J=12.4 Hz), 3.41 (1 H, dd, J=12.4, 10.3 Hz), 2.45-2.35 (1 H, m), 2.22-2.18 (1 H, m), 2.12 (3 H, s), 1.60 (3 H, m), 1.48 (3 H, s), 1.31-1.24 (9 H, m); HRMS calcd for C$_{25}$H$_{39}$NO$_9$P (M$^+$+H): 528.2362, found: m/z 528.2366.

Example 4

O-Benzyl-2,3-O,N-isopropylidene-3-acetamido-3,5,6-trideoxy-6,6-bis(diethoxyphosphoryl)-D-ribo-hexofuranose (7b)

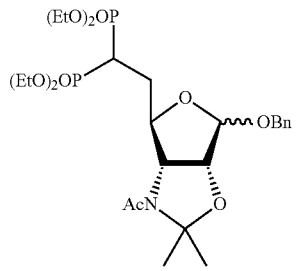

By a procedure similar to that for 7a, tetraethyl methylenediphosphonate (3.14 g, 10.9 mmol) was treated with NaH (0.31 g, 7.75 mmol; 60% dispersion in oil) in DMF (35 mL) fore h, and then reacted with the triflate of alcohol 6 (2.26 g in 8 mL of DMF) in the presence of 15-crown-5 (2 drops). The reaction mixture was stirred for 24 h at room temperature, worked up, and purified by flash column chromatography on silica gel (EtOAc/hexane gradients, 1:4 to 1:1) to afford product 7b (2.16 g, 73% yield from 6) as a mixture of α/β anomers. An analytical sample of α-anomer was prepared by re-chromatography on silica gel (MeOH/CH$_2$Cl$_2$, 1:99). TLC (MeOH/CH$_2$Cl$_2$, 1:19) R$_f$=0.14; $_1$H NMR (600 MHz, CDCl$_3$, as two rotamers) δ 7.37-7.27 (5 H, m), 5.15 (1 H, s), 4.79-4.74 (1 H, m), 4.69-4.67 (1 H, m), 4.59-4.57 (1 H, m), 4.49-4.44 (2H, m), 4.22-4.04 (8 H, m), 2.86-2.76 (1 H, m), 2.47-2.35 (1 H, m), 2.30-2.21 (1H, m), 2.11 (3 H, s), 1.61 (3 H, s), 1.50 (3 H, s), 1.33-1.29 (12 H, m); HRMS calcd for C$_{26}$H$_{43}$NNaO$_{10}$P$_2$ (M$_+$+Na): 614.2260, found: m/z 614.2268.

Example 5

Ethyl (3S,4R,5R)-3,4-O,N-isopropylidene-4-acetamido-3,5-dihydroxy-1-cyclohexene-1-carboxylate (8a)

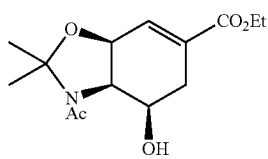

The phosphonate 7a (2.85 g, 5.4 mmol) was subjected to hydrogenolysis by stirring with Pd/C (0.5 g) in ethanol (30 mL) for 24 h at room temperature under an atmosphere of hydrogen. The mixture was filtered through Celite, and the filtrate was concentrated to yield the desired lactol (2.36 g) as pale yellow syrup. Under an atmosphere of nitrogen, a solution of lactol (2.36 g) in THF (10 mL) was added dropwise to the suspension of NaH (7.0 mmol, 0.28 g of 60% oil dispersion prewashed three times with hexane) in THF (20 mL). The mixture was stirred at room temperature for 1 h to complete the intramolecular Wittig-Horner-Emmons reaction. The mixture was cooled to 0° C., quenched with aqueous KH$_2$PO$_4$ (1 M solution), and extracted with CH$_2$Cl$_2$ (5×). The combined organic layers were dried over MgSO$_4$, filtered, and concentrated under reduced pressure. The residue was purified by flash column chromatography (EtOAc/hexane, 1:1) to afford the cyclohexenecarboxylate 8a (1.27 g, 83% yield from 7a) as a colorless oil. TLC (EtOAc) R$_f$=0.3; [α]$_D^{20}$=-15.6 (c=2.6, CHCl$_3$); IR (neat) 3492, 1769, 1655, 1221 cm$_{-1}$; $^1$H NMR (600 MHz, CDCl$_3$, as two rotamers) δ 7.07 (0.8 H, d, J=3.4 Hz), 6.99 (0.2 H, d, J=3.4 Hz), 4.61 (0.8 H, d, J=5.9 Hz), 4.56 (0.8 H, d, J=5.9 Hz), 4.47 (0.2 H, dd, J=6.0, 3.4 Hz), 4.28-4.19 (3 H, m), 4.47 (0.8 H, dd, J=6.0, 3.4 Hz), 3.03 (0.8 H, dd, J=18.0, 2.8 Hz), 2.84 (0.2 H, dd, J=18.0, 2.8 Hz), 2.38-2.27 (1 H, m), 2.19 (0.6 H, s), 2.14 (2.4 H, s), 2.09 (0.8 H, d, J=9.2 Hz), 1.98 (0.2 H, d, J=9.2 Hz), 1.70 (3 H, s), 1.62 (3 H, s), 1.31-1.27 (3 H, m); $^{13}$C NMR (150 MHz, CDCl$_3$) δ 168.0/167.4, 166.1/165.9, 132.2/131.8, 131.4/130.7, 95.8/93.7, 68.7/68.4, 64.2/62.6, 61.3/61.1, 59.6/59.3, 31.1/30.6, 27.4/25.1, 26.3/23.8, 23.2/22.6, 14.1; HRMS calcd for C$_{14}$H$_{22}$NO$_5$ (M$_+$+H): 284.1498, found: m/z 284.1500.

Example 6

Diethyl (3S,4R,5R)-3,4-O,N-isopropylidene-4-acetamido-3,5-dihydroxy-1-cyclohexene-1-phosphonate (8b)

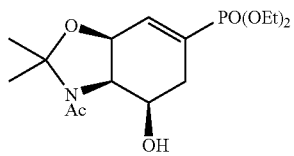

The bisphosphonate 7b (3.55 g, 6 mmol) was stirred with Pd/C (1 g) in ethanol (35 mL) at room temperature for 24 h under an atmosphere of hydrogen. The mixture was filtered through Celite, and sodium ethoxide (25 mL, 21% in ethanol) was added to the filtrate. The reaction mixture was stirred for 5 h, quenched with saturated aqueous NH$_4$Cl solution, and concentrated under reduced pressure. The residue was diluted by CH$_2$Cl$_2$, and washed with saturated aqueous NH$_4$Cl solution. The aqueous layer was extracted with CH$_2$Cl$_2$ (3×). The combined organic phase was dried over MgSO$_4$, filtered and concentrated. The residue was purified by flash column chromatography (MeOH/CH$_2$Cl$_2$, 1:99) to afford the cyclohexenephosphonate 8b (1.67 g, 80%) as a colorless oil.

Example 7

Ethyl (3S,4R,5S)-4-acetamido-5-azido-3-hydroxy-1-cyclohexene-1-carboxylate (9a)

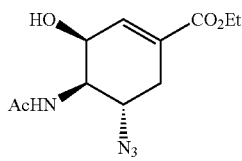

A solution of 8a (1.27 g, 4.5 mmol), triphenylphosphine (2.36 g, 9.0 mmol), diisopropyl azidocarboxylate (DIAD, 1.82 g, 9.0 mmol, freshly distilled) and diphenylphosphoryl azide (DPPA, 2.48 g, 9.0 mmol) in THF (40 mL) was stirred at room temperature for 48 h. The solvent was removed by rotary evaporation under reduced pressure, and the residue was purified by flash column chromatography (EtOAc/hexane, 1:3) to afford the corresponding azide product with 5S configuration (1.21 g, 87% yield). Colorless solid, mp 91-93° C.; TLC (EtOAc/hexane, 1:1) $R_f$=0.4; $[\alpha]_D^{20}$=+61.07 (c=3.2, CHCl$_3$); IR (neat) 2101, 1749, 1655, 1261 cm$_{-1}$; $^1$H NMR (600 MHz, CDCl$_3$, as two rotamers) δ 6.92-6.91 (1H, m), 4.57-4.56 (1 H, m), 4.24-4.19 (2 H, m), 3.71-3.66 (2 H, m), 30.02 (1 H, dd, J=15.4, 3.8 Hz), 2.26 (3 H, s), 2.23-2.19 (1 H, m), 1.66 (3 H, s), 10.62 (3 H, s), 1.28 (3 H, t, J=7.1 Hz); $^{13}$C NMR (150 MHz, CDCl$_3$) δ 168.8, 165.1, 133.3, 132.0, 95.9, 70.8, 61.4, 60.7, 60.1, 29.9, 27.8, 24.2, 23.7, 14.1; HRMS calcd for C$_{14}$H$_{21}$N$_4$O$_4$ (M$_+$+H): 309.1563, found: m/z 309.1562. The azide compound (1.21 g, 3.93 mmol) in ethanol (20 mL) was heated with aqueous HCl solution (5 mL, 1 M) at reflux for 1 h. The mixture was concentrated under reduced pressure, and the residue was purified by flash column chromatography (EtOAc) to afford the product 9a (1.01 g, 95% yield). Colorless solid, mp 51-53° C.; TLC (EtOAc) $R_f$=0.3; $[\alpha]_D^{20}$=+83.0 (c=1, CHCl$_3$); IR (neat) 3491, 2105, 1722, 1655, 1251 cm$_{-1}$; $_1$H NMR (600 MHz, CDCl$_3$) δ 6.86 (1 H, s), 6.21 (1 H, d, J=8.1 Hz), 4.42 (1 H, d, J=3.5 Hz), 4.19 (2 H, q, J=7.1 Hz), 4.11-4.07 (1 H, m), 3.79-3.74 (1 H, m), 2.86 (1H, dd, J=18.1, 5.1 Hz), 2.33 (1 H, dd, J=18.1, 8.7 Hz), 2.04 (3 H, 1.27 (3 H, t, J=7.1 Hz); $^{13}$C NMR (150 MHz, CDCl$_3$) δ 171.1, 165.8, 136.1, 130.4, 64.8, 61.3, 56.3, 52.1, 29.6, 23.3, 14.1; HRMS calcd for C$_{11}$H$_{17}$N$_4$O$_4$ (M$_+$+H): 269.1250, found: m/z 269.1253.

Example 8

Diethyl (3S,4R,5S)-4-acetamido-5-azido-3-hydroxy-1-cyclohexene-1-phosphonate (9b)

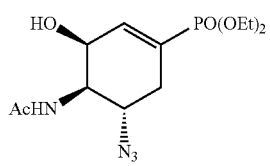

By a procedure similar to that for 9a, compound 8b (1.67 g, 4.8 mmol) was treated with Ph$_3$P (2.42 g, 9.2 mmol), freshly distilled DIAD (1.86 g, 9.2 mmol) and DPPA (2.54 g, 9.2 mmol) in THF (45 mL) for 48 h at room temperature to give the corresponding azide product (1.39 g, 78% yield) after purification by flash column chromatography (60% EtOAc/hexane, 3:2). The subsequent hydrolysis in refluxing EtOH/HCl (1 M aqueous solution) gave the desired product 9b (1.18 g, 95% yield), which was used directly for the preparation of 10b.

Example 9

Ethyl (3R,4R,5S)-4-acetamido-5-azido-3-hydroxy-1-cyclohexene-1-carboxylate (10a)

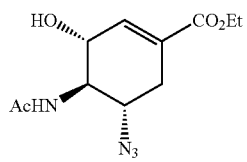

To a cold (−15° C.) solution of 9a (53.7 mg, 2 mmol) and pyridine (1.3 mL, 16 mmol) in CH$_2$Cl$_2$ (10 mL) was added Tf$_2$O (0.67 mL, 4 mmol) in CH$_2$Cl$_2$ (5 mL) dropwise, and stirred at −15~10° C. for 2 h. The mixture was washed with aqueous KH$_2$PO$_4$ (1 M solution, 2×), saturated aqueous NaHCO$_3$, water and brine. The organic layer was dried over MgSO$_4$ and concentrated in vacuo to give the corresponding triflate (0.82 g). The triflate was stirred with KNO$_2$ (85.6 mg, 10 mmol) and 18-crown-6 (3 drops) in anhydrous DMF (40 mL) for 24 h at 40° C. At the end of reaction, the mixture was diluted with CH$_2$Cl$_2$, and washed with brine. The organic layer was dried over MgSO$_4$ and concentrated under reduced pressure. The residue was purified by flash column chromatography (EtOAc/hexane, 4:1) to afford the product 10a with 3R configuration (0.3752 g, 70% yield). Colorless solid, mp 40-42° C.; TLC (EtOAc) $R_f$=0.35; $[\alpha]_D^{20}$=+45.5 (c=0.6, CHCl$_3$); IR (neat) 3501, 2101, 1699, 1538, 1214 cm$^{-1}$; $^1$H NMR (600 MHz, CDCl$_3$) δ 6.80 (1 H, d, J=2.4 Hz), 5.97 (1 H, br s), 5.20 (1 H, d, J=3.2 Hz), 4.38 (1 H, d, J=3.2 Hz), 4.21 (2 H, q, J=7.2 Hz), 3.65-3.57 (2 H, m), 2.95 (1 H, dd, J=16.3, 4.3 Hz), 2.45-2.40 (1 H, m), 2.09 (3 H, s), 1.28 (3 H, t, J=7.2 Hz); $^{13}$C NMR (150 MHz, CDCl$_3$) δ 173.7, 165.6, 138.3, 127.8, 71.2, 61.3, 57.9, 57.5, 29.5, 23.2, 14.1; HRMS calcd for C$_{11}$H$_{17}$N$_4$O$_4$ (M$_+$+H): 269.1250, found: m/z 269.1257.

Example 10

Diethyl (3R,4R,5S)-4-acetamido-5-azido-3-hydroxy-1-cyclohexene-1-phosphonate (10b)

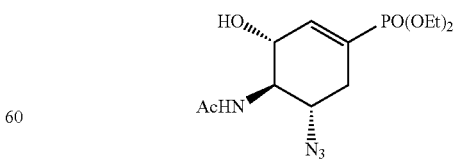

By a procedure similar to that for 10a, the above-prepared compound 9b (1.18 g, 3.55 mmol) was stirred with Tf$_2$O (1.2 mL, 7.1 mmol) and pyridine (2.3 mL, 28.5 mmol) in CH$_2$Cl$_2$ (10 mL) for 2 h at −15~−10° C. to give the corresponding triflate (1.65 g), which was subsequently treated with KNO$_2$ (1.52 g, 17.3 mmol) and 18-crown-6 (3 drops) in anhydrous DMF (50 mL) at 40° C. for 24 h to give the product 10b having 3R configuration (83.8 mg, 71% yield). Colorless oil; TLC (MeOH/CH$_2$Cl$_2$, 1:9) R$_f$=0.2; [α]$_D^{20}$=−11.3 (c=2.0, CDCl$_3$); IR (neat) 3499, 2108, 1755, 1634, 1240 cm$^{-1}$; $^1$H NMR (600 MHz, CDCl$_3$) δ 6.56 (1H, d, J$_{P-2}$=19.4 Hz), 6.13 (1 H, d, J=5.2 Hz), 4.95 (1 H, br s), 4.35 (1 H, dd, J=5.5, 3.4 Hz), 4.12-4.05 (4 H, m), 3.74-3.70 (1 H, m), 3.64-3.60 (1 H, m), 2.79-2.74 (1 H, m), 2.36-2.30 (1 H, m), 2.07 (3 H, s), 1.32 (6 H, t, J=7.1 Hz); $^{13}$C NMR (150 MHz, CDCl$_3$) δ 172.7, 142.3, 125.5 (C-1, d, J$_{P-1}$=184 Hz), 71.5, 62.5, 62.3, 57.9, 57.5, 29.9, 23.4, 16.39, 16.35; $^{31}$P NMR (162 MHz, CDCl$_3$) δ 16.54; HRMS calcd for C$_{12}$H$_{21}$N$_4$NaO$_5$P (M$_+$+Na): 3550.1147, found: m/z 3550.1152.

Example 11

Ethyl (3R,4R,5S)-4-acetamido-5-azido-3-(1-ethylpropoxy)-1-cyclohexene-1-carboxylate (11a). (Rohloff et al., J. Org. Chem. 1998, 63, 4545-4550)

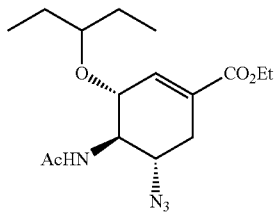

3-Pentyl trichloroacetimidate was prepared as follows. Under an atmosphere of nitrogen, a solution of 3-pentanol (8.815 g, 100 mmol) in anhydrous Et$_2$O (14 mL) was added dropwise to NaH (0.4 g, 10 mmol, 60% oil dispersion prewashed with hexane) suspended in Et$_2$O (10 mL). The mixture was stirred for 10 min at room temperature, and added dropwise over a period of 20 min to a cold (−5° C.) solution of trichloroacetonitrile (15 mL, 150 mmol) in Et$_2$O (20 mL) under an atmosphere of nitrogen. The reaction mixture was warmed to room temperature, and stirred for 2 h. After removal of solvent, the residue was triturated with MeOH/hexane (1:19, 10 mL) with vigorous stirring for 1 min to give precipitates, which were filtered off and washed with cold hexane. The filtrate was evaporated under reduced pressure to dryness, giving 3-pentyl trichloroacetimidate (16 g, 70% yield) as light brown oil. TLC (EtOAc/hexane, 1:4) R$_f$=0.3; $^1$H NMR (600 MHz, CDCl$_3$) δ 8.17 (1 H, br s, NH), 4.89 (1 H, m, J=6.0 Hz), 1.69 (4 H, qd, J=7.4, 6.0 Hz), 0.94 (6 H, t, J=7.4 Hz); $^{13}$C NMR (150 MHz, CDCl$_3$) δ 162.7, 92.2, 81.9, 25.7 (2×), 9.4 (2×); HRMS calcd for C$_7$H$_{13}$Cl$_3$NO (M$^+$+H): 232.0063, found: m/z 232.0067. Under an atmosphere of nitrogen, the freshly prepared 3-pentyl trichloroacetimidate (350 mg, 1.5 mmol) and CF$_3$SO$_3$H (13 μL, 0.15 mmol) were added to a solution of alcohol 10a (321 mg, 1.2 mmol) in CH$_2$Cl$_2$ (15 mL). The reaction mixture was stirred at room temperature for 24 h, during which more imidate and CF$_3$SO$_3$H (350 mg and 13 μL mmol) were added 5 times every 4 h period. The reaction was quenched with aqueous NaHCO$_3$ solution (5%). The aqueous layer was extracted with CH$_2$Cl$_2$ (2×). The combined organic phase was washed with brine, dried over MgSO$_4$ and concentrated in vacuo. The residue was purified by flash column chromatography (EtOAc/hexane, 3:7) to afford the alkylation product 11a (317 mg, 78% yield). Colorless solid, mp 115-117° C.; TLC (EtOAc/hexane, 1:1) R$_f$=0.4; [α]$_D^{20}$=−48.9 (c=1.1, CHCl$_3$); IR (neat) 2101, 1712, 1655 cm$^{-1}$; $^1$H NMR (600 MHz, CDCl$_3$) δ 6.75 (1 H, s), 5.98 (1 H, d, J=7.4 Hz), 4.53 (1 H, d, J=5.0 Hz), 4.51-4.16 (3 H, m), 3.33-3.28 (2 H, m), 2.82 (1 H, dd, J=17.6, 5.6 Hz), 2.22-2.16 (1 H, m), 2.00 (3 H, s), 1.49-1.45 (4 H, m), 1.25 (3 H, t, J=7.1 Hz), 0.95-0.80 (6 H, m); $^{13}$C NMR (150 MHz, CDCl$_3$) δ 171.1, 165.8, 137.9, 128.1, 82.0, 73.4, 61.0, 58.0, 57.2, 30.5, 26.2, 25.6, 23.5, 14.1, 9.5, 9.3; HRMS calcd for C$_{16}$H$_{27}$N$_4$O$_4$(M$_+$+H): 3390.2032, found: m/z 339.2035.

Example 12

Diethyl (3R,4R,5S)-4-acetamido-5-azido-3-(1-ethylpropoxy)-1-cyclohexene-1-phosphonate (11b)

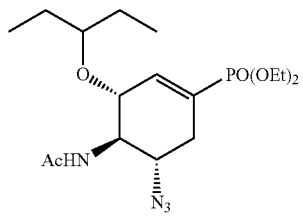

By a procedure similar to that for 11a, the reaction of alcohol 10b (498 mg, 1.5 mmol) with 3-pentyl trichloroacetimidate (420 mg, 1.8 mmol) in the presence of CF$_3$SO$_3$H (15.6 μL, 0.18 mmol), followed by another batches of the imidate and CF$_3$SO$_3$H, gave the alkylation product 11b (495 mg, 82% yield). Colorless oil; TLC (EtOAc/hexane, 1:1) R$_f$=0.2; [α]$_D^{20}$=−61.3 (c=0.65, CDCl$_3$); IR (neat) 2100, 1756, 1634, 1246 cm$^{-1}$; $^1$H NMR (600 MHz, CDCl$_3$) δ 6.56 (1 H, d, J$_{P-2}$=21.6 Hz), 5.71 (1 H, d, J=6.9 Hz), 4.52 (1 H, d, J=7.8 Hz), 4.34-4.30 (1 H, m), 4.11-4.01 (4 H, m), 3.31-3.23 (2 H, m), 2.69-2.64 (1 H, m), 2.12-2.08 (1 H, m), 2.01 (3 H, s), 1.51-1.43 (4 H, m), 1.39-1.31 (6 H, m), 0.90-0.81 (6 H, m); $^{13}$C NMR (150 MHz, CDCl$_3$) δ 171.0, 141.7, 126.3 (C-1, d, J$_{P-1}$=182 Hz), 810.9, 73.7, 62.14, 62.10, 54.3, 57.1, 31.0, 26.2, 25.4, 23.6, 16.4, 16.3, 9.6, 9.2; $^{31}$P NMR (162 MHz, CDCl$_3$) δ 16.99; HRMS calcd for C$_{17}$H$_{32}$N$_4$O$_5$P (M$_+$+H): 403.2110, found: m/z 403.2111.

Example 13

Ethyl (3R,4R,5S)-4-acetamido-5-amino-3-(1-ethylpropoxy)-1-cyclohexene-1-carboxylate phosphate (1, Tamiflu®)

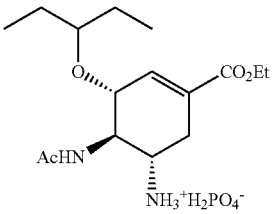

A solution of azide 11a (170 mg, 0.5 mmol) in ethanol (20 mL) was treated with Lindlar's catalyst (100 mg) under an atmosphere of hydrogen for 16 h at room temperature. The reaction mixture was filtered through Celite, and rinsed with ethanol. The filtrate was evaporated under reduced pressure to give colorless foam (155 mg), which was dissolved in ethanol (3 mL) and added slowly in portions to a hot (55° C.) solution of phosphoric acid (85%, 115 mg, 0.6 mmol) in ethanol (5 mL). Crystallization commenced within minutes. After cooling to 0° C., the precipitates were collected by filtration and rinsed with cold acetone (2×) to afford 1 (187 mg, 91% yield). White crystal, mp 189-191° C. [lit. (Fukuta et al., *J. Am. Chem. Soc.* 2006, 128, 6312-6313) mp 184-186° C.]; $[\alpha]_D^{20}=-35.8$ (c=1, $H_2O$) [lit. (Rohloff et al., *J. Org. Chem.* 1998, 63, 4545-4550.) $[\alpha]_D=-39.9$ (c=1, $H_2O$); or lit. (Fukuta et al., 2006) $[\alpha]_D^{22}=-30.5$ (c=0.480, $H_2O$)]; IR (neat) 3501, 1734, 1612, 1150 $cm^{-1}$, $^1H$ NMR (600 MHz, $D_2O$) δ 6.91 (1 H, s), 4.39 (1 H, d, J=8.0 Hz), 4.32-4.30 (2 H, m), 4.11 (1 H, dd, J=10.5, 5.7 Hz), 3.67-3.59 (2 H, m), 3.01 (1 H, dd, J=17.4, 5.4 Hz), 2.60-2.56 (1 H, m), 2.14 (3 H, s), 1.61-1.50 (4 H, m), 1.34 (3 H, t, J=7.1 Hz), 0.94 (3 H, t, J=7.3 Hz), 0.89 (3 H, t, J=7.3 Hz); $^{13}C$ NMR (150 MHz, $D_2O$) δ 178.1, 170.3, 140.7, 130.4, 87.2, 77.9, 65.2, 55.4, 52.0, 30.9, 28.3, 27.9, 25.2, 16.1, 11.36, 11.30; $^{31}P$ NMR (162 MHz, $D_2O$) δ 0.43; HRMS calcd for $C_{16}H_{29}N_2O_4$ ($M^+-H_3PO_4+H$): 313.2127, found: m/z 313.2123. Anal. Calcd for $C_{16}H_{31}N_2O_8P$: C, 46.83; H, 7.61; N, 6.83. Found: C, 46.70; H, 7.69; N, 6.74.

Example 14

(3R,4R,5S)-4-Acetamido-5-amino-3-(1-ethylpropoxy)-1-cyclohexene-1-carboxylic acid (2, Oseltamivir)

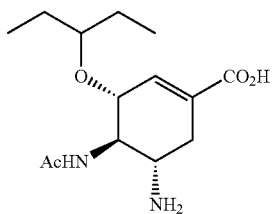

A solution of azide 11a (110 mg, 0.3 mmol) in ethanol (15 mL) was treated with Lindlar's catalyst (70 mg) under an atmosphere of hydrogen for 16 h at room temperature. The reaction mixture was filtered through Celite, and rinsed with ethanol. The filtrate was evaporated under reduced pressure to give colorless foam (95 mg), which was dissolved in THF (10 mL) and treated with aqueous KOH solution (1 M, 0.5 mL, 0.5 mmol) at 0° C. The reaction mixture was warmed to room temperature and stirred for 1 h. After which, the mixture was acidified to pH 5 with Amberlite IR-120, filtered and rinsed with aqueous ethanol (95%). The filtrate was concentrated under reduced pressure. The residue was purified on a $C_{18}$ column ($CH_3CN/H_2O$, 1:19) to afford 2 (75 mg, 88% yield). White solid, mp 185-187° C.; $[\alpha]_D^{20}=-143.2$ (c=0.4, $H_2O$); IR (neat) 3525, 2991, 1751, 1611, 1050 $cm^{-1}$; $^1H$ NMR (600 MHz, $D_2O$) δ 6.50 (1 H, s), 4.28 (1 H, d, J=8.4 Hz), 4.05 (1 H, dd, J=9.6, 4.8 Hz), 3.57-3.52 (2 H, m), 2.89 (1 H, dd, J=17.4, 5.4 Hz), 2.48 (1 H, dd, J=17.4, 10.8 Hz), 2.09 (3 H, s), 1.61-1.52 (3 H, m), 1.50-1.43 (1 H, m), 0.90 (3 H, t, J=7.5 Hz), 0.87 (3 H, t, J=7.5 Hz); $^{13}C$ NMR (150 MHz, $D_2O$) δ 175.1, 173.8, 133.0, 132.9, 84.2, 75.6, 52.9, 49.7, 29.5, 25.4, 25.1, 22.3, 8.54, 8.45; HRMS calcd for $C_{14}H_{24}N_2NaO_4$ ($M_++Na$): 307.1634, found: m/z 307.1633. Anal. Calcd for $C_{14}H_{24}N_2O_4$: C, 59.13; H, 8.51; N, 9.85. Found: C, 59.04; H, 8.58; N, 9.79.

Example 15

Ammonium (3R,4R,5S)-4-acetamido-5-amino-3-(1-ethylpropoxy)-1-cyclohexene-1-phosphonate (3, tamiphosphor)

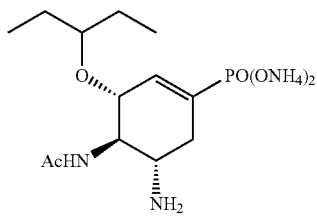

A solution of azide 11b (203 mg, 0.5 mmol) in ethanol (18 mL) was treated with Lindlar's catalyst (80 mg) under an atmosphere of hydrogen for 16 h at room temperature. The reaction mixture was filtered through Celite, and rinsed with ethanol. The filtrate was evaporated under reduced pressure to give colorless foam (185 mg), which was dissolved in $CHCl_3$ (15 mL) and treated with bromotrimethylsilane (2 mL, 15 mmol) at 0° C. The reaction mixture was warmed to room temperature and stirred for 24 h. After which, the mixture was concentrated under reduced pressure. The residue was taken up in water (10 mL), stirred for 2 h at room temperature, and subjected to lyophilization. The residual pale yellow solids were purified on a $C_{18}$ column by elution with aqueous $NH_4HCO_3$ (0.1 M solution) to afford the ammonium phosphonate 3 (150 mg, 85% yield). White solid, mp 240° C. (dec.), $[\alpha]_D^{20}=-56.0$ (c=0.8, $H_2O$); IR (neat) 3532, 3001, 1701, 1656, 1120 $cm^{-1}$; $^1H$ NMR (600 MHz, $D_2O$) δ 6.15 (1 H, d, $J_{P-2}$=18.8 Hz), 4.12 (1 H, d, J=8.1 Hz), 3.94 (1 H, dd, J=11.6, 9.2 Hz), 3.45-3.40 (2 H, m), 2.73-2.68 (1 H, m), 2.39-2.34 (1 H, m), 1.97 (3 H, s), 1.46-10.40 (3 H, m), 1.38-1.29 (1 H, m), 0.77 (3 H, t, J=7.3 Hz), 0.73 (3 H, t, J=7.3 Hz); $^{13}C$ NMR (150 MHz, $D_2O$) δ 175.0, 133.1, 132.9 (C-1, d, $J_{P-1}$=170 Hz), 84.3, 76.0, 520.9, 49.7, 29.3, 25.3, 25.0, 22.2, 8.5, 8.3; $^{31}P$ NMR (162 MHz, $D_2O$) δ10.35; HRMS calcd for $C_{13}H_{24}N_2O_5P$ $[M+H-2\ NH_4]^+$: 319.1434, found: m/z 319.1709. Anal. Calcd for C13H31N4O5P.H2O: C, 41.93; H, 8.93; N, 15.04. Found: C, 41.87; H, 8.99; N, 15.01.

Example 16

Ethyl (3R,4R,5S)-4-acetamido-5-[$N_2,N_3$-bis(tert-butoxycarbonyl)guanidino]-3-(1-ethylpropoxy)-1-cyclohexene-1-carboxylate (12a)

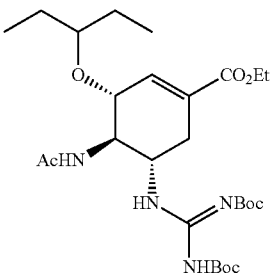

A solution of azide 11a (150 mg, 0.41 mmol) in ethanol (20 mL) was treated with Lindlar's catalyst (80 mg) under an atmosphere of hydrogen for 16 h at room temperature. The reaction mixture was filtered through Celite, and rinsed with ethanol. The filtrate was evaporated under reduced pressure to give colorless foam (110 mg), which was dissolved in anhydrous DMF (20 mL) and treated with N,N-bis(tert-butoxycarbonyl)thiourea (148 mg, 0.51 mmol) and Et$_3$N (148 μL, 1.03 mmol). The mixture was cooled to 0° C. and HgCl$_2$ (138 mg, 0.51 mmol) was added slowly. The suspension was warmed to room temperature and stirred for 10 h. After which, the reaction was diluted with EtOAc and filtered through a pad of Celite. The filtrate was concentrated and purified by flash column chromatography (EtOAc/hexane, 3:7) to afford guanidine 12a (177 mg, 78% yield). Colorless foam; TLC (EtOAc/hexane, 1:1) R$_f$=0.4; $[\alpha]_D^{20}$=−81.60 (c=1.0, CHCl$_3$); IR (neat) 3302, 1724, 1635, 1612, 1120 cm$^{-1}$; $^1$H NMR (600 MHz, CDCl$_3$) δ 11.36 (1 H, s), 8.60 (1 H, d, J=8.1 Hz), 6.78 (1 H, s), 6.21 (1 H, d, J=9.0 Hz), 4.37-4.34 (1 H, m), 4.17 (2 H, q, J=7.1 Hz), 4.14-4.08 (1 H, m), 3.98 (1 H, dd, J=4.3, 1.3 Hz), 3.32-3.30 (1 H, m), 2.74 (1 H, dd, J=17.8, 5.3 Hz), 2.35 (1 H, dd, J=17.8, 9.4 Hz), 1.87 (3 H, s), 1.50-1.44 (22 H, m), 1.24 (3 H, t, J=7.1 Hz), 0.86 (3 H, t, J=7.4 Hz), 0.83 (3 H, t, J=7.4 Hz); $^{13}$C NMR (150 MHz, CDCl$_3$) δ 170.2, 165.9, 163.1, 156.8, 152.5, 137.9, 128.6, 83.4, 82.6, 79.5, 76.1, 60.9, 54.3, 48.0, 30.4, 28.3 (3×), 28.0 (3×), 26.0, 25.7, 23.2, 14.1, 9.5, 9.3; HRMS calcd for C$_{27}$N$_4$O$_8$(M$^+$+H): 555.3394, found: m/z 555.3398.

Example 17

Diethyl (3R,4R,5S)-4-acetamido-5-[N$_2$,N$_3$-bis(tert-butoxycarbonyl)guanidino]-3-(1-ethylpropoxy)-1-cyclohexene-1-phosphonate (12b)

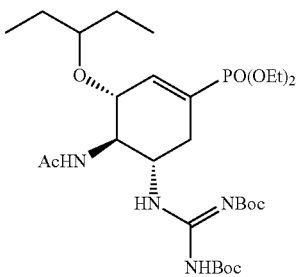

A solution of azide 11b (320 mg, 0.8 mmol) in ethanol (25 mL) was treated with Lindlar's catalyst (85 mg) under an atmosphere of hydrogen for 16 h at room temperature. The reaction mixture was filtered through Celite, and rinsed with ethanol. The filtrate was evaporated under reduced pressure to give colorless foam (255 mg), which was dissolved in anhydrous DMF (30 mL) and treated with N,N-bis(tert-butoxycarbonyl)thiourea (278 mg, 0.96 mmol) and Et$_3$N (267 μL, 1.92 mmol). The mixture was cooled to 0° C. and HgCl$_2$ (260 mg, 0.96 mmol) was added slowly. The suspension was warmed to room temperature and stirred for 16 h. After which, the reaction was diluted with EtOAc and filtered through a pad of Celite. The filtrate was concentrated and purified by flash column chromatography (MeOH/CH$_2$Cl$_2$, 3:97) to afford guanidine 12b (287 mg, 58% yield). Colorless foam; TLC (MeOH/CH$_2$Cl$_2$, 1:19) R$_f$=0.3; $[\alpha]_D^{20}$=−76.8 (c=1.6, CDCl$_3$); IR (neat) 3310, 1801, 1734, 1642, 1253 cm$^{-1}$; $^1$H NMR (600 MHz, CDCl$_3$) δ11.36 (1 H, s), 8.61 (1 H, d, J=8.2 Hz), 6.62 (1 H, d, J$_{P-2}$=21.7 Hz), 6.38 (1 H, d, J=8.9 Hz), 4.44-4.38 (1 H, m), 4.19-3.92 (6 H, m), 3.32-3.28 (1 H, m), 2.68-2.61 (1 H, m), 2.29-2.24 (1 H, m), 1.91 (3 H, s), 1.49-1.46 (22 H, m), 1.29 (6H, t, J=7.1 Hz), 0.86 (3 H, t, J=7.3 Hz), 0.82 (3 H, t, J=7.3 Hz); $^{13}$C NMR (150 MHz, CDCl$_3$) δ 170.8, 162.8, 156.9, 152.6, 142.1, 126.4 (C-1, d, J$_{P-1}$=181 Hz), 83.8, 82.6, 80.1, 76.3, 62.2, 62.1, 54.4, 48.2, 30.9, 28.2 (3×), 28.0 (3×), 26.0, 25.6, 23.4, 16.4, 16.3, 9.7, 9.2; $^{31}$P NMR (162 MHz, CDCl$_3$) δ 17.20; HRMS calcd for C$_{28}$H$_{52}$N$_4$O$_9$P (M$^+$+H): 619.3472, found: m/z 619.3476.

Example 18

(3R,4R,5S)-4-acetamido-5-guanidinyl-3-(1-ethylpropoxy)-1-cyclohexene-1-carboxylic acid (13a) (Kim et al., *J. Med. Chem.* 1998, 41, 2451-2460)

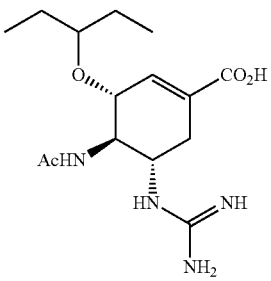

Aqueous KOH (0.5 mL of 1 M solution) was added to a solution of 12a (177 mg, 0.32 mmol) in THF (10 mL) at 0° C. The mixture was warmed to room temperature and stirred for 1 h, follow by treatment with Amberlite IR-120 (acidic resin). The mixture was filtered, and rinsed with aqueous ethanol (95%). The filtrate was concentrated; the residue was dissolved in CH$_2$Cl$_2$ (10 mL) and cooled to 0° C. Trifluoroacetic acid (5 mL) was added dropwise, and the mixture was stirred at 0° C. for 1 h. After which, the mixture was concentrated under reduced pressure, and the residue was purified on a C$_{18}$ column (CH$_3$CN/H$_2$O, 1:19) to afford the acid 13a (92 mg, 88% yield). Off-white solid, mp 90-92° C.; $[\alpha]_D^{20}$=−190.5 (c=0.36, H$_2$O); IR (neat) 3502, 2989, 1733, 1625, 1213 cm$^{-1}$; $^1$H NMR (600 MHz, D$_2$O) δ 6.86 (1 H, s), 4.36 (1 H, d, J=8.2 Hz), 3.94 (1 H, dd, J=10.1, 5.2 Hz), 30.87-3.82 (1 H, m), 3.56-3.54 (1 H, m), 2.87 (1 H, dd, J=17.5, 5.0 Hz), 2.42 (1 H, dd, J=17.5, 10.1 Hz), 2.05 (3 H, s), 1.60-1.54 (3 H, m), 1.50-10.44 (1 H, m), 0.91 (3 H, t, J=7.2 Hz), 0.86 (3 H, t, J=7.2 Hz); $^{13}$C NMR (150 MHz, D$_2$O) δ 174.7, 169.3, 156.8, 138.2, 128.7, 84.3, 75.3, 54.8, 50.5, 29.8, 25.6, 25.2, 21.9, 8.55, 8.50; HRMS calcd for C$_{15}$H$_{27}$N$_4$O$_4$ (M$^+$+H): 327.2032, found: m/z 327.2035. Anal. Calcd for C$_{15}$H$_{26}$N$_4$O$_4$: C, 55.20; H, 8.03; N, 17.17. Found: C, 55.10; H, 8.11; N, 17.14.

Example 19

Ammonium (3R,4R,5S)-4-acetamido-5-guanidinyl-3-(1-ethylpropoxy)-1-cyclohexene-1-phosphonate (13b)

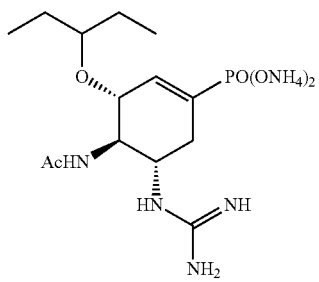

Bromotrimethylsilane (5 mL, 38 mmol) was added to a cold (0° C.) solution of 12b (287 mg, 0.46 mmol) in CHCl$_3$ (20 mL). The mixture was stirred for 24 h at room temperature, and then concentrated under reduced pressure. The residue was taken up in water (15 mL), stirred for 2 h at room temperature, and subjected to lyophilization. The residue was purified on a C$_{18}$ column (0.1 M aqueous NH$_4$HCO$_3$ solution) to afford ammonium phosphonate 13b (132 mg, 72% yield). White solid, mp 220-223° C.; $[\alpha]_D^{20}$=−55.3 (c=1.5, H$_2$O); IR (neat) 3512, 2901, 1716, 1101 cm$^{-1}$; $^1$H NMR (600 MHz, D$_2$O) δ 6.12 (1 H, d, J$_{P-2}$=19.0 Hz), 4.12 (1 H, d, J=6.9 Hz), 3.80 (1 H, dd, J=10.0, 5.0 Hz), 3.71-3.62 (1 H, m), 3.41 (1 H, br s), 2.62-2.59 (1 H, m), 2.28-2.23 (1 H, m), 1.91 (3 H, s), 1.46-1.44 (3H, m), 1.34-1.28 (1 H, m), 0.77 (3 H, t, J=7.3 Hz), 0.72 (3 H, t, J=7.3 Hz); $^{13}$C NMR (150 MHz, D$_2$O) δ 174.5, 156.6, 134.3 (C-1, d, J$_{P-1}$=168 Hz), 132.7, 84.2, 76.3, 55.2, 51.0, 30.8, 25.5, 25.2, 21.8, 8.6, 8.2; $^{31}$P NMR (162 MHz, D$_2$O) δ10.92; HRMS calcd for C$_{14}$H$_{26}$N$_4$O$_5$P [M+H−2 NH$_4$]$_+$: 361.1652, found: 361.1637. Anal. Calcd for C$_{14}$H$_{33}$N$_6$O$_5$P.(2H$_2$O): C, 38.88; H, 8.62; N, 19.43. Found: C, 38.74; H, 8.71; N, 19.39.

Example 20

(3R,4R,5S)-4-Acetamido-5-amino-3-hydroxy-1-cyclohexene-1-carboxylic acid (14a) (Kim et al., *J. Med. Chem.* 1998, 41, 2451-2460)

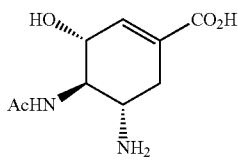

A solution of azide 10a (81 mg, 0.3 mmol) in ethanol (15 mL) was treated with Lindlar's catalyst (75 mg) under an atmosphere of hydrogen for 16 h at room temperature. The reaction mixture was filtered through Celite, and rinsed with ethanol. The filtrate was evaporated under reduced pressure to give colorless foam (95 mg), which was dissolved in THF (10 mL) and treated with aqueous KOH solution (0.5 mL of 1 M solution) at 0° C. The mixture was warmed to room temperature, stirred for 1 h, and acidified to pH 5 with Amberlite IR-120. The mixture was filtered and rinsed with aqueous ethanol (95%). The filtrate was concentrated, and the residue was purified on a C$_{18}$ column (CH$_3$CN/H$_2$O, 1:19) to afford the acid 14a (52 mg, 81% yield). White solid, mp 220° C. (dec.); $[\alpha]_D^{20}$=−96.9 (c=0.7, H$_2$O); IR (neat) 3511, 1711, 1610 cm$^{-1}$; $^1$H NMR (600 MHz, D$_2$O) δ 6.85 (1 H, s), 4.48 (1 H, d, J=8.7 Hz), 4.06 (1 H, dd, J=11.5, 5.6 Hz), 3.64-3.59 (1 H, m), 2.96 (1 H, dd, J=17.3, 5.6 Hz), 2.57-2.51 (1 H, m), 2.10 (3 H, s); $^{13}$C NMR (150 MHz, D$_2$O) δ 175.6, 169.0, 139.4, 127.5, 680.7, 53.6, 49.0, 28.2, 22.2; HRMS calcd for C$_9$H$_{15}$N$_2$O$_4$(M$^+$+H): 215.1032, found: m/z 215.1035.

Example 21

Ammonium (3R,4R,5S)-4-acetamido-5-amino-3-hydroxy-1-cyclohexene-1-phosphonate (14b)

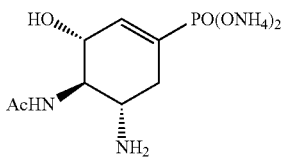

To a solution of azide 10b (101 mg, 0.3 mmol) in ethanol (15 mL) was treated with Lindlar's catalyst (50 mg) under an atmosphere of hydrogen for 16 h at room temperature. The reaction mixture was filtered through Celite, and rinsed with ethanol. The filtrate was evaporated under reduced pressure to give colorless foam (90 mg), which was dissolved in CHCl$_3$ (10 mL) and treated with bromotrimethylsilane (1 mL, 7.6 mmol) at 0° C. The mixture was warmed to room temperature, stirred for 24 h, and concentrated under reduced pressure. The residue was taken up in water (10 mL), stirred for 2 h at room temperature, and subjected to lyophilization. The residue was purified on a C$_{18}$ column (0.1 M aqueous NH$_4$HCO$_3$ solution) to afford the ammonium phosphonate 14b (64 mg, 85% yield). Colorless solid, mp 190-192° C.; $[\alpha]_D^{20}$=−56.3 (c=1.0, H$_2$O); IR (neat) 3500, 2891, 1728, 1159 cm$^{-1}$; $^1$H NMR (600 MHz, D$_2$O) δ 6.29 (1 H, d, J$_{P-2}$=19.1 Hz), 4.40 (1 H, d, J=7.0 Hz), 4.06 (1 H, dd, J=10.6, 5.3 Hz), 3.90 (1 H, dd, J=6.8, 3.4 Hz), 3.60 (1 H, br), 2.88-2.80 (1 H, m), 2.57-2.53 (1 H, m), 2.13 (3 H, s); $^{13}$C NMR (150 MHz, D$_2$O) δ 175.6, 135.0, 132.3 (C-1, d, J$_{P-1}$=172 Hz), 69.4, 54.1, 49.6, 29.3, 22.3; $^{31}$P NMR (162 MHz, D$_2$O) δ 13.52; HRMS calcd for C$_8$H$_{14}$N$_2$O$_5$P [M+H−2 NH$_4$]$_+$: 249.0651, found: m/z 249.0869.

Example 22

Viruses

Influenza A/WSN/1933 (H1N1) (from Dr. Shin-Ru Shih, Chang Gung University, Taiwan) was cultured in the allantoic cavities of 10-day-old embryonated chicken eggs for 72 h, and purified by sucrose gradient centrifugation.

Example 23

Cells

Madin-Darby canine kidney (MDCK) and 293T cells were obtained from American Type Culture Collection (Manassas, Va.), and were grown in DMEM (Dulbecco's modified Eagle medium, GibcoBRL) containing 10% fetal bovine serum (GibcoBRL) and penicillin-streptomycin (GibcoBRL) at 37° C. under 5% CO$_2$.

Example 24

Determination of Influenza Virus TCID$_{50}$

The TCID$_{50}$ (50% tissue culture infectious dose) was determined by serial dilution of the influenza virus stock onto 100 μL, MDCK cells at 1×10$_5$ cells/mL in 96-well microplates. The infected cells were incubated at 37° C. under 5.0% CO$_2$ for 48 h and added to each wells with 100 μL, per well of CellTiter 96® AQueous Non-Radioactive Cell Proliferation Assay reagent (Promega). After incubation at 37° C. for 15 min, absorbance at 490 nm was read on a plate reader. Influenza virus $TCID_{50}$ was determined using Reed-Muench method. (Reed and Muench, H. *Am. J. Hyg.* 1938, 27, 493-497).

Example 25

Preparation of Recombinant Neuraminidase Enzymes for NAI Evaluations

Figure 1B:
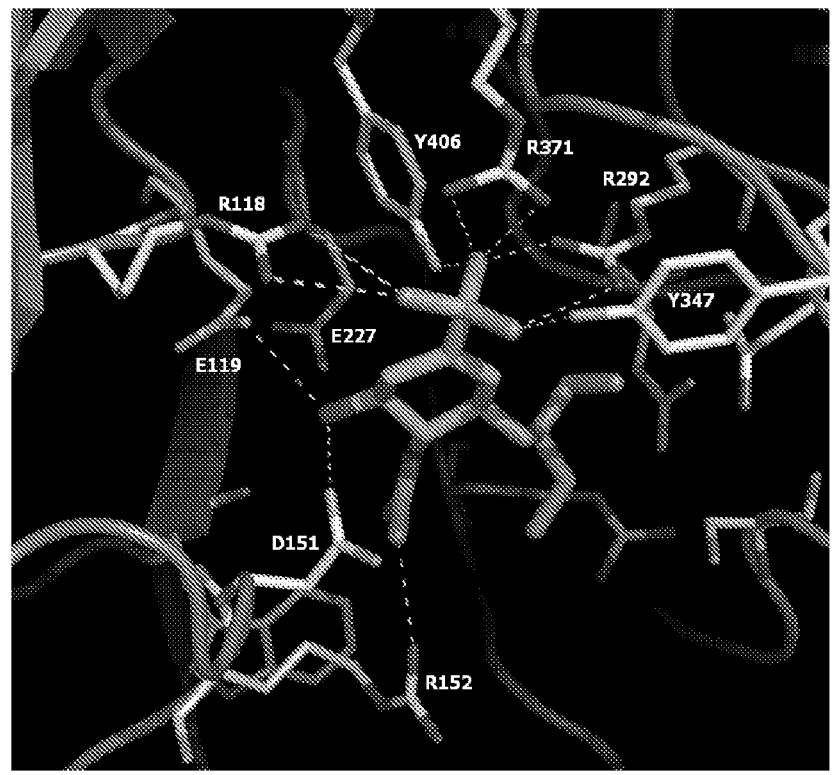
Figure 2:
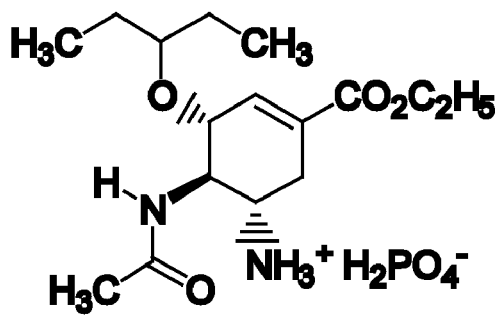
FIG. 2 shows molecular models of compounds 1, 3, 3b, 3c, 13b, and 13c.
Figure 2:
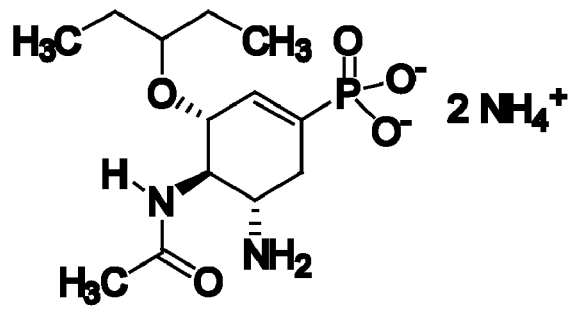
Figure 2:
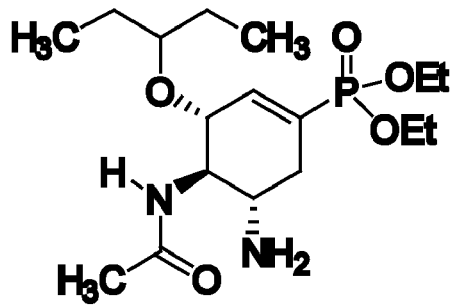
Figure 2:
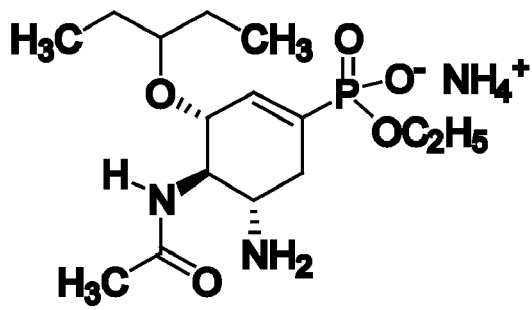
Figure 2:
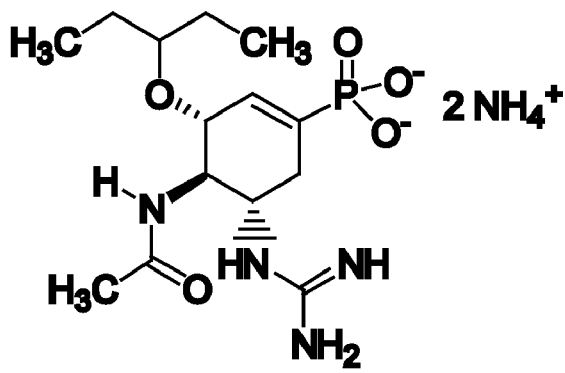
Figure 2:
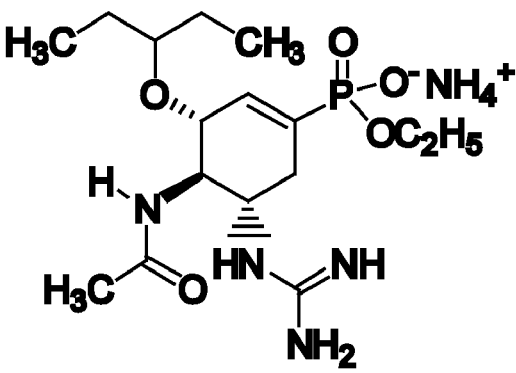

Two N1 group neuraminidases and their H274Y mutant forms were made. The cDNAs for NA(WNS) and NA(Hanoi) derived from NA genes of A/WSN/1933 (H1N1) and A/Hanoi/30408/2005 (H5N1), respectively, were obtained from Dr. King-Song Jeng (Institute of Molecular Biology, Academia Sinica) and Dr. Po-Huang Liang (Institute of Biological Chemistry, Academia Sinica), respectively. The NA genes were further mutagenized to introduce the H274Y mutations by GeneTailor Site-Directed Mutagenesis System (Invitrogen, Cal, USA) according to the manufacturer's instruction. The NA(WSN) and its mutant genes were cloned into pC1neo (Promega, W is, USA), and the NA(Hanoi) and its mutant genes were cloned into pcDNA6 (Invitrogen). Plasmid DNA of the NA genes were used to transfect into 293T cells to express recombinant neuraminidases at cell surface. The transfected cells were collected at 48 h, washed twice with PBS (pH 7.4), and used for the evaluation of neuraminidase inhibitors.

Example 26

Determination of NA Activity

The neuraminidase activity was measured using diluted allantoic fluid of influenza A/WSN/1933 (H1N1) infected embryonated eggs. A fluorescence assay was used to determine the NA activity with the fluorogenic substrate 2'-(4-methylumbelliferyl)-α-D-N-acetylneuraminic acid (MUNANA; Sigma). The fluorescence of the released 4-methylumbelliferone was measured in Envision plate reader (Perkin-Elmer, Wellesley, Mass.) using excitation and emission wavelengths of 365 and 460 nm, respectively. Neuraminidase activity was determined at 200 μM of MUNANA. Enzyme activity was expressed as the fluorescence of increase during 15 min incubation at room temperature.

Example 27

Determination of $IC_{50}$ and $K_i$ of NA Inhibitor

NA inhibition was determined by mixing inhibitor and neuraminidase for 10 min at room temperature followed by the addition of 200 AI of substrate. Inhibitor $IC_{50}$ value were determined from the dose-response curves by plotting the percent inhibition of NA activity versus inhibitor concentrations using Graph Pad Prism 4. Inhibitor $K_i$ value were determined by means of the formula $K_i=IC_{50}/(1+[S]/K_m)$(Cheng, Y.-C.; Prusoff, W. H. *Biochem. Pharmacol.* 1973, 22, 3099-3108), where [S] is substrate (MUNANA; Sigma) concentration used in $IC_{50}$ determination experiment, and $K_m$ is the concentration of substrate that produces half-maximal velocity. $K_m$ was determined by plotting using Michaelis-Menten equation.

Example 28

Determination of $EC_{50}$ and $CC_{50}$ of NA Inhibitor

Anti-flu activities of neuraminidase inhibitors were measured by the $EC_{50}$ values that were the concentrations of NA inhibitor for 50% protection of the H1N1 CPE activities. Fifty μL diluted H1N1 at 100 $TCID_{50}$ were mixed with equal volumes of NA inhibitors at varied concentrations. The mixtures were used to infect 100 μL of MDCK cells at $1\times10^5$ cells/mL in 96-wells. After 48 h incubation at 37° C. under 5.0% $CO_2$, cytopathic effects were determined with CellTiter 96® AQueous Non-Radioactive Cell Proliferation Assay reagent as described above. Inhibitor $EC_{50}$ value were determined by fitting the curve of percent CPE versus the concentrations of NA inhibitor using Graph Pad Prism 4. The $CC_{50}$ values measured the toxicity of NA inhibitors to MDCK cells and were determined similar to the $EC_{50}$ determination but without virus infection.

Example 29

In Vivo Assay

Female BALB/c mice (4-5 weeks old) were anesthetized with zoletil and inoculated intranasally with 25 μL of infectious influenza virus. Phosphonate compounds 3 and 3b and Tamiflu were administered to groups of 10 mice at dosages of 0.01, 0.1, 1.0 and 10 mg per kg of body weight per day by oral gavage twice daily for 5 days. Control (placebo) mice received sterile water on the same schedule. Four hours after the first dose of drug, mice were inoculated with 10 $MLD_{50}$ of influenza virus [A/WSN/33 (H1N1) or NIBRG-14 (H5N1)]. Mice were observed daily for 14 days for survival and body weight. Results on mean survival are shown in Tables 3 and 4. Results of individual survival rate and average body weight are shown in FIGS. 9 to 20.

Example 30

Computer Modeling of N1 Neuraminidase Inhibition

The model of the compound 3 in complex with the NA was constructed through docking the compound 3 to the crystallographic structure of influenza virus neuraminidase (N1 subtype, PDB code: 2HU4) (Russell et al., *Nature* 2006, 443, 45-49). The 3-D structure of compound 3 was built by modifying the 3-D structure of oseltamivir 2 (also from 2HU4) with SYBYL 7.3 program. (SYBYL 7.3; The Tripos Associates: St. Louis, Mo. The SYBYL computation was conducted at the National Center for High Performance Computing, Taiwan). GOLD 3.1.1 (Jones et al., *J. Mol. Biol.* 1995, 245, 43-53; Jones et al., *J. Mol. Biol.* 1997, 267, 727-748) was used to dock the compound 3 onto the protein with flexible docking option turned on. Kollmann-all atom charges (Cornell et al., *J. Am. Chem. Soc.* 1995, 117, 5179-5197) were assigned to the protein atoms, and Gasteiger-Hückel (Gasteiger and Marsili, *Tetrahedron* 1980, 36, 3219-3228; Marsili and Gasteiger, *Croat. Chem. Acta* 1980, 53, 601-614; Purcell and Singer, *J. Chem. Eng. Data* 1967, 12, 235-246) charges were assigned to ligand atoms using the SYBYL 7.3 program (Jones et al., *J. Mol. Biol.* 1997, 267, 727-748). Initial 1000 independent genetic algorithm cycles of computation were carried out with ligand torsion angles varying between −180 and 180 degree. The search efficiency was set at 200% to ensure the most exhaustive search for the docking conformational space. All other parameters were kept the same as the default settings. The docking processes were distributed to a 40-processor Linux cluster with Intel® Xeon™ CPU 3.00 GHz CPUs. The resultant ligand-protein complex structures were ranked with the GOLDSCORE scoring function to determine the top 1000 hits. Visual inspection of the top conformations confirmed that a consensus structure as shown in FIG. 1b was evident. The result was expected judging by the strong complementary electrostatic interaction between the key arginines in the NA and the phosphate group in the compound 3. The molecular models were displayed with the PyMOL software (DeLano WL (2002) The PyMOL molecular graphics system San Carlos (C.A.): DeLano Scientific). In FIG. 1, carbon atoms in the side chains of NA residues within 7 Å radius centered on the ligand are shown explicitly. Tentative hydrogen bonding donor-acceptor pairs are connected in dotted lines. The complex of the phosphonate compound 3a has more extensive hydrogen bonding interactions (8 pairs ligand-NA H-bonds) with key residues in the NA active site than the oseltamivir-NA complex (6 pairs ligand-NA H-bonds).

Example 31

Materials for Following Examples Synthetic Procedures and Product Characterization For the following Examples, all the reagents were commercially available and used without further purification unless indicated otherwise. All solvents were anhydrous grade unless indicated otherwise. Diisopropyl azodicarboxylate (DIAD) was purified by distillation on $Na_2SO_4$ under reduced pressure. All non-aqueous reactions were carried out in oven-dried glassware under a slight positive pressure of argon unless otherwise noted. Reactions were magnetically stirred and monitored by thin-layer chromatography on silica gel. Flash chromatography was performed on silica gel of 60-200 μm particle size. Yields are reported for spectroscopically pure compounds. Melting points were recorded on an Electrothermal MEL-TEMP® 1101D melting point apparatus and are not corrected. NMR spectra were recorded on Bruker AVANCE 600 and 400 spectrometers. Chemical shifts are given in δ values relative to tetramethylsilane (TMS); coupling constants J are given in Hz. Internal standards were $CDCl_3$ ($\delta H=7.24$), CD3OD ($\delta H=3.31$) or $D_2O$ ($\delta H=4.79$) for 1H-NMR spectra, $CDCl_3$ ($\delta c=77.0$) or CD3OD ($\delta c=49.15$) for $^{13}$C-NMR spectra, and $H_3PO_4$ in $D_2O$ ($\delta P=0.00$) for $^{31}$P-NMR spectra. The splitting patterns are reported as s (singlet), d (doublet), t (triplet), q (quartet), m (multiplet), br (broad) and dd (double of doublets). IR spectra were recorded on a Thermo Nicolet 380 FT-IR spectrometer. Optical rotations were recorded on a Perkin-Elmer Model 341 polarimeter. [α]D Values are given in units of $10^{-1}$ deg cm2 g-1. High resolution ESI mass spectra were recorded on a Bruker Daltonics spectrometer.

Appendix A is incorporated by reference as if fully disclosed herein it relates to the following Examples.

Example 31

N-[(1S,4S,5R,6R)-3,6-dibromo-4,5-(isopropylidene-dioxy)cyclohex-2-en-1-yl]acetamide (19)

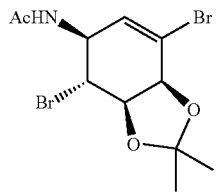

To a cold (0° C.) solution of cis-dihydrodiol 17 (8.0 g, 42.1 mmol) in a mixture of acetone (20 mL) and 2,2-dimethoxypropane (40 mL) was treated with p-toluenesulfonic acid monohydrate (100 mg, 0.52 mmol). The reaction mixture was stirred at room temperature for 30 min, after which time it was quenched by the addition of a saturated aqueous solution of $NaHCO_3$ (60 mL). The organic solvents were removed under reduced pressure, and the residual aqueous phase was extracted with $Et_2O$ (3×100 mL). The combined organic extracts were washed with brine (100 mL), dried over $MgSO_4$, filtered and concentrated in vacuo (do not heat) to provide the crude acetonide as a light yellow oil (8.92 g).

To a solution of N-bromoacetamide (NBA, 6.49 g, 47 mmol) in dry acetonitrile (250 mL) was added $SnBr_4$ (4.7 mL of 1 M solution in $CH_2Cl_2$, 4.7 mmol) and water (0.72 mL, 40 mmol) at 0° C. in the dark. The above-prepared acetamide (8.92 g, 38.8 mmol) in acetonitrile (150 mL) was added dropwise over a period of 1 h to the $NBA-SnBr_4$ mixture at the same temperature. The reaction was vigorously stirred for 8 h at 0° C. and then quenched with saturated aqueous $NaHCO_3$ (100 mL) and $Na_2SO_3$ (100 mL). The resulting mixture was allowed to warm up to room temperature for 30 min. After separation of organic phase, the aqueous phase was extracted with $CH_2Cl_2$ (3×300 mL). The combined organic layers were washed with water (3×200 mL) and brine (300 mL), dried over $MgSO_4$, filtered and concentrated in vacuo. The crude product was recrystallized from $Et_2O/CH_2Cl_2$ to give bromoacetamide 19 (11.66 g, 75% from cis-dihydrodiol 77) as colorless crystalline solids; m.p. 150-152° C. (dec.); TLC (EtOAc/hexane, 1:1) $R_f$=0.40; $[\alpha]_D^{20}$=+176.6 (c=1.63, $CHCl_3$), IR (film) 3209, 2988, 1655, 1225 cm$^{-1}$; $^1$H NMR (600 MHz, $CDCl_3$) δ 6.19 (1 H, d, J=9.1 Hz), 6.15 (1 H, d, J=5.0 Hz), 4.93-4.90 (1 H, m), 4.66 (1 H, d, J=5.0 Hz), 4.58 (1 H, dd, J=5.2, 2.6 Hz), 4.19 (1 H, dd, J=3.9; 2.0 Hz), 1.95 (3 H, s), 1.49 (3 H, s), 1.40 (3 H, s); $^{13}$C NMR (150 MHz, $CDCl_3$) δ 168.9, 127.9, 124.7, 112.0, 77.9, 75.8, 50.2, 44.3, 27.8, 26.5, 23.3; HRMS calcd for $C_{11}H_{16}Br_2NO_3$ (M$^+$+H): 367.9497, found: m/z 367.9499.

Example 32

(1S,4S,5S,6S)-7-Acetyl-3-bromo-4,5-isopropylidene-dioxy-7-azabicyclo[4.1.0]hept-2-ene (20).

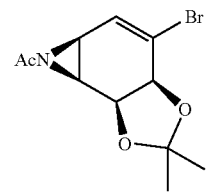

Lithium bis(trimethylsilyl)amide (35 mL of 1.0 M solution in THF, 35 mmol) was added dropwise to a stirred solution of bromoacetamide (11.66 g, 31.8 mmol) in THF (150 mL) at −10° C. under an atmosphere of nitrogen. The resulting solution was warmed to 0° C. and stirred for 30 min to give a brown suspension. After addition of buffer solution (100 mL, pH 7), the mixture was extracted with $Et_2O$ (4×150 mL). The combined organic extracts were washed with brine, dried over $MgSO_4$, filtered and concentrated. The crude aziridine 20 (8.32 g) was used in the next step without further purification.

A pure sample 20 for analysis was prepared by flash column chromatography of the crude product on silica gel (EtOAc/hexane, 2:3). Colorless solid; m.p. 110-112° C.; TLC (EtOAc/hexane, 1:1) $R_f$=0.42; $[\alpha]_D^{20}$=−77.6 (c=0.47, CHCl$_3$); IR (film) 2967, 1980, 1706, 1233, 1072 cm$^{-1}$; $^1$H NMR (600 MHz, CDCl$_3$) δ 6.69 (1 H, d, J=4.7 Hz), 4.72 (1 H, dd, J=7.0, 1.1 Hz), 4.45 (1 H, dd, J=7.0, 4.2 Hz), 3.19 (1 H, dd, J=5.9, 5.0 Hz), 3.10 (1 H, dd, J=5.6, 2.8 Hz), 2.16 (3H, s), 1.55 (3 H, s), 1.41 (3 H, s); $^{13}$C NMR (150 MHz, CDCl$_3$) δ 181.7, 129.9, 122.7, 108.5, 76.5, 71.9, 39.5, 36.7, 27.0, 24.8, 23.2; HRMS calcd for CH$_{11}$H$_{14}$BrNNaO$_3$ (M$^+$+Na): 310.0055, found: m/z 310.0058.

Example 33

N-[(1S,2R,5S,6S)-4-bromo-2-(1-ethylpropoxy)-5,6-(isopropylidenedioxy)cyclohex-3-en-1-yl]acetamide (22)

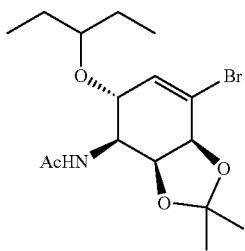

To a solution of crude aziridine 20 (8.32 g, 28.8 mmol) in 3-pentanol (50 mL) was added dropwise boron trifluoride etherate (4.68 mL, 36 mmol) at −10° C. The reaction mixture was warmed to 0° C., and stirred for 6 h, and concentrated under reduced pressure. The residue was dissolved in EtOAc (200 mL), and the organic layer was washed with saturated aqueous NaHCO$_3$ (50 mL). The aqueous layer was extracted with EtOAc (3×100 mL), and the combined organic layers were washed with water (200 mL) and brine (200 mL). The organic extract was dried over MgSO$_4$, filtered and concentrated. The residual oil was purified by flash column chromatography on silica gel (EtOAc/hexane, 3:7) to afford the ether product 22 (8.82 g, 73% from 20) as a colorless foam. TLC (EtOAc/hexane, 1:1) $R_f$=0.35; $[\alpha]_D^{20}$=−123 (c=1.42, CHCl$_3$), IR (film) 3221, 2988, 1921, 1711, 1199, 1075 cm$^{-1}$, $^1$H NMR (600 MHz, CDCl$_3$) δ 6.15 (1 H, d, J=2.1 Hz), 5.70 (1 H, d, J=9.0 Hz), 4.59 (1 H, dd, J=5.2, 1.7 Hz), 4.42 (1 H, dd, J=5.2, 2.6 Hz), 4.31 (1 H, ddd, J=11.5, 8.8, 2.6 Hz), 3.90-3.88 (1 H, m), 3.27-3.23 (1 H, m), 2.01 (3 H, s), 1.50-1.45 (4 H, m), 1.40 (3H, s), 1.36 (3 H, s), 0.89-0.85 (6 H, $^{13}$C NMR (150 MHz, CDCl$_3$) δ 169.9, 132.6, 122.7, 110.0, 82.3, 76.9, 76.1, 73.5, 51.3, 27.3, 26.3, 26.0, 25.6, 23.2, 9.5, 9.2; HRMS calcd for C$_{16}$H$_{27}$BrNO$_4$ (M$^+$+H): 376.1123, found: m/z 376.1129.

Example 34

N-[(1R,2R,5S,6S)-4-bromo-2-(1-ethylpropoxy)-5,6-dihydroxycyclohex-3-en-1-yl]acetamide (23)

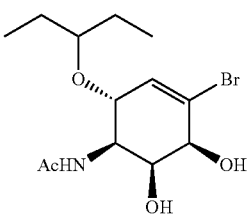

To a solution of acetonide 22 (8.82 g, 23.4 mmol) in methanol (100 mL), a conc. HCl solution (2 mL) was added. The reaction mixture was stirred at 50° C. for about 6 h until completion of the deprotection as shown by the TLC analysis. The mixture was cooled to room temperature, the solvent was evaporated under reduced pressure and the residual solid was recrystallized from Et$_2$O/THF to give dihydroxy acetamide 23 (7.42 g, 94%) as a colorless crystalline solid; m.p. 131-133° C. (dec.); TLC (EtOAc) $R_f$=0.35; $[\alpha]_D^{20}$=−101.2 (c=0.67, MeOH); IR (film) 3678, 3206, 2972, 1971, 1698, 1208, 1072 cm$^{-1}$; $^1$H NMR (600 MHz, CD$_3$OD) δ 6.04 (1 H, d, J=3.1 Hz), 4.13 (1 H, dd, J=1.7, 0.9 Hz), 3.95 (1 H, dd, J=4.3, 2.2 Hz), 3.92-3.89 (2 H, m), 3.32-3.29 (1 H, m), 1.86 (3 H, s), 1.44-1.33 (4 H, m), 0.85-0.79 (6 H, m); $^{13}$C NMR (150 MHz, CD$_3$OD) δ 173.3, 132.0, 128.1, 83.4, 75.9, 72.7, 70.8, 55.1, 27.5, 27.3, 23.0, 10.1, 9.9; HRMS calcd for C$_{13}$H$_{23}$BrNO$_4$ (M$^+$+H): 336.0810, found: m/z 336.0818

Example 35

(1S,2R,5R,6S)-6-acetamido-2,3-dibromo-5-(1-ethylpropoxy)-cyclohex-3-en-1-yl acetate (24)

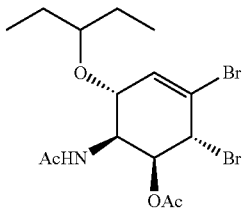

To a stirred solution of diol 23 (7.42 g, 22.1 mmol) in THF (150 mL) at 0° C. under nitrogen atmosphere, α-acetoxyisobutyryl bromide (4.1 mL, 27.8 mmol) was added dropwise over a period of 10 min. The reaction mixture was stirred at same temperature for 30 min, and warmed to room temperature with stirring for 3.5 h. The solvent was evaporated, and the residual oil was partitioned between EtOAc (200 mL) and 5% aqueous NaHCO$_3$ (50 mL). The organic layer was washed with water (100 mL), dried over MgSO$_4$, filtered and concentrated to afford the crude bromoacetate 24 (9.05 g). The crude product was used in the next step without further purification.

A pure sample 24 for analysis was prepared by flash column chromatography of the crude product on silica gel (EtOAc/hexane, 2:1). Light yellow foam; TLC (EtOAc/hexane, 2:1) $R_f$=0.33; $[\alpha]_D^{20}$=−43.2 (c=1.28, CHCl$_3$); IR (film) 3279, 2981, 1927, 1702, 1687, 1221, 1093 cm$^{-1}$; $^1$H NMR (600 MHz, CDCl$_3$) δ 6.17 (1 H, d, J=2.3 Hz), 50.85 (1 H, br s), 5.29 (1 H, s), 4.78-4.75 (1 H, m), 4.54 (1 H, d, J=2.8 Hz), 4.03 (1 H, d, J=8.6 Hz), 3.26 (1 H, dd, J=11.3, 5.6 Hz), 2.09 (3 H, s), 1.96 (3 H, s), 1.49-1.43 (4 H, m), 0.89-0.81 (6 H, m); $^{13}$C NMR (150 MHz, CDCl$_3$) δ 170.0, 169.9, 133.9, 121.1, 82.4, 75.4, 74.5, 48.8, 47.3, 26.2, 25.8, 23.4, 20.9, 9.4, 9.3; HRMS calcd for C$_{15}$H$_{24}$Br$_2$NO$_4$ (M$^+$+H): 440.0072, found: m/z 440.0076.

Example 36

N-[(1R,2R,6R)-4-bromo-2-(1-ethylpropoxy)-6-hydroxycyclohex-3-en-1-yl]acetamide (25)

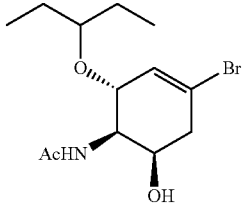

Super-Hydride® (LiBHEt$_3$, 61.5 mL of 1 M solution in THF, 61.5 mmol) was added dropwise to a stirred solution of bromoacetate 24 (9.05 g, 20.5 mmol) in THF (100 mL) at 0° C. under nitrogen atmosphere. The resulting solution was allowed to warmed to room temperature, stirred for 2 h, and treated with saturated aqueous NH$_4$Cl (50 mL). The aqueous layer was separated, and extracted with EtOAc (6×100 mL). The combined organic layers were washed with water (2×200 mL) and brine (200 mL). The organic phase was dried over MgSO$_4$, filtered and concentrated to afford a residue of light yellow foam. The crude product was purified by recrystallization from Et$_2$O to afford hydroxyacetamide 25 (5.78 g, 82% from diol 23) as white crystalline solids; m.p. 102-104° C.; TLC (EtOAc) R$_f$=0.35; $[\alpha]_D^{20}$=−107.7 (c=1.1, CHCl$_3$); IR (film) 3595, 3217, 2923, 1984, 1707, 1286, 1021 cm$^{-1}$; $^1$H NMR (600 MHz, CDCl$_3$) δ 6.03 (1 H, d, J=3.1 Hz), 5.89 (1 H, d, J=6.7 Hz), 4.23 (1 H, br s), 4.07 (1 H, br s), 3.98 (1 H, br s), 3.93 (1 H, dd, J=7.5, 2.1 Hz), 3.29-3.26 (1 H, m), 2.82 (1 H, dd, J=18.2, 4.7 Hz), 2.50 (1 H, dd, J=18.2, 5.8 Hz), 2.01 (3 H, s), 1.51-1.42 (4 H, m), 0.89-0.85 (6 H, m); $^{13}$C NMR (150 MHz, CDCl$_3$) δ 172.0, 127.9, 122.5, 81.7, 74.0, 67.7, 54.2, 41.7, 26.3, 26.0, 23.4, 9.7, 9.5; HRMS calcd for C$_{13}$H$_{22}$BrNNaO$_3$ (M$^+$+Na): 342.0681, found: m/z 342.0688.

Example 37

N-[(1R,2R,6S)-4-bromo-2-(1-ethylpropoxy)-6-azido-cyclohex-3-en-1-yl]acetamide (26) and N-[(1R,6R)-4-bromo-6-(1-ethylpropoxy)cyclohexa-2,4-dien-1-yl]acetamide (27)

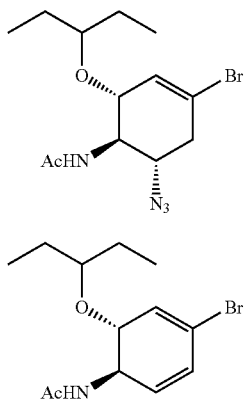

A solution of 25 (5.78 g, 18.1 mmol), triphenylphosphine (9.96 g, 38.0 mmol), freshly distilled diisopropyl azodicarboxylate (7.68 g, 38.0 mmol) and diphenylphosphorylazide (10.51 g, 38.0 mmol) in THF (120 mL) was stirred at 40° C. for 24 h. The solvent was removed by rotary evaporation under reduced pressure, and the residue was purified by flash column chromatography (EtOAc/hexane, 1:2) to afford the corresponding azide product 26 with 6S configuration (5.23 g, 84% yield), along with 2% of a side product of diene 27 (108 mg, 0.36 mmol).

Azide 26: White solid, m.p. 138-140° C.; TLC (EtOAc/hexane, 1:1) R$_f$=0.45; $[\alpha]_D^{20}$=−33.4 (c=0.7, CHCl$_3$); IR (film) 3119, 2927, 2178, 1902, 1698, 1277, 1054 cm$^{-1}$; $^1$H NMR (600 MHz, CDCl$_3$) δ 6.33 (1 H, d, J=7.8 Hz), 5.98 (1 H, d, J=2.2 Hz), 4.27 (1 H, d, J=8.2 Hz), 4.22-4.17 (1 H, m), 3.44-3.40 (1 H, m), 3.23-3.20 (1 H, m), 2.77 (1 H, dd, J=17.4, 5.8 Hz), 2.52-2.46 (1 H, m), 1.99 (3 H, s), 1.47-1.42 (4 H, m), 0.86-0.82 (6 H, m); $^{13}$C NMR (150 MHz, CDCl$_3$) δ 171.2, 130.3, 119.0, 82.0, 74.7, 57.5, 56.9, 40.4, 26.2, 25.6, 23.5, 9.6, 9.2; HRMS calcd for C$_{13}$H$_{22}$BrN$_4$O$_2$ (M$^+$+H): 345.0926, found: m/z 3450.0931.

Diene 27: Colorless solid, m.p. 68-70° C.; TLC (EtOAc/hexane, 2:1) R$_f$=0.60; $[\alpha]_D^{20}$=−215.6 (c=0.98, CHCl$_3$); IR (film) 3331, 1721, 1607, 1088 cm$^{-1}$; $^1$H NMR (600 MHz, CDCl$_3$) δ 6.16 (1 H, d, J=5.2 Hz), 6.09 (1 H, dd, J=9.8, 1.3 Hz), 5.81 (1 H, dd, J=9.8, 5.2 Hz), 5.52 (1 H, d, J=7.7 Hz), 4.60 (1 H, ddd, J=8.9, 4.8, 2.4 Hz), 3.91 (1 H, dd, J=4.8, 2.4 Hz), 3.43-3.39 (1 H, m), 1.94 (3 H, s), 1.49-1.41 (4 H, m), 0.88-0.82 (6 H, m); $^{13}$C NMR (150 MHz, CDCl$_3$) δ 169.9, 129.9, 128.0, 126.7, 120.0, 80.8, 74.8, 47.0, 26.6, 26.5, 23.3, 9.9, 9.5; HRMS calcd for C$_{13}$H$_{21}$BrNO$_2$ (M$^+$+H): 302.0756, found: m/z 302.0761.

Example 38

Ethyl (3R,4R,5S)-4-acetylamino-5-azido-3-(1-ethylpropoxy)-1-cyclohexene-1-carboxylate (28a)

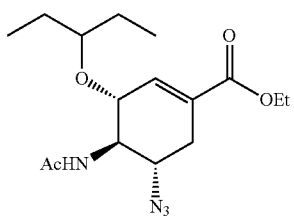

A solution of 26 (349 mg, 1 mmol), N,N-diisopropylethylamine (2.5 mL, 15.2 mmol) and bis(triphenylphosphine)dicarbonylnickel(0) (960 mg, 1.5 mmol) in ethanol (3 mL) and THF (15 mL) was stirred for 24 h at 80° C. under nitrogen atmosphere. The reaction mixture was cooled to room temperature, and the solvent was evaporated. The residual oil was diluted with EtOAc (20 mL), and the mixture was filtered through a pad of Celite. The filtrate was evaporated to give a light yellow oil, which was purified by flash column chromatography (EtOAc/hexane, 3:7) to afford ester 28a (274 mg, 81%) as colorless solids; m.p. 115-117° C.; TLC (EtOAc/hexane, 1:1) R$_f$=0.4; $[\alpha]_D^{20}$=−48.9 (c=1.1, CHCl$_3$); IR (film) 3401, 2101, 1712, 1655, 1273 cm$^{-1}$; $^1$H NMR (600 MHz, CDCl$_3$) δ 6.75 (1 H, s), 5.98 (1 H, d, J=7.4 Hz), 4.53 (1 H, d, J=5.0 Hz), 4.51-4.16 (3 H, m), 3.33-3.28 (2 H, m), 2.82 (1 H, dd, J=17.6, 5.6 Hz), 2.22-2.16 (1 H, m), 2.00 (3 H, s), 1.49-1.45 (4 H, m), 1.25 (3 H, t, J=7.1 Hz), 0.95-0.80 (6 H, m); $^{13}$C NMR (150 MHz, CDCl$_3$) δ 171.1, 165.8, 137.9, 128.1, 82.0, 73.4, 61.0, 58.0, 57.2, 30.5, 26.2, 25.6, 23.5, 14.1, 9.5, 9.3; HRMS calcd for C$_{16}$H$_{27}$N$_4$O$_4$ (M$^+$+H): 3390.2032, found: m/z 339.2039.

Example 39

Diethyl (3R,4R,5S)-4-acetamido-5-azido-3-(1-ethylpropoxy)-1-cyclohexene phosphonate (28b)

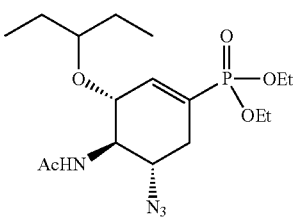

A mixture of 26 (1.72 g, 10 mmol), diethyl phosphite (2.07 g, 15 mmol) and 1,4-diazabicyclo[2.2.2]octane (3.37 g, 30 mmol) in anhydrous toluene (50 mL) was deoxygenated by bubbling with nitrogen for 10 min, and then added to tetrakis (triphenylphosphine)palladium(0) (867 mg, 0.75 mmol) that was placed in a round bottomed flask under nitrogen atmosphere. The resulting solution was gradually heated to 90° C. and maintained at this temperature for 12 h. The reaction mixture was filtered through Celite, and the filtrate was evaporated under reduced pressure to give colorless foam (3.91 g), which was purified by flash column chromatography (EtOAc/hexane, 1:1 to 2:1) to afford phosphonate 28b (3.33 g, 83%) as a colorless oil. TLC (EtOAc/hexane, 1:1) $R_f$=0.2; $[\alpha]_D^{20}$=−62.4 (c=1.2, $CHCl_3$); IR (film) 3357, 2108, 1754, 1651, 1247 $cm^{-1}$; $^1$H NMR (600 MHz, $CDCl_3$) δ 6.56 (1 H, d, $J_{P-2}$=21.6 Hz), 5.71 (1 H, d, J=6.9 Hz), 4.52 (1 H, d, J=7.8 Hz), 4.34-4.30 (1 H, m), 4.11-4.01 (4 H, m), 3.31-3.23 (2 H, m), 2.69-2.64 (1 H, m), 2.12-2.08 (1 H, m), 2.01 (3 H, s), 1.51-1.43 (4 H, m), 1.39-1.31 (6 H, m), 0.90-0.81 (6 H, m); $^{13}$C NMR (150 MHz, $CDCl_3$) δ 171.0, 141.7, 126.3 (C-1, d, $J_{P-1}$=182 Hz), 810.9, 73.7, 62.14, 62.10, 54.3, 57.1, 31.0, 26.2, 25.4, 23.6, 16.4, 16.3, 9.6, 9.2; $^{31}$P NMR (162 MHz, $CDCl_3$) δ 16.99; HRMS calcd for $C_{17}H_{32}N_4O_5P$ ($M^+$+H): 403.2110, found: m/z 403.2117.

Example 40

Tert-Butyl (1S,5R,6R)-6-acetamido-3-bromo-5-(1-ethylpropoxy)cyclohex-3-en-1-yl carbamate (29)

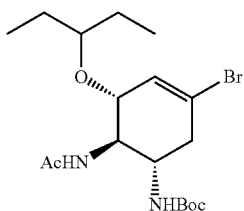

To a mixture of 2,3-dichloro-5,6-dicyano-1,4-benzoquinone (1.37 g, 6 mmol) and triphenylphosphine (1.57 g, 6 mmol) in anhydrous acetonitrile (30 mL) at room temperature was added tetrabutylammonium cyanate (1.71 g, 6 mmol) followed by addition of alcohol 25 (1.58 g, 5 mmol). The mixture was stirred for 18 h at room temperature until the reaction was completed. The solvent was evaporated and the black residue was dissolved in tert-butanol (20 mL). The resulting solution was heated at reflux for 24 h. The solvent was evaporated under reduced pressure, and the reside was purified by flash column chromatography (EtOAc/hexane, 3:7) to afford carbamate 29 (1.63 g, 78%) as white solids; m.p. 153-155° C.; TLC (EtOAc/hexane, 1:1) $R_f$=0.5; $[\alpha]_D^{20}$=−49.7 (c=1.35, $CHCl_3$); IR (film) 3327, 2919, 1708, 1682, 1523, 1244 $cm^{-1}$; $^1$H NMR (600 MHz, $CDCl_3$) δ 6.24 (1 H, d, J=9.1 Hz), 6.00 (1 H, s), 5.48 (1 H, d, J=9.1 Hz), 4.01 (1 H, dd, J=17.0, 9.3 Hz), 30.85-3.81 (2 H, m), 3.28-3.24 (1 H, m), 2.71 (1 H, dd, J=17.6, 4.8 Hz), 2.57 (1 H, dd, J=17.6, 8.6 Hz), 1.93 (3 H, s), 1.46-1.39 (4 H, m), 1.36 (9 H, s), 0.85-0.80 (6 H, m); $^{13}$C NMR (150 MHz, $CDCl_3$) δ 170.8, 156.0, 129.5, 121.2, 810.9, 79.6, 760.4, 53.1, 49.8, 40.6, 28.3 (3×), 26.0, 25.7, 23.2, 9.5, 9.2; HRMS calcd for $C_{18}H_{31}BrN_2NaO_4$ ($M^+$+Na): 441.1365, found: m/z 441.1368.

Example 41

Ethyl(3R,4R,5S)-4-acetamido-5-tert-butoxy-carbonylamino-3-(1-ethylpropoxy)-1-cyclohexene carboxylate (31a)

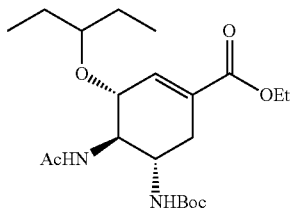

A mixture of vinyl bromide 29 (2.11 g, 5 mmol), potassium iodide (1.66 g, 10 mmol) and copper(I) iodide (477 mg, 2.5 mmol) in n-butanol (35 mL) was deoxygenated by bubbling with nitrogen for 10 min, and then added to N,N'-dimethylethylenediamine (54 µL, 0.5 mmol) that was placed in a round bottomed flask under nitrogen atmosphere. The reaction mixture was stirred for 24 h at 120° C. After cooling to room temperature, the solvent was evaporated under reduced pressure. The residue was partitioned between EtOAc (50 mL) and dilute aqueous ammonia solution (50 mL). The organic phase was washed with water (3×30 mL), dried over $MgSO_4$, and concentrated. The residue was filtered through a short column of silica gel (EtOAc/hexane, 1:1) to afford a colorless solid sample of crude vinyl iodide, which 30 (2.29 g) was used in the next step without further purification.

Palladium(II) acetate (90 mg, 0.4 mmol) was added to a solution of the above-prepared vinyl iodide 30 (2.29 g, 4.9 mmol) and sodium acetate (1.64 g, 20 mmol) in anhydrous ethanol (50 mL). The reaction mixture was stirred for 24 h at room temperature under an atmosphere of carbon monoxide. The solvent was evaporated, and the residue was purified by flash column chromatography (EtOAc/hexane, 3:7) to afford 31a (1.69 g, 82% from 29) as white solids; m.p. 142-144° C. [lit.$^{S3}$ m.p. 138-139° C.]; TLC (EtOAc/hexane, 1:1) $R_f$=0.35; $[\alpha]_D^{20}$=−76.3 (c=1.67, $CDCl_3$) [lit.$^{S3}$ $[\alpha]_D^{25}$=−68.9 (c=1.0, $CDCl_3$)]; IR (film) 3312, 2951, 1713, 1688, 1651, 1244 $cm^{-1}$; $^1$H NMR (600 MHz, $CDCl_3$) δ 6.70 (1 H, s), 6.24 (1 H, d, J=9.2 Hz), 5.26 (1 H, d, J=9.3 Hz), 4.18-4.12 (2 H, m), 4.03-3.98 (1 H, m), 3.95-3.94 (1 H, m), 3.75-3.72 (1 H, m), 3.30 (1 H, t, J=5.6 Hz), 2.67 (1 H, dd, J=17.8, 5.1 Hz), 2.27-2.23 (1 H, m), 1.93 (3 H, s), 1.48-1.42 (4 H, m), 1.37 (9 H, s), 1.24 (3 H, t, J=7.2 Hz), 0.86-0.81 (6 H, m); $^{13}$C NMR (150 MHz, $CDCl_3$) δ 170.9, 165.9, 156.3, 137.7, 129.2, 82.2, 79.5, 75.8, 60.9, 54.4, 49.2, 30.8, 28.3 (3×), 26.1, 25.6, 23.3, 14.1, 9.5, 9.2; HRMS calcd for $C_{21}H_{36}N_2NaO_6$ ($M^+$+Na): 4350.2471, found: m/z 435.2477.

Example 42

Diethyl (3R,4R,5S)-4-acetamido-5-tert-butoxy-carbonylamino-3-(1-ethylpropoxy)-1-cyclohexene phosphonate (31b)

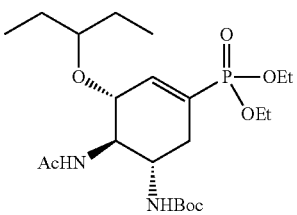

By a procedure similar to that for 28b, a mixture of vinyl bromide (4.21 g, 10 mmol), diethyl phosphite (2.12 g, 15 mmol), 1,4-diazabicyclo[2.2.2]octane (3.43 g, 30 mmol) in anhydrous toluene (50 mL) and tetrakis(triphenylphosphine)palladium(0) (872 mg, 0.75 mmol) was heated at 90° C. for 12 h. The reaction mixture was filtered through a pad of Celite, and the filtrate was partitioned between EtOAc (50 mL) and water (30 mL). The organic phase was washed again with water (30 mL) and brine (30 mL), dried over $MgSO_4$ and concentrated to give a crude product which was purified by recrystallization from $Et_2O/CH_2Cl_2$ to afford phosphonate 31b (4.05 g, 85%) as white crystalline solids; m.p. 167-169° C.; TLC (EtOAc) $R_f$=0.31; $[\alpha]_D^{20}$=−88.8 (c=1.14, $CHCl_3$); IR (film) 3378, 2901, 1733, 1626, 1262, 1159 cm$^{-1}$; $^1$H NMR (600 MHz, $CDCl_3$) δ 6.57 (1 H, d, $J_{P-2}$=21.6 Hz), 5.81 (1 H, d, J=9.0 Hz), 5.06 (1 H, d, J=8.9 Hz), 4.06-4.01 (5 H, m), 3.88 (1 H, br s), 3.79-3.75 (1 H, m), 3.30 (1 H, t, J=5.3 Hz), 2.60-2.57 (1 H, m), 2.20-2.16 (1 H, m), 1.95 (3 H, s), 1.48-1.44 (4 H, m), 1.39 (9 H, s), 1.30-1.27 (6 H, m), 0.87-0.82 (6 H, m); $^{13}$C NMR (150 MHz, $CDCl_3$) δ 170.9, 156.2, 141.5, 126.8 (C-1, d, $J_{P-1}$=181 Hz), 82.1, 79.6, 76.0, 62.0, 61.9, 54.2, 49.1, 31.0, 28.3 (3×), 26.0, 25.5, 23.3, 16.37, 16.33, 9.5, 9.1; $^{31}$P NMR (202 MHz, $CDCl_3$) δ 17.25; HRMS calcd for $C_{22}H_{42}N_2O_7P$ (M$^+$+H): 477.2730, found: m/z 477.2732.

Example 43

Ethyl (3R,4R,5S)-4-acetamido-5-amino-3-(1-ethylpropoxy)-1-cyclohexene carboxylate phosphate (15.$H_3PO_4$, Tamiflu®)

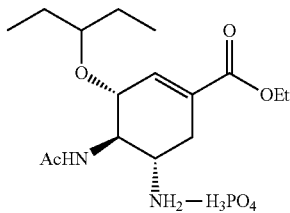

Compound 31a (1.24 g, 3 mmol) was dissolved in ethanol (20 mL) and added slowly in portions to a hot (50° C.) solution of phosphoric acid (10 mL of 1 M solution in ethanol, 10 mmol). The solution was stirred for 6 h at 50° C. After cooling to 0° C., the precipitates were collected by filtration and rinsed with cold acetone (3×5 mL) to afford Tamiflu (998 mg, 81%) as white crystals; m.p. 187-190° C. [lit. m.p. 184-186° C.]; $[\alpha]_D^{20}$=−36.7 (c=1, $H_2O$) [lit. $[\alpha]_D$=−39.9 (c=1, $H_2O$); or lit. $[\alpha]_D^{22}$=−30.5=0.480, $H_2O$)]; IR (film) 3501, 1734, 1612, 1150 cm$^{-1}$; $^1$H NMR (600 MHz, $D_2O$) δ 6.91 H, s), 4.39 (1 H, d, J=8.0 Hz), 4.32-4.30 (2 H, m), 4.11 (1 H, dd, J=10.5, 5.7 Hz), 3.67-3.59 (2 H, m), 3.01 (1 H, dd, J=17.4, 5.4 Hz), 2.60-2.56 H, m), 2.14 (3 H, s), 1.61-1.50 (4 H, m), 1.34 (3H, t, J=7.1 Hz), 0.94 (3 H, t, J=7.3 Hz), 0.89 (3 H, t, J=7.3 Hz); $^{13}$C NMR (150 MHz, $D_2O$) δ 178.1, 170.3, 140.7, 130.4, 87.2, 77.9, 65.2, 55.4, 52.0, 30.9, 28.3, 27.9, 25.2, 16.1, 11.36, 11.30; $^{31}$P NMR (162 MHz, $D_2O$) δ 0.43; HRMS calcd for $C_{16}H_{29}N_2O_4$ (M$^+$—$H_3PO_4$+H): 313.2127, found: m/z 313.2132. Anal. Calcd for $C_{16}H_{31}N_2O_8P$: C, 46.83; H, 7.61; N, 6.83. Found: C, 46.72; H, 7.68; N, 6.75.

Example 44

Ammonium (3R,4R,5S)-4-acetamido-5-amino-3-(1-ethylpropoxy)-1-cyclohexene phosphonate (3, Tamiphosphor)

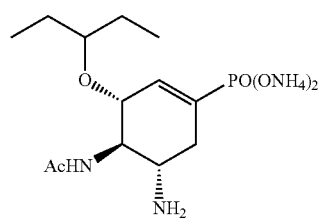

Diethylphosphonate 31b (2.38 g, 5 mmol) was dissolved in $CH_2Cl_2$ (50 mL) and treated with bromotrimethylsilane (6.67 mL, 50 mmol) at 0° C. The reaction mixture was warmed to room temperature, stirred for 18 h, and concentrated under reduced pressure. The residue was taken up in water (10 mL), stirred for 2 h at room temperature, and subject to lyophilization. The residual pale yellow solid residue was washed with $Et_2O$ (3×20 mL) to give white solids, which was dissolved in aqueous $NH_4HCO_3$ (0.1 M solution, 20 mL), stirred for 1 h at room temperature, and then lyophilization to afford Tamiphosphor (1.56 g, 88% yield) as white solids; m.p. 238-240° C. (dec.); $[\alpha]_D^{20}$=−56.7 (c=1.2, $H_2O$); IR (film) 3521, 3212, 2987, 1712, 1686, 1121 cm$^{-1}$; $^1$H NMR (600 MHz, $D_2O$) δ 6.15 (1 H, d, $J_{P-2}$=18.8 Hz), 4.12 (1 H, d, J=8.1 Hz), 3.94 (1 H, dd, J=11.6, 9.2 Hz), 3.45-3.40 (2 H, m), 2.73-20.68 (1 H, m), 2.39-2.34 (1 H, m), 1.97 (3 H, s), 1.46-1.40 (3 H, m), 1.38-1.29 (1 H, m), 0.77 (3 H, t, J=7.3 Hz), 0.73 (3 H, t, J=7.3 Hz); $^{13}$C NMR (150 MHz, $D_2O$) δ 175.0, 133.1, 132.9 (C-1, d, $J_{P-1}$=170 Hz), 84.3, 76.0, 52.9, 49.7, 29.3, 25.3, 25.0, 22.2, 8.5, 8.3; $^{31}$P NMR (162 MHz, $D_2O$) δ 10.35; HRMS calcd for $C_{13}H_{24}N_2O_5P$ [M+H−2 $NH_4$]$^+$: 319.1423, found: m/z 319.1429. Anal. Calcd for $C_{13}H_{31}N_4O_5P.H_2O$: C, 41.93; H, 8.93; N, 15.04. Found: C, 41.89; H, 8.99; N, 15.07.

Example 45

Ethyl (3R,4R,5S)-4-acetamido-5-amino-3-(1-ethylpropoxy)-1-cyclohexene-1-phosphonate ammonium salt (3c)

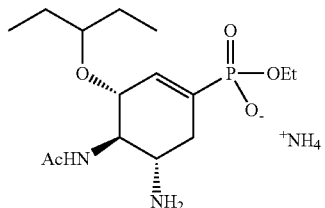

To a solution of diethyl ester 31b (1.43 g, 3 mmol) in ethanol (50 mL) was treated with sodium ethanoate in ethanol (4.5 mmol, 4.5 mL of 1 M solution) under a nitrogen atmosphere. The mixture was stirred for 16 h at room temperature, and then acidified with Amberlite IR-120 (H$^+$-form). The heterogeneous solution was stirred at 40° C. for 2 h, filtered and concentrated in vacuo. The residual oil was taken up in water (15 mL) and subjected to lyophilization. The residual colorless solids were washed with cold acetone (20 mL×3), dissolved in aqueous NH$_4$HCO$_3$ (15 mL of 0.1 M solution), stirred for 1 h at room temperature, and then lyophilization to afford ammonium salt 3c of Tamiphosphor monoester (898 mg, 82%) as white solids.

C$_{15}$H$_{32}$N$_3$O$_5$P, mp 65-67° C.; $[\alpha]_D^{20}$=−36.2 (c=0.7, H$_2$O); IR (neat) 3503, 3211, 2921, 1714, 1658, 1121 cm$^{-1}$; $^1$H NMR (600 MHz, D$_2$O) δ 6.33 (1 H, d, J$_{P-2}$=19.2 Hz), 4.23 (1 H, d, J=9.4 Hz), 3.99 (1 H, dd, J=10.2, 5.1 Hz), 3.86-3.84 (2 H, m), 3.53 (1 H, br s), 3.48-3.45 (1 H, m), 2.76-2.73 (1 H, m), 2.41-2.37 (1 H, m), 2.07 (3 H, s), 1.61-1.40 (4 H, m), 1.24 (3 H, t, J=6.8 Hz), 0.89 (3 H, t, J=7.1 Hz), 0.84 (3 H, t, J=7.1 Hz); $^{13}$C NMR (150 MHz, D$_2$O) δ175.1, 136.4, 130.3 (C-1, d, J$_{P-1}$=168 Hz), 84.2, 76.2, 76.1, 610.3, 53.6, 49.6, 29.9, 25.5, 25.2, 22.3, 15.8, 8.5; $^{31}$P NMR (242 MHz, D$_2$O) δ 12.89; HRMS calcd for C$_{15}$H$_{28}$N$_2$NaO$_5$P [M+Na−NH$_4$]$^+$: 370.1639, found: m/z 370.1643.

Example 46

Ethyl (3R,4R,5S)-4-acetamido-5-guanidinyl-3-(1-ethylpropoxy)-1-cyclohexene-1-phosphonate ammonium salt (13c)

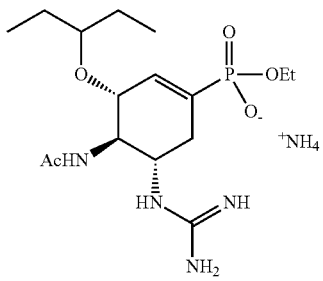

To a solution of diethyl ester 12b (2.73 g, 4 mmol) in ethanol (60 mL) was treated with sodium ethanoate in ethanol (6 mmol, 6 mL of 1 M solution) under a nitrogen atmosphere. The mixture was stirred for 18 h at room temperature, and then acidified with Amberlite IR-120 (H$^+$-form). The heterogeneous solution was stirred at 40° C. for 3 h, filtered and concentrated in vacuo. The residual oil was taken up in water (15 mL) and subjected to lyophilization. The residual colorless solids were washed with cold acetone (20 mL×3), dissolved in aqueous NH$_4$HCO$_3$ (15 mL of 0.1 M solution), stirred for 1 h at room temperature, and then lyophilization to afford ammonium salt 13c of Tamiphosphor guanidine monoester (1.22 g, 75%) as white solids.

C$_{16}$H$_{34}$N$_5$O$_5$P, mp 70-72° C.; $[\alpha]_D^{20}$=−11.5 (c=0.6, H$_2$O); IR (neat) 3521, 1931, 1756, 1623, 1210 cm$^{-1}$; $^1$H NMR (600 MHz, D$_2$O) δ 6.29 (1 H, d, J$_{P-2}$=19.1 Hz), 4.25-4.22 (1 H, m), 3.91-3.82 (4 H, m), 3.51 (1 H, br s), 2.57-2.55 (1 H, m), 2.24-2.20 (1 H, m), 2.01 (3 H, s), 1.63-1.49 (3 H, m), 1.44-1.40 (1 H, m), 1.24 (3 H, t, J=6.9 Hz), 0.88 (3 H, t, J=7.0 Hz), 0.82 (3 H, t, J=7.0 Hz); $^{13}$C NMR (150 MHz, D$_2$O) δ 174.5, 160.3, 136.5, 131.8 (C-1, d, J$_{P-1}$=171 Hz), 84.2, 76.9, 76.8, 61.2, 55.6, 51.0, 31.6, 25.6, 25.3, 22.0, 15.7, 8.5; HRMS calcd for C$_{16}$H$_{30}$N$_4$NaO$_5$P (M+Na−NH$_4$)$^+$: 412.1857, found: m/z 412.1859.

Example 47

Diethyl (3R,4R,5S)-4-acetamido-5-amino-3-(1-ethylpropoxy)-1-cyclohexene-1-phosphonate (3b)

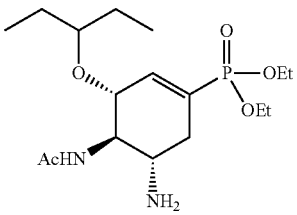

A solution of azide 11b (204 mg, 0.5 mmol) in ethanol (18 mL) was treated with Lindlar's catalyst (80 mg) under an atmosphere of hydrogen for 16 h at room temperature. The reaction mixture was filtered through Celite, and rinsed with ethanol. The filtrate was evaporated under reduced pressure to give colorless foam (183 mg), which was purified by flash column chromatography (MeOH/CH$_2$Cl$_2$, 1:4) to afford the diethyl phosphonate 3b (141 mg, 75% yield). light yellow oil; $[\alpha]_D^{20}$=−50.6 (c=2, CHCl$_3$); IR (neat) 3321, 2911, 1702, 1663, 1510 cm$^{-1}$; $^1$H NMR (600 MHz, CDCl$_3$) δ 6.51 (1 H, d, J$_{P-2}$=21.7 Hz), 6.29 (1 H, d, J=7.4 Hz), 4.06-4.00 (5 H, m), 3.55 (1 H, dd, J=18.5, 9.4 Hz), 3.28-3.26 (1 H, m), 3.19-3.09 (1 H, m), 2.59-2.56 (1 H, m), 2.28 (3 H, br s), 2.06-2.01 (1 H, m), 1.98 (3 H, s), 1.55-1.40 (3 H, m), 1.38-1.25 (6 H, m), 0.85-0.81 (6 H, m); $^{13}$C NMR (150 MHz, CDCl$_3$) δ 171.2, 141.7, 127.3 (C-1, d, J$_{P-1}$=180 Hz), 81.8, 750.4, 62.1, 62.0, 58.4, 49.6, 33.6, 26.1, 25.5, 23.5, 16.35, 16.32, 9.5, 9.2; $^{31}$P NMR (162 MHz, CDCl$_3$) δ 17.69; HRMS calcd for C$_{17}$H$_{34}$N$_2$O$_5$P [M+H]: 3770.2205, found: m/z 377.2207.

While the compositions and method have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:

1. A composition comprising:

a therapeutically effective amount of formula I:

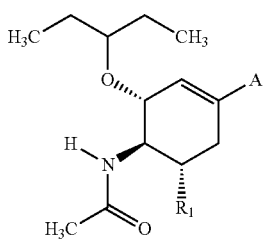

I wherein A is PO(OR)(OR'), where R and R' are independently selected from H, C1-C6 alkyl, aryl, and X, X being a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, calcium cation, and zinc cation; and $R_1$ is $NH_2$, $NH_3^+H_2PO_4^-$, or $NH(C=NH)NH_2$; and a pharmaceutical carrier.

2. The composition of claim 1, wherein formula I is:

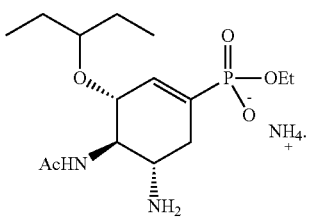

3. The composition of claim 1, wherein formula I is:

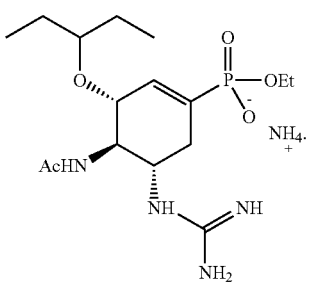

4. The composition of claim 1, wherein formula I is:

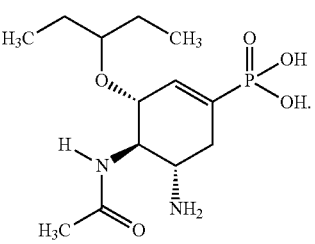

5. The composition of claim 1, wherein formula I is:

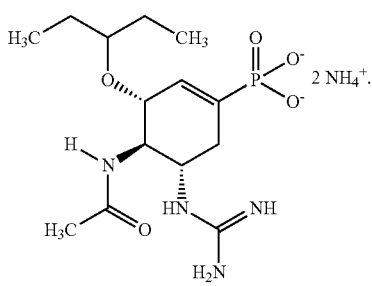

6. The composition of claim 1, wherein formula I is:

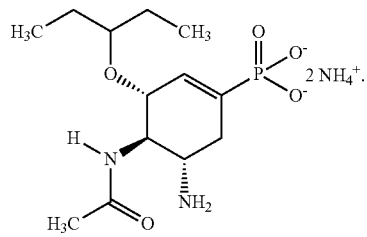

7. The composition of claim 1, wherein formula I is:

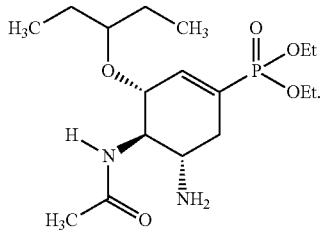

8. The composition of claim 1, wherein formula I is:

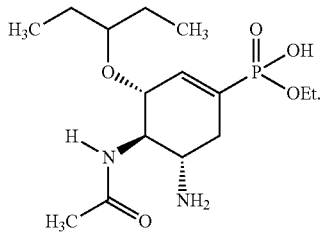

9. A composition comprising: a therapeutically effective amount of at least one of:

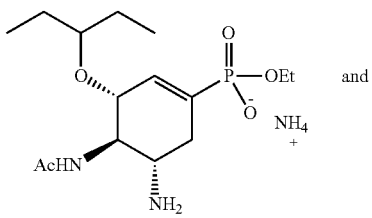

and

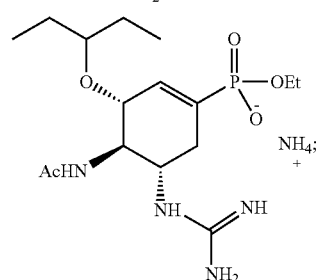

and a pharmaceutical carrier.

10. A method comprising: making a compound of formula I:

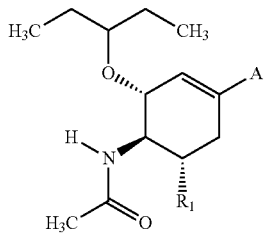

wherein A is PO(OR)(OR'), where R and R' are independently selected from H, C1-C6 alkyl, aryl, and X, X being a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, calcium cation, and zinc cation; and $R_1$ is $NH_2$, $NH_3^+H_2PO_4^-$, or $NH(C=NH)NH_2$;
according to at least one of the schemes of FIGS. 3-8.

11. A product prepared by the process of claim 10.

12. A method of inhibiting the activity of neuraminidase comprising: administering to an organism in need thereof a therapeutically effective amount of a composition having formula I:

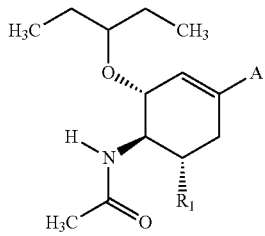

wherein A is PO(OR)(OR'), where R and R' are independently selected from H, C1-C6 alkyl, aryl and X, X being a cationic counterion selected from the group consisting of ammonium, methyl ammonium, dimethylammonium, trimethylammonium, tetramethylammonium, ethanol-ammonium, dicyclohexylammonium, guanidinium, ethylenediammonium cation, lithium cation, sodium cation, potassium cation, cesium cation, beryllium cation, magnesium cation, calcium cation, and zinc cation; and $R_1$ is $NH_2$, $NH_3^+H_2PO_4^-$, or $NH(C=NH)NH_2$.

13. The method of claim 12, wherein the organism is an animal.

14. The method of claim 13, wherein the organism is a human.

15. The method of claim 12, wherein the organism is exhibiting influenza-like symptoms.

16. The method of claim 12, wherein Formula I is:

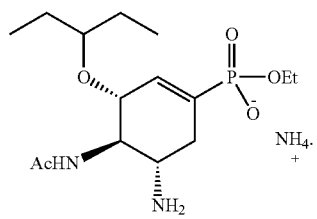

17. The method of claim 12, wherein formula I is:

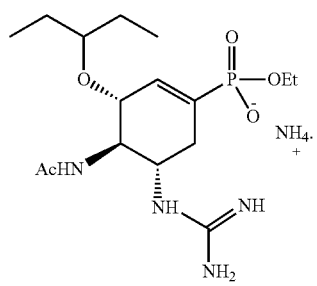

18. The method of claim 12, wherein formula I is:

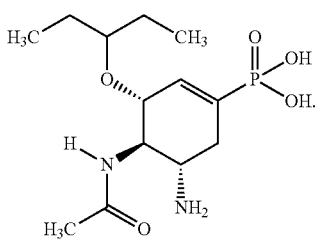

19. The method of claim 12, wherein formula I is:

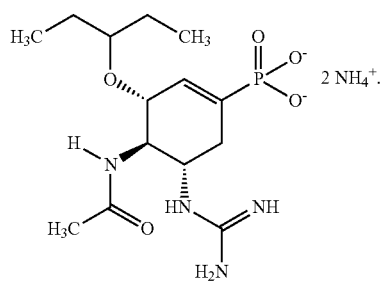

20. The method of claim 12, wherein formula I is:

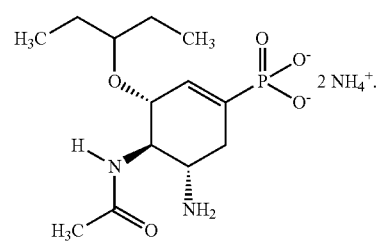

21. The composition of claim 1, wherein formula I is:

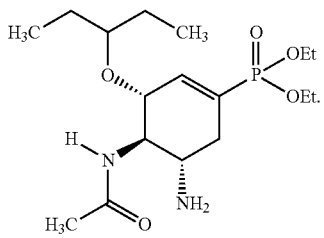

22. The method of claim 12, wherein formula I is:

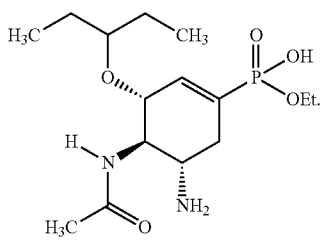

23. A method of inhibiting the activity of neuraminidase comprising: administering to an organism in need thereof a composition having a therapeutically effective amount of at least one of:

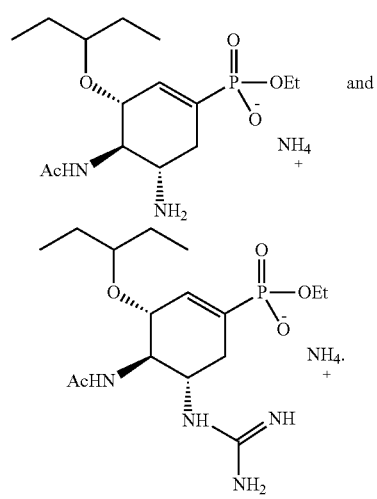

24. The method of claim 23, wherein the organism is an animal.

25. The method of claim 24, wherein the organism is a human.

26. The method of claim 23, wherein the organism is exhibiting influenza-like symptoms.

* * * * *